(12) United States Patent
Ettmayer et al.

(10) Patent No.: US 8,569,316 B2
(45) Date of Patent: Oct. 29, 2013

(54) PYRIMIDO [5,4-D] PYRIMIDINE DERIVATIVES FOR THE INHIBITION OF TYROSINE KINASES

(75) Inventors: Peter Ettmayer, Vienna (AT); Andreas Mantoulidis, Vienna (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 46 days.

(21) Appl. No.: 13/148,964

(22) PCT Filed: Feb. 17, 2010

(86) PCT No.: PCT/EP2010/051964
§ 371 (c)(1),
(2), (4) Date: Sep. 30, 2011

(87) PCT Pub. No.: WO2010/094695
PCT Pub. Date: Aug. 26, 2010

(65) Prior Publication Data
US 2012/0046270 A1 Feb. 23, 2012

(30) Foreign Application Priority Data
Feb. 17, 2009 (EP) .................... 09152991

(51) Int. Cl.
A01N 43/90 (2006.01)
A61K 31/519 (2006.01)
C07D 471/00 (2006.01)
C07D 487/00 (2006.01)

(52) U.S. Cl.
USPC ..................... 514/264.11; 544/279

(58) Field of Classification Search
None
See application file for complete search history.

(56) References Cited

U.S. PATENT DOCUMENTS

| | | | |
|---|---|---|---|
| 5,707,989 A | 1/1998 | Himmelsbach et al. |
| 5,821,240 A | 10/1998 | Himmelsbach et al. |
| 5,977,102 A | 11/1999 | Himmelsbach et al. |
| 7,166,628 B2 | 1/2007 | Cogan et al. |
| 7,214,802 B2 | 5/2007 | Cogan et al. |
| 7,485,657 B2 | 2/2009 | Cogan et al. |
| 7,511,042 B2 | 3/2009 | Cogan et al. |
| 7,514,458 B2 | 4/2009 | Cogan et al. |
| 7,531,560 B2 | 5/2009 | Cogan et al. |
| 7,569,568 B2 | 8/2009 | Cogan et al. |
| 7,858,804 B2 | 12/2010 | Frutos et al. |
| 8,198,308 B2 | 6/2012 | Steurer et al. |
| 2004/0102492 A1 | 5/2004 | Cogan et al. |
| 2005/0153972 A1 | 7/2005 | Cogan et al. |
| 2005/0256113 A1 | 11/2005 | Cogan et al. |
| 2006/0079519 A1 | 4/2006 | Cogan et al. |
| 2006/0100204 A1 | 5/2006 | Cogan et al. |
| 2007/0032492 A1 | 2/2007 | Cogan et al. |
| 2007/0142371 A1 | 6/2007 | Cogan et al. |
| 2008/0182837 A1 | 7/2008 | Steurer et al. |
| 2009/0127815 A1 | 5/2009 | Tani et al. |
| 2010/0240657 A1 | 9/2010 | Sapountzis et al. |
| 2011/0059938 A1 | 3/2011 | Steurer et al. |
| 2011/0183952 A1 | 7/2011 | Sapountzis et al. |
| 2011/0312939 A1 | 12/2011 | Steurer et al. |
| 2012/0046270 A1 | 2/2012 | Ettmayer et al. |
| 2012/0094975 A1 | 4/2012 | Mantoulidis et al. |

FOREIGN PATENT DOCUMENTS

| | | |
|---|---|---|
| CA | 2248316 A1 | 9/1997 |
| CA | 2248720 A1 | 9/1997 |
| EP | 837063 A1 | 4/1998 |
| EP | 1029853 A1 | 8/2000 |
| WO | 9519774 A1 | 7/1995 |
| WO | 9607657 A1 | 3/1996 |
| WO | 96/40142 A1 | 12/1996 |
| WO | 9732880 | 9/1997 |
| WO | 9732882 A1 | 9/1997 |
| WO | 9802437 A1 | 1/1998 |
| WO | 2004050642 A1 | 6/2004 |
| WO | 2005023761 A2 | 3/2005 |
| WO | 2005056535 A1 | 6/2005 |
| WO | 2005090333 A1 | 9/2005 |
| WO | 2005115991 A1 | 12/2005 |
| WO | 2007056016 A2 | 5/2007 |
| WO | 2007075896 A2 | 7/2007 |
| WO | 2008003770 A1 | 1/2008 |
| WO | 2008021388 A1 | 2/2008 |

(Continued)

OTHER PUBLICATIONS

International Search Report for PCT/EP2012/051281 mailed Mar. 13, 2012.

(Continued)

*Primary Examiner* — Jeffrey Murray
(74) *Attorney, Agent, or Firm* — Michael P. Morris; Edward S. Lazer

(57) ABSTRACT

The present invention encompasses compounds of general formula (1), wherein the groups $R^1$ to $R^4$, $X^1$, $X^2$, $X^3$, $X^4$, $X^5$, Q, $L^1$ and $L^2$ are defined as in claim 1, which are suitable for the treatment of diseases characterised by excessive or abnormal cell proliferation, as well as pharmaceutical preparations and formulations of these compounds.

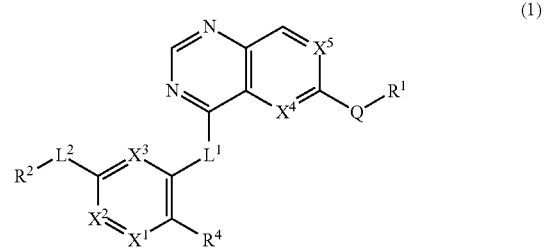

(1)

12 Claims, No Drawings

(56) References Cited

FOREIGN PATENT DOCUMENTS

| WO | 2008089034 | A2 | 7/2008 |
|---|---|---|---|
| WO | 2009003998 | A2 | 1/2009 |
| WO | 2009003999 | A2 | 1/2009 |
| WO | 2009012283 | A1 | 1/2009 |
| WO | 2010026262 | A1 | 3/2010 |
| WO | 2010034838 | A2 | 4/2010 |
| WO | 2010042337 | A1 | 4/2010 |
| WO | 2010094695 | A1 | 8/2010 |
| WO | 2011117381 | A1 | 9/2011 |
| WO | 2011117382 | A1 | 9/2011 |
| WO | 2012085127 | A1 | 6/2012 |
| WO | 2012101238 | A1 | 8/2012 |
| WO | 2012104388 | A1 | 8/2012 |

OTHER PUBLICATIONS

International Search Report, Form PCT/ISA/210, for corresponding PCT/EP2009/061656; date of mailing: Oct. 15, 2009.

Rewcastle, Gordon., et al; Tyrosine Kinase Inhibitors. 10. Isomeric 4-[(3-Bromophenyl)Amino]Pyrido[d]-Pyrimidines Are Potent ATP Binding Site Inhibitors of the Tyrosine Kinase Function of the Epidermal Growth Factor Receptor; Journal of Medicinal Chemistry (1996) vol. 39 pp. 1823-1835.

International Search Report for PCT/EP2010/051964 mailed May 12, 2010.

Rewcastle, Gordon, W., et al; Tyrosine Kinase Inhibitors. 14. Structure-Activity Relationshipsfor Methyl-amino-Substituted Derivatives of 4-[(3-Bromophenyl)amino]-6-(methylamino)-pyrido[3,4-d]pyrimidine (PD 158780), a Potent and Specific Inhibitor of the Tyrosine Kinase Activity of Receptors for the EGF Family of Growth Factors; Journal of Medicinal Chemistry (1998) vol. 41 pp. 742-751.

PYRIMIDO [5,4-D] PYRIMIDINE DERIVATIVES FOR THE INHIBITION OF TYROSINE KINASES

The present invention relates to new compounds of general formula (1)

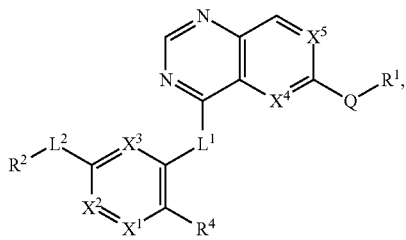

(1)

wherein the groups $R^1$ to $R^4$, $X^1$, $X^2$, $X^3$, $X^4$, $X^5$, Q, $L^1$ and $L^2$ have the meanings given in the claims and specification and the tautomers, racemates, enantiomers, diastereomers and mixtures and the salts of all these forms and their use as medicaments.

BACKGROUND TO THE INVENTION

Pyrimido[5,4-d]pyrimidines for inhibiting tyrosinekinases, which are involved in signal transduction, are described in WO 96/07657, WO 97/32880 and WO 97/32882.

The aim of the present invention is to indicate new active substances which can be used for the prevention and/or treatment of diseases characterised by excessive or abnormal cell proliferation.

DETAILED DESCRIPTION OF THE INVENTION

It has now been found that, surprisingly, compounds of general formula (1) wherein the groups $R^1$ to $R^4$, $X^1$, $X^2$, $X^3$, $X^4$, $X^5$, Q, $L^1$ and $L^2$ have the meanings given hereinafter act as inhibitors of specific signal enzymes which are involved in controlling cell proliferation. Thus, the compounds according to the invention may be used for example for the treatment of diseases connected with the activity of these signal enzymes and characterised by excessive or abnormal cell proliferation.

The present invention therefore relates to compounds of general formula (1)

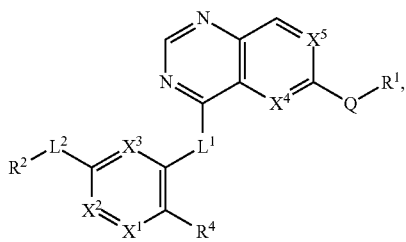

(1)

wherein $R^1$ is a group optionally substituted by one or more, identical or different $R^b$ and/or $R^c$, selected from among $C_{1-6}$alkyl, $C_{1-6}$haloalkyl, $C_{3-10}$cycloalkyl, $C_{6-10}$aryl, 5-12 membered heteroaryl and 3-14 membered heterocycloalkyl, or a suitable substituent, selected from among —$OR^c$, —$SR^c$, —$NR^cR^c$, —$NR^gNR^cR^c$ and —$S(O)R^c$;

$R^2$ is a group optionally substituted by one or more, identical or different $R^b$ and/or $R^c$, selected from among $C_{1-6}$alkyl, $C_{1-6}$haloalkyl, $C_{3-10}$cycloalkyl, $C_{6-10}$aryl, 5-12 membered heteroaryl and 3-14 membered heterocycloalkyl;

$R^4$ is selected from among hydrogen, —CN, —$NO_2$, —$NH_2$, —NH($C_{1-4}$alkyl), —N($C_{1-4}$alkyl)$_2$, $C_{1-4}$alkyl, $C_{1-4}$haloalkyl, $C_{1-4}$alkoxy, $C_{1-5}$cycloalkyl and halogen;

$X^1$, $X^2$ and $X^3$ are each independently of one another selected from among —N= and —$CR^{4*}$=,
while at most two of the atoms $X^1$, $X^2$ and $X^3$ may be nitrogen atoms and $R^{4*}$ is selected independently in each case from among hydrogen, —CN, —$NO_2$, —$NH_2$, —NH($C_{1-4}$alkyl), —N($C_{1-4}$alkyl)$_2$, $C_{1-4}$alkyl, $C_{1-4}$haloalkyl, $C_{1-4}$alkoxy, $C_{1-5}$cycloalkyl and halogen;

$X^4$ and $X^5$ are each selected from among —N= and —CH=,
wherein either $X^4$ or $X^5$ is a nitrogen atom;

$L^1$ is selected from among —$CH_2$—, —NH—, —NMe-, —O— and —S—;

$L^2$ is selected from among —C(O)NH—, —C(O)N($C_{1-4}$alkyl)-, —NHC(O)—, —N($C_{1-4}$alkyl)C(O)—, —$CH_2$—NHC(O)—, —C(O)—, —C(S)NH—, —NHC(S)—, —$NHCH_2$—, —$CH_2NH$—, —$S(O)_2NH$—, —$NHS(O)_2$—, —NHC(O)NH—, —OC(O)NH— and —NHC(O)O—,
while in the notation used above $L^2$ on the left binds to $R^2$;

Q denotes a bond or a methylene group;

each $R^b$ is a suitable substituent and is selected independently of one another from among —$OR^c$, —$SR^c$, —$NR^cR^c$, —$ONR^cR^c$, —N($OR^c$)$R^c$, —$NR^gNR^cR^c$, halogen, —CN, —$NO_2$, —$N_3$, —C(O)$R^c$, —C(O)$OR^c$, —C(O)$NR^cR^c$, —C(O)$NR^gNR^cR^c$, —C(O)$NR^gOR^c$, —C($NR^g$)$R^c$, —N=$CR^cR^c$, —C($NR^g$)$OR^c$, —C($NR^g$)$NR^cR^c$, —C($NR^g$)$NR^gNR^cR^c$, —C($NOR^g$)$R^c$, —C($NOR^g$)$NR^cR^c$, —C($NNR^gR^g$)$R^c$, —OS(O)$R^c$, —OS(O)$OR^c$, —OS(O)$NR^cR^c$, —OS(O)$_2R^c$, —OS(O)$_2OR^c$, —OS(O)$_2NR^cR^c$, —OC(O)$R^c$, —OC(O)$OR^c$, —OC(O)$NR^cR^c$, —OC($NR^g$)$R^c$, —OC($NR^g$)$NR^cR^c$, —$ONR^gC(O)R^c$, —S(O)$R^c$, —S(O)$OR^c$, —S(O)$NR^cR^c$, —S(O)$_2R^c$, —S(O)$_2OR^c$, —S(O)$_2NR^cR^c$, —$NR^gC(O)R^c$, —$NR^gC(O)OR^c$, —$NR^gC(O)NR^cR^c$, —$NR^gC(O)NR^gNR^cR^c$, —$NR^gC(NR^g)R^c$, —N=$CR^cNR^cR^c$, —$NR^gC(NR^g)OR^c$, —$NR^gC(NR^g)NR^cR^c$, —$NR^gC(NOR^g)R^c$, —$NR^gS(O)R^c$, —$NR^gS(O)OR^c$, —$NR^gS(O)_2R^c$, —$NR^gS(O)_2OR^c$, —$NR^gS(O)_2NR^cR^c$, —$NR^gNR^gC(O)R^c$, —$NR^gNR^gC(O)NR^cR^c$, —$NR^gNR^gC(NR^g)R^c$ and —N($OR^g$)C(O)$R^c$ and the bivalent substituents =O, =S, =$NR^g$, =$NOR^g$, =$NNR^gR^g$ and =$NNR^gC(O)NR^gR^g$, while these bivalent substituents may only be substituents in non-aromatic ring systems;

each $R^c$ independently denotes hydrogen or a group optionally substituted by one or more, identical or different $R^d$ and/or $R^e$, selected from among $C_{1-6}$alkyl, 2-6 membered heteroalkyl, $C_{1-6}$haloalkyl, $C_{3-10}$cycloalkyl, $C_{6-10}$aryl, 5-12 membered heteroaryl and 3-14 membered heterocycloalkyl;

each $R^d$ is a suitable substituent and is independently selected from among —$OR^e$, —$SR^e$, —$NR^eR^e$, —$ONR^eR^e$, —N($OR^e$)$R^e$, —N($R^g$)$NR^eR^e$, halogen, —CN, —NO, —$NO_2$, —$N_3$, —C(O)$R^e$, —C(O)$OR^e$, —C(O)$NR^eR^e$, —C(O)$NR^gNR^eR^e$, —C(O)$NR^gOR^e$, —C($NR^g$)$R^e$, —N=$CR^eR^e$, —C($NR^g$)$OR^e$, —C($NR^g$)$NR^eR^e$, —C($NR^g$)$NR^gNR^eR^e$, —C($NOR^g$)$R^e$, —C($NOR^g$)$NR^eR^e$, —C($NNR^gR^g$)$R^e$, —OS(O)$R^e$, —OS(O)$OR^e$, —OS(O)$NR^eR^e$, —OS(O)$_2R^e$, —OS(O)$_2OR^e$, —OS(O)$_2NR^eR^e$, —OC(O)$R^e$, —OC(O)$OR^e$, —OC(O)$NR^eR^e$, —OC($NR^g$)

$R^e$, —OC(NR$^g$)NR$^e$R$^e$, —ONR$^g$C(O)R$^e$, —S(O)R$^e$, —S(O)OR$^e$, —S(O)NR$^e$R$^e$, —S(O)$_2$R$^e$, —S(O)$_2$OR$^e$, —S(O)$_2$NR$^e$R$^e$, —NR$^g$C(O)R$^e$, —NR$^g$C(O)OR$^e$, —NR$^g$C(O)NR$^e$R$^e$, —NR$^g$C(O)NR$^g$NR$^e$R$^e$, —NR$^g$C(NR$^g$)R$^e$, —N=CR$^e$NR$^e$R$^e$, —NR$^g$C(NR$^g$)OR$^e$, —NR$^g$C(NR$^g$)NR$^e$R$^e$, —NR$^g$C(NR$^g$)SR$^e$, —NR$^g$C(NOR$^g$)R$^e$, —NR$^g$S(O)R$^e$, —NR$^g$S(O)OR$^e$, —NR$^g$S(O)$_2$R$^e$, —NR$^g$S(O)$_2$OR$^e$, —NR$^g$S(O)$_2$NR$^e$R$^e$, —NR$^g$NR$^g$C(O)R$^e$, —NR$^g$NR$^g$C(O)NR$^e$R$^e$, —NR$^g$NR$^g$C(NR$^g$)R$^e$ and —N(OR$^g$)C(O)R$^e$ and the bivalent substituents =O, =S, =NR$^g$, =NOR$^g$, =NNR$^g$R$^g$ and =NNR$^g$C(O)NR$^g$R$^g$, while these bivalent substituents may only be substituents in non-aromatic ring systems;

each R$^e$ independently denotes hydrogen or a group optionally substituted by one or more, identical or different R$^f$ and/or R$^g$, selected from among C$_{1-6}$alkyl, 2-6 membered heteroalkyl, C$_{1-6}$haloalkyl, C$_{3-10}$cycloalkyl, C$_{6-10}$aryl, 5-12 membered heteroaryl and 3-14 membered heterocycloalkyl;

each R$^f$ is a suitable substituent and is independently selected from among —OR$^g$, —SR$^g$, —NR$^g$R$^g$, —ONR$^g$R$^g$, —N(OR$^g$)R$^g$, —N(R$^h$)NR$^g$R$^g$, halogen, —CN, —NO$_2$, —N$_3$, —C(O)R$^g$, —C(O)OR$^g$, —C(O)NR$^g$R$^g$, —C(O)NR$^h$NR$^g$R$^g$, —C(O)NR$^h$OR$^g$, —C(NR$^h$)R$^g$, —N=CR$^g$R$^g$, —C(NR$^h$)OR$^g$, —C(NR$^h$)NR$^g$R$^g$, —C(NR$^h$)NR$^h$NR$^g$R$^g$, —C(NOR$^h$)R$^g$, —C(NOR$^h$)NR$^g$R$^g$, —C(NNR$^h$R$^h$)R$^g$, —OS(O)R$^g$, —OS(O)OR$^g$, —OS(O)NR$^g$R$^g$, —OS(O)$_2$R$^g$, —OS(O)$_2$OR$^g$, —OS(O)$_2$NR$^g$R$^g$, —OC(O)R$^g$, —OC(O)OR$^g$, —OC(O)NR$^g$R$^g$, —OC(NR$^h$)R$^g$, —OC(NR$^h$)NR$^g$R$^g$, —ONR$^h$C(O)R$^g$, —S(O)R$^g$, —S(O)OR$^g$, —S(O)NR$^g$R$^g$, —S(O)$_2$R$^g$, —S(O)$_2$OR$^g$, —S(O)$_2$NR$^g$R$^g$, —NR$^h$C(O)R$^g$, —NR$^h$C(O)OR$^g$, —NR$^h$C(O)NR$^g$R$^g$, —NR$^h$C(O)NR$^h$NR$^g$R$^g$, —NR$^h$C(NR$^h$)R$^g$, —N=CR$^g$NR$^g$R$^g$, —NR$^h$C(NR$^h$)OR$^g$, —NR$^h$C(NR$^h$)NR$^g$R$^g$, —NR$^h$C(NOR$^h$)R$^g$, —NR$^h$S(O)R$^g$, —NR$^h$S(O)OR$^g$, —NR$^h$S(O)$_2$R$^g$, —NR$^h$S(O)$_2$OR$^g$, —NR$^h$S(O)$_2$NR$^g$R$^g$, —NR$^h$NR$^h$C(O)R$^g$, —NR$^h$NR$^h$C(O)NR$^g$R$^g$, —NR$^h$NR$^h$C(NR$^h$)R$^g$ and —N(OR$^h$)C(O)R$^g$ and the bivalent substituents =O, =S, =NR$^h$, =NOR$^h$, =NNR$^h$R$^h$ and =NNR$^h$C(O)NR$^h$R$^h$, while these bivalent substituents may only be substituents in non-aromatic ring systems;

each R$^g$ independently denotes hydrogen or a group optionally substituted by one or more, identical or different R$^h$, selected from among C$_{1-6}$alkyl, 2-6 membered heteroalkyl, C$_{1-6}$haloalkyl, C$_{3-10}$cycloalkyl, C$_{6-10}$aryl, 5-12 membered heteroaryl and 3-14 membered heterocycloalkyl;

each R$^h$ is independently selected from among hydrogen, C$_{1-6}$alkyl, 2-6 membered heteroalkyl, C$_{1-6}$haloalkyl, C$_{3-10}$cycloalkyl, C$_{6-10}$aryl, 5-12 membered heteroaryl and 3-14 membered heterocycloalkyl;

while the compounds (1) may optionally also be in the form of the tautomers, racemates, enantiomers, diastereomers and mixtures thereof, or as respective pharmacologically acceptable salts of all the above-mentioned forms.

In one aspect the invention relates to compounds (1), wherein

R$^1$ is a group optionally substituted by one or more, identical or different R$^b$ and/or R$^c$, selected from among 5-12 membered heteroaryl and 3-14 membered heterocycloalkyl, and R$^b$ and R$^c$ are as hereinbefore defined.

In another aspect the invention relates to compounds (1), wherein

R$^1$ is a 3-7 membered, monocyclic and nitrogen-containing heterocycloalkyl or 6-10 membered, bicyclic and nitrogen-containing heterocycloalkyl optionally substituted by one or more, identical or different R$^b$ and/or R$^c$, R$^1$ binds to Q via a nitrogen atom, and R$^b$ and R$^c$ are as hereinbefore defined.

In another aspect the invention relates to compounds (1), wherein

R$^1$ is a 3-7 membered, monocyclic and nitrogen-containing heterocycloalkyl or 6-10 membered, bicyclic and nitrogen-containing heterocycloalkyl optionally substituted by one or more, identical or different R$^b$ and/or R$^c$, R$^1$ binds to Q via a carbon atom, and R$^b$ and R$^c$ are as hereinbefore defined.

In another aspect the invention relates to compounds (1), wherein

R$^1$ is a group optionally substituted by one or more, identical or different R$^b$ and/or R$^c$, selected from among piperidyl, perhydro-1,4-diazepinyl, piperazinyl, octahydro-pyrrolo[1,2-a]pyrazinyl, 2,5-diazabicyclo[2,2,1]heptyl, octahydro-pyrido[1,2-a]pyrazinyl, perhydro-1,4-oxazepinyl, morpholinyl, pyrrolidinyl, perhydroazepinyl, thiomorpholinyl, thiazolidinyl, imidazolidinyl and azetidinyl, and R$^b$ and R$^c$ are as hereinbefore defined.

In another aspect the invention relates to compounds (1), wherein the heteroaryl or heterocycloalkyl that binds directly to Q is substituted by one or more substituents, each independently selected from among R$^{b1}$ and R$^{c1}$;

each R$^{b1}$ is selected independently of one another from among —NR$^{c1}$R$^{c1}$, halogen, —C(O)R$^{c1}$ and =O, while the latter substituent may only be a substituent in non-aromatic ring systems, each R$^{c1}$ independently denotes hydrogen or a group optionally substituted by one or more, identical or different R$^{d1}$ and/or R$^{e1}$, selected from among C$_{1-6}$alkyl, C$_{3-10}$cycloalkyl, 5-12 membered heteroaryl and 3-14 membered heterocycloalkyl, each R$^{d1}$ corresponds to the group —OR$^{e1}$, each R$^{e1}$ independently denotes hydrogen or a group optionally substituted by one or more, identical or different C$_{1-6}$alkyl, selected from among C$_{1-6}$alkyl, C$_{3-10}$cycloalkyl and 3-14 membered heterocycloalkyl.

In another aspect the invention relates to compounds (1), wherein

R$^1$ is selected from among

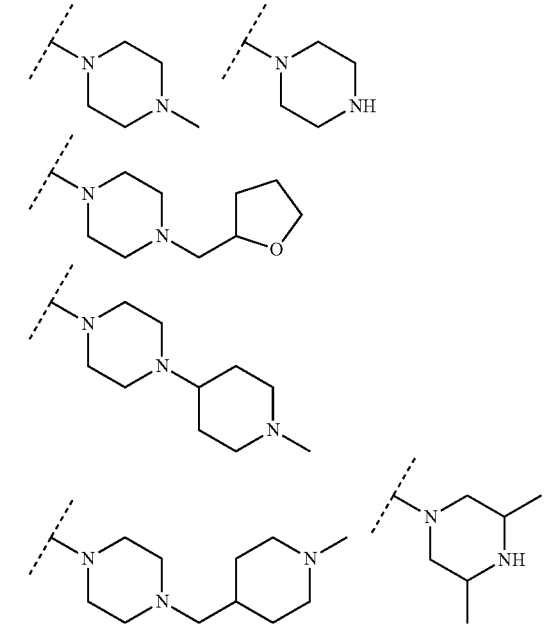

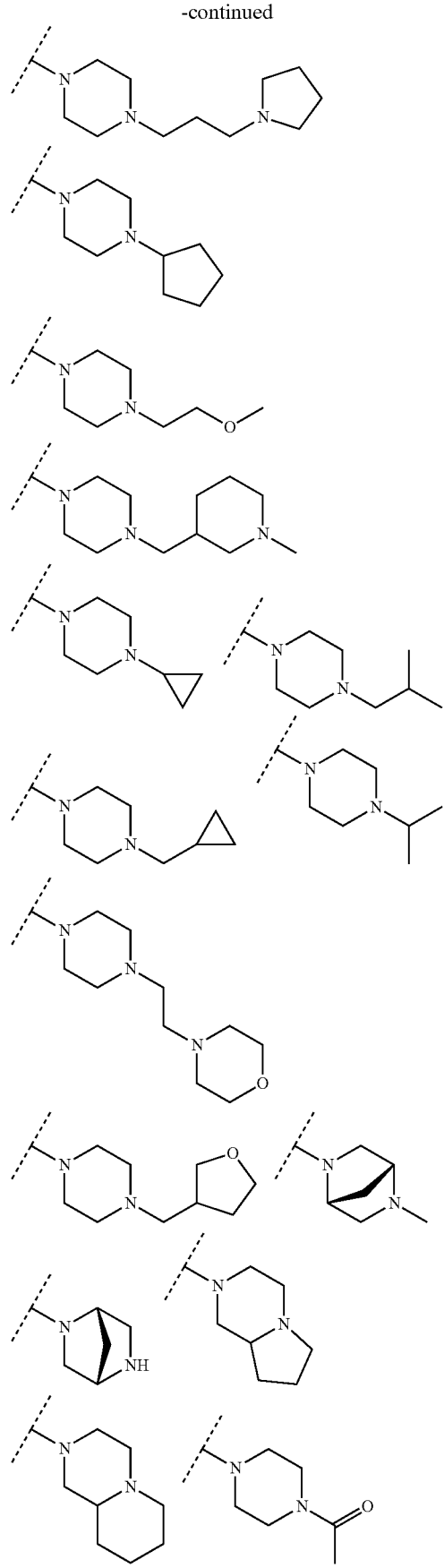
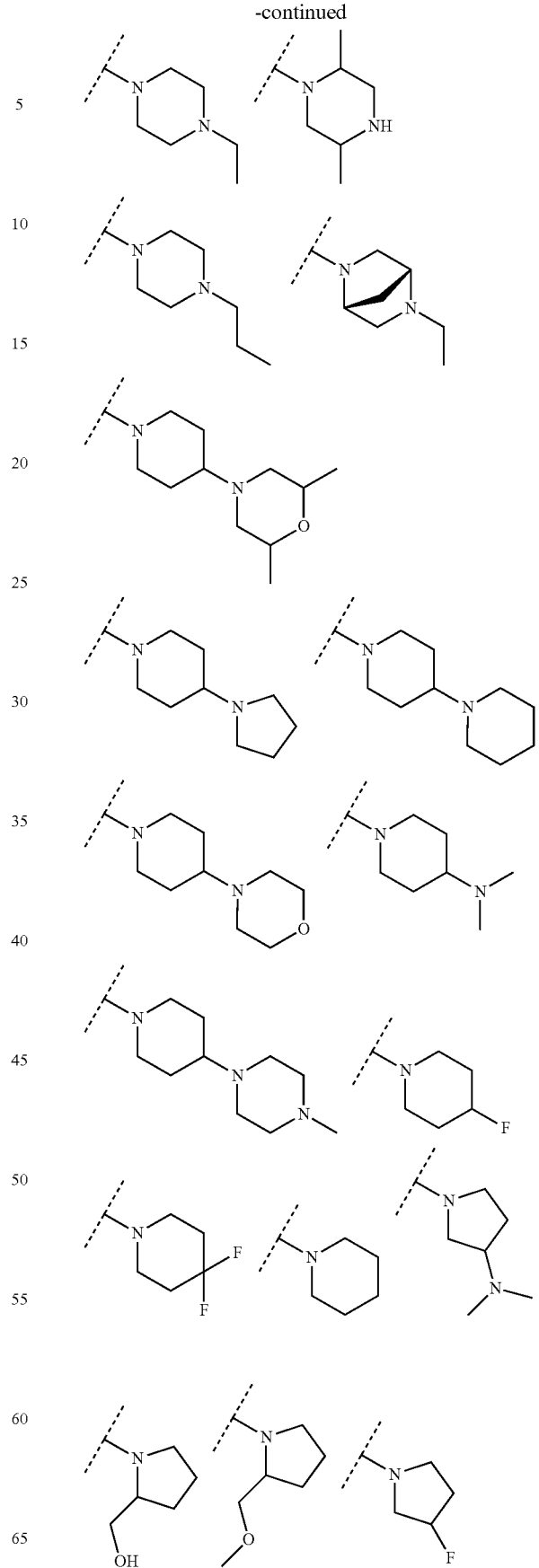

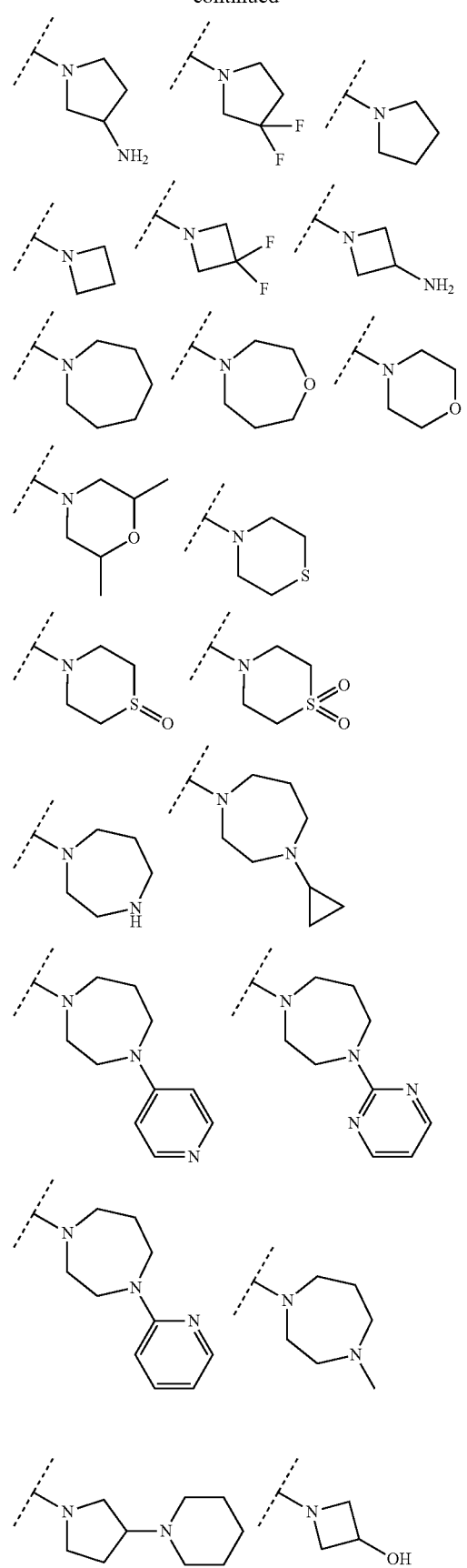
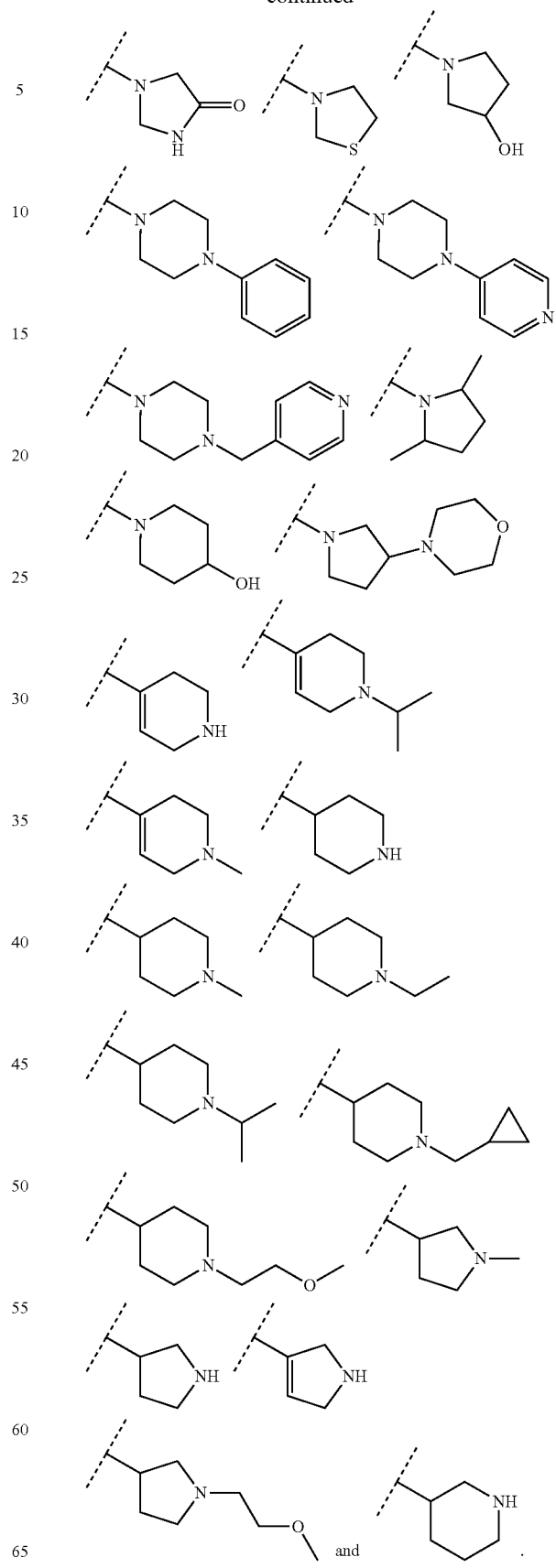

In another aspect the invention relates to compounds (1), wherein
$R^1$ is a $C_{6-10}$aryl, particularly phenyl, optionally substituted by one or more, identical or different $R^b$ and/or $R^c$, and $R^b$ and $R^c$ are as hereinbefore defined.

In another aspect the invention relates to compounds (1), wherein
Q denotes a bond.

In another aspect the invention relates to compounds (1), wherein
Q denotes a methylene group.

In another aspect the invention relates to compounds (1), wherein
-Q-$R^1$ is selected from among

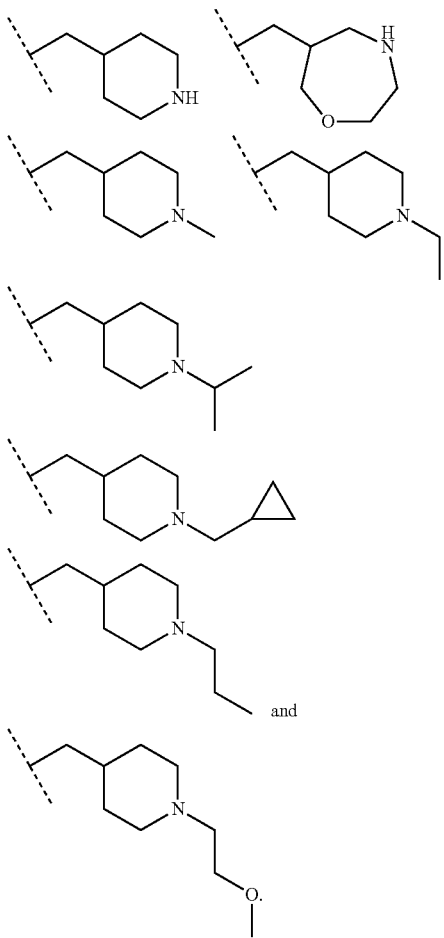

In another aspect the invention relates to compounds (1), wherein
$R^1$ denotes —$NR^{c2}R^{c3}$ and
$R^{c2}$ and $R^{c3}$ are each defined independently of one another as in $R^c$ hereinbefore.

In another aspect the invention relates to compounds (1), wherein
$R^{c2}$ is selected from among hydrogen, $C_{1-6}$alkyl, $C_{3-6}$cycloalkyl, phenyl, 5-6 membered heteroaryl and 3-7 membered heterocycloalkyl,
$R^{c3}$ is a group optionally substituted by one or more, identical or different $R^{d3}$ and/or $R^{e3}$, selected from among $C_{1-6}$alkyl, $C_{1-6}$haloalkyl, $C_{3-10}$cycloalkyl and 3-14 membered heterocycloalkyl,
each $R^{d3}$ is selected independently of one another from among halogen, —$NR^{e3}R^{e3}$ and —$OR^{e3}$,
each $R^{e3}$ is independently selected from among hydrogen, $C_{1-6}$alkyl, $C_{6-10}$aryl, 5-12 membered heteroaryl and 3-14 membered heterocycloalkyl.

In another aspect the invention relates to compounds (1), wherein
$R^{c2}$ is not hydrogen.

In another aspect the invention relates to compounds (1), wherein
$R^4$ denotes fluorine, chlorine or methyl.

In another aspect the invention relates to compounds (1), wherein
$X^1$ denotes $CR^{4*-1}$, $X^2$ denotes $CR^{4*-2}$ and $X^3$ denotes $CR^{4*-3}$ and
$R^{4*-1}$, $R^{4*-2}$ and $R^{4*-3}$ are each selected from among hydrogen, fluorine, chlorine and methyl and at least two of the groups $R^{4*-1}$, $R^{4*-2}$ and $R^{4*-3}$ denote hydrogen.

In another aspect the invention relates to compounds (1), wherein
$X^1$ denotes nitrogen, $X^2$ denotes $CR^{4*-2}$ and $X^3$ denotes $CR^{4*-3}$ and
$R^{4*-2}$ and $R^{4*-3}$ are each selected from among hydrogen, fluorine, chlorine and methyl and at least one of the groups $R^{4*-2}$ and $R^{4*-3}$ denotes hydrogen.

In another aspect the invention relates to compounds (1), wherein
$X^4$ denotes —N= and $X^5$ denotes —CH=.

In another aspect the invention relates to compounds (1), wherein
$X^4$ denotes —CH= and $X^5$ denotes —N=.

In another aspect the invention relates to compounds (1), wherein
$L^1$ denotes —NH— or —NMe-.

In another aspect the invention relates to compounds (1), wherein
$R^2$ is a group optionally substituted by one or more, identical or different $R^b$ and/or $R^c$, selected from among $C_{6-10}$aryl and 5-12 membered heteroaryl, and $R^b$ and $R^c$ are as hereinbefore defined.

In another aspect the invention relates to compounds (1), wherein
$R^2$ is a group optionally substituted by one or more, identical or different $R^b$ and/or $R^c$, selected from among phenyl and 5-6 membered heteroaryl, and $R^b$ and $R^c$ are as hereinbefore defined.

In another aspect the invention relates to compounds (1), wherein
$R^2$ is selected from among furyl, thienyl, pyrrolyl, oxazolyl, thiazolyl, isoxazolyl, isothiazolyl, pyrazolyl, imidazolyl, oxadiazolyl, thiadiazolyl, pyridyl and pyrimidyl, all the above-mentioned groups optionally being substituted by one or two substituents, each independently selected from among $C_{3-7}$cycloalkyl, phenyl, 4-7 membered heterocycloalkyl, methyl, ethyl, n-propyl, isopropyl, n-butyl, 1-methylpropyl, isobutyl, sec.-butyl, tert.-butyl, n-pentyl, 1-methylbutyl, 1-ethylpropyl, isopentyl, neopentyl, trifluoromethyl, difluoro-methyl, fluoromethyl, tert.-butoxy, trifluoromethoxy,

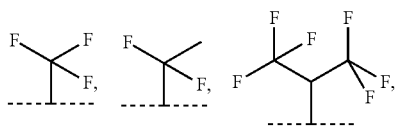

-continued

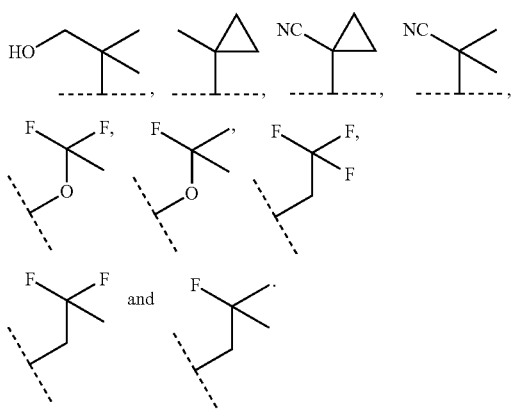

In another aspect the invention relates to compounds (1), wherein $R^2$ denotes a substituted phenyl

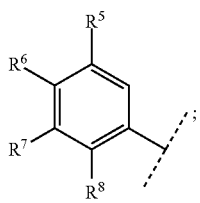

$R^5$ is selected from among hydrogen, $C_{1-6}$alkyl, —$OC_{1-6}$alkyl, $C_{1-6}$haloalkyl, —$OC_{1-6}$haloalkyl, $C_{3-7}$cycloalkyl and 3-7 membered heterocycloalkyl, all the above-mentioned groups optionally being substituted by $C_{1-6}$alkyl, —CN or —OH;

$R^6$ is selected from among hydrogen, $C_{1-6}$alkyl, —$OC_{1-6}$alkyl, $C_{1-6}$haloalkyl, —$OC_{1-6}$haloalkyl, —CN, —OH, halogen, —$NHC_{1-6}$alkyl and —$N(C_{1-6}$alkyl$)_2$, the latter two optionally being substituted in the alkyl moiety by a substituent —$N(C_{1-6}$alkyl$)_2$;

$R^7$ is selected from among hydrogen, —$OC_{1-6}$alkyl, halogen, —$NHS(O)_2C_{1-6}$alkyl, —$S(O)_2NH_2$, —$S(O)_2NHC_{1-6}$alkyl, —$S(O)_2N(C_{1-6}$alkyl$)_2$,

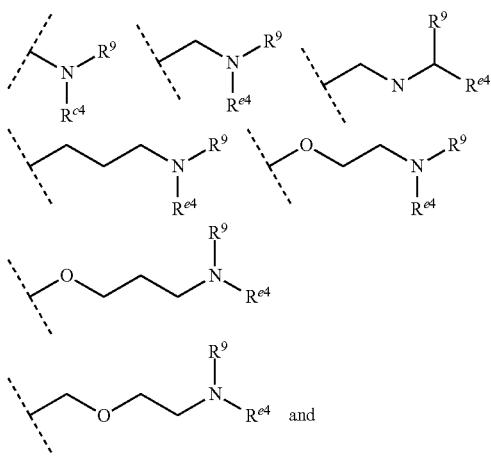

$R^9$ is selected from among hydrogen and $C_{1-6}$alkyl;

$R^{c4}$ denotes hydrogen or a group optionally substituted by one or more, identical or different $R^{d4}$ and/or $R^{e4}$, selected from among $C_{1-6}$alkyl and 3-14 membered heterocycloalkyl;

each $R^{d4}$ is a suitable substituent and is independently selected from among —$OR^{e4}$, —$NR^{e4}R^{e4}$ and halogen;

each $R^{e4}$ independently denotes hydrogen or a group optionally substituted by one or more, identical or different $R^{f4}$ and/or $R^{g4}$, selected from among $C_{1-6}$alkyl, $C_{1-6}$haloalkyl, $C_{3-10}$cycloalkyl, $C_{6-10}$aryl, 5-12 membered heteroaryl and 3-14 membered heterocycloalkyl;

each $R^{f4}$ is a suitable substituent and is independently selected from among —$OR^{g4}$, —$NR^{g4}R^{g4}$ and halogen as well as the bivalent substituent =O, which may only be a substituent in non-aromatic ring systems;

each $R^{g4}$ independently denotes hydrogen or a group optionally substituted by one or more, identical or different $R^{h4}$, selected from among $C_{1-6}$alkyl, $C_{3-10}$cycloalkyl, 5-12 membered heteroaryl and 3-14 membered heterocycloalkyl;

each $R^{h4}$ is selected independently of one another from among $C_{1-6}$alkyl and the bivalent substituent =O, which may only be a substituent in non-aromatic ring systems; or the group —$NR^9R^{c4}$ denotes a nitrogen-containing, 3-14 membered hetero-cycloalkyl or 5-12 membered heteroaryl, optionally substituted by one or more, identical or different group(s) selected from among $R^{d4}$ and $R^{e4}$;

the group —$NR^9R^{e4}$ denotes a nitrogen-containing, 3-14 membered hetero-cycloalkyl or 5-12 membered heteroaryl, optionally substituted by one or more, identical or different group(s) selected from among $R^{f4}$ and $R^{g4}$;

the group —$NR^9R^{g4}$ denotes a nitrogen-containing, 3-14 membered hetero-cycloalkyl or 5-12 membered heteroaryl, optionally substituted by one or more, identical or different group(s) $R^{h4}$;

$R^8$ is selected from among hydrogen, —$OC_{1-6}$alkyl, halogen, 5-12 membered hetero-aryl and 3-14 membered heterocycloalkyl.

In another aspect the invention relates to compounds (1), wherein at least one of the groups $R^5$ to $R^8$ is not equal to hydrogen and the other groups are as hereinbefore defined.

In another aspect the invention relates to compounds (1), wherein $R^5$ is selected from among

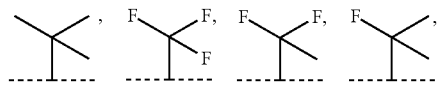

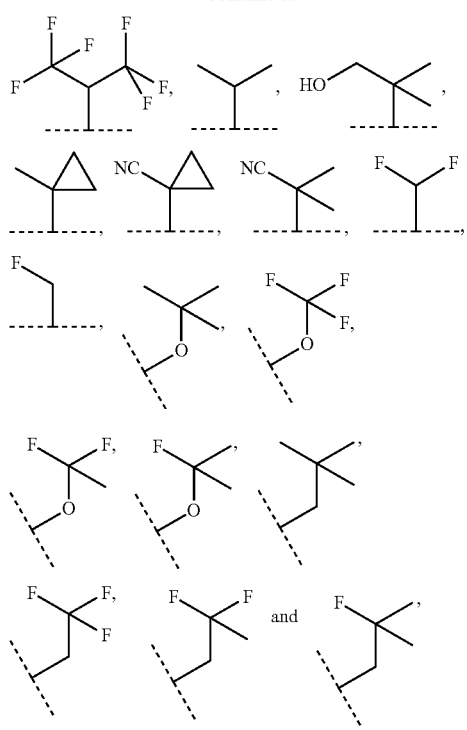
and the groups R⁶ to R⁸ are as hereinbefore defined.
In another aspect the invention relates to compounds (1), wherein
$R^2$ is selected from among
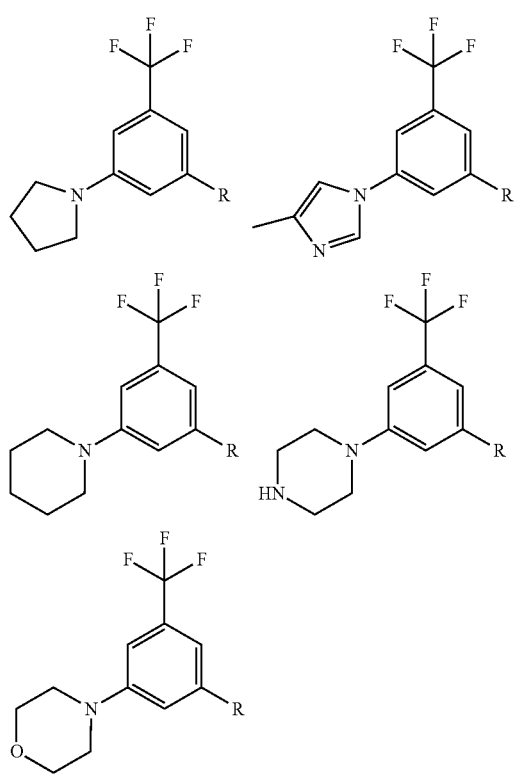
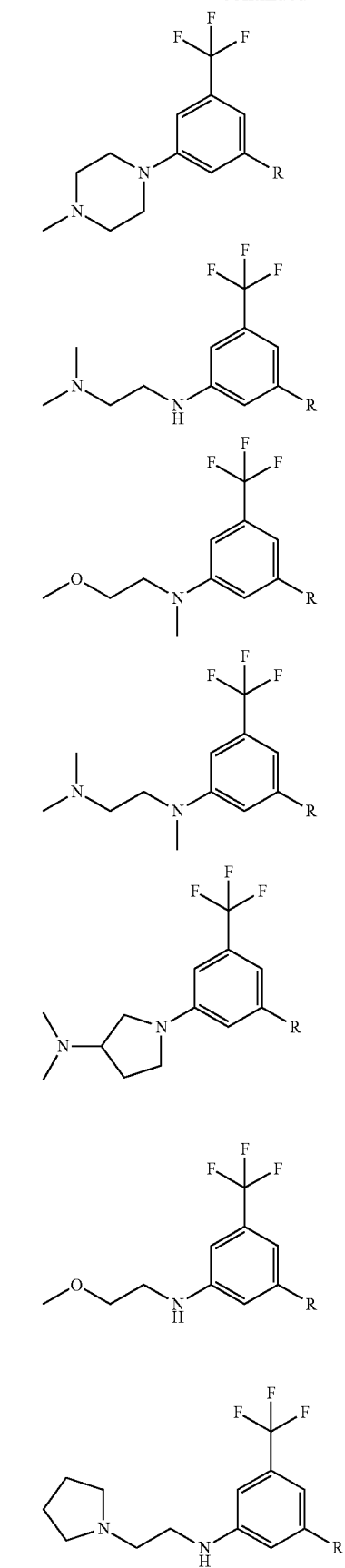

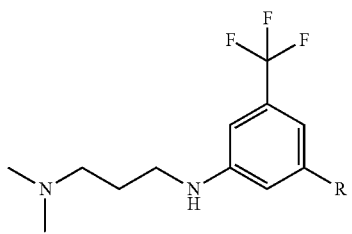
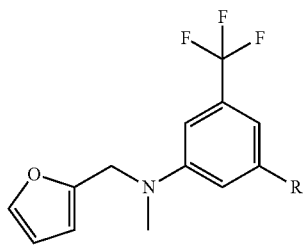
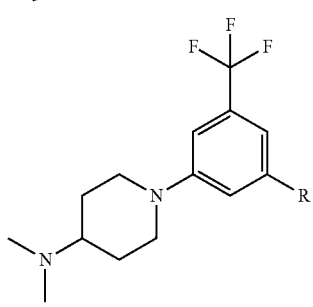
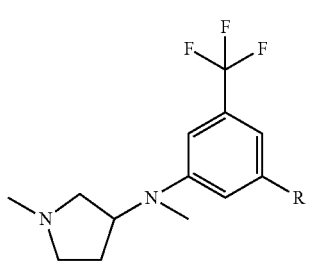
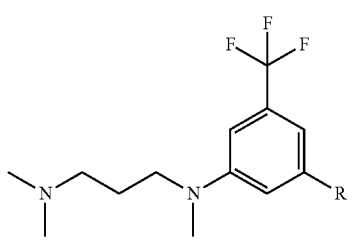
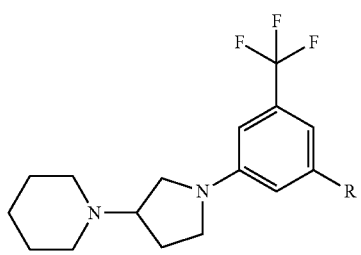
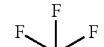
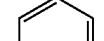
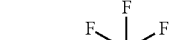
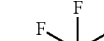
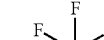
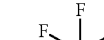

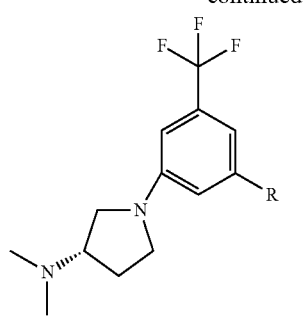
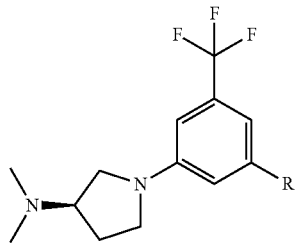
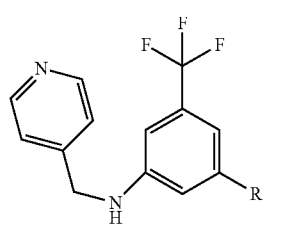
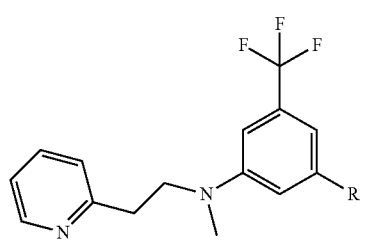
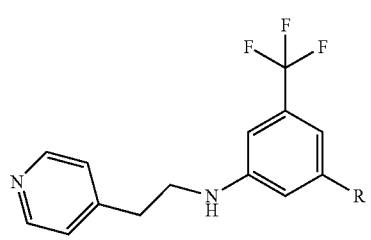
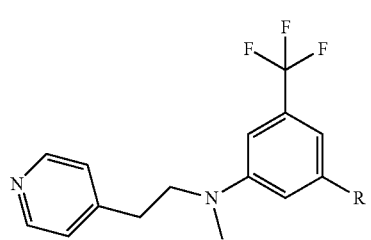
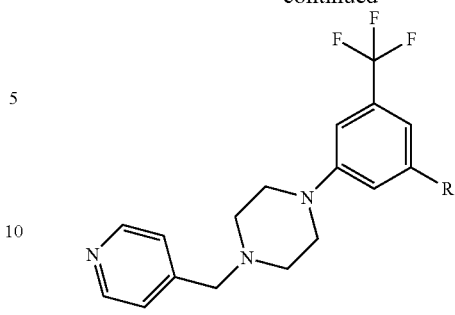
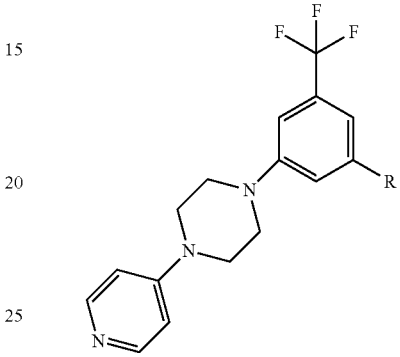
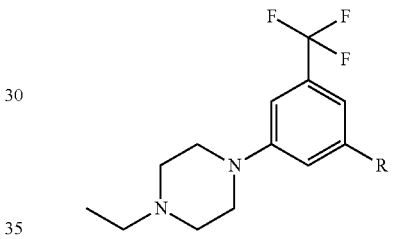
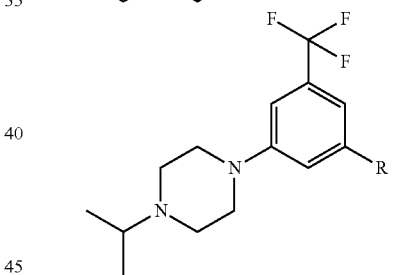
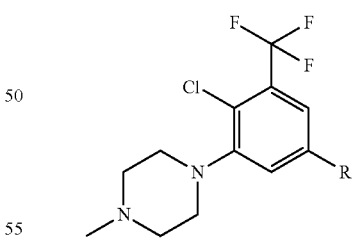
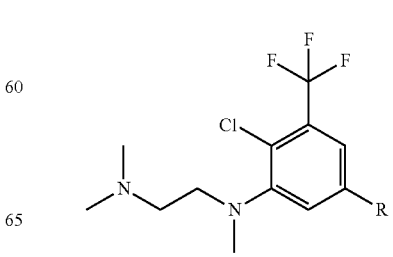

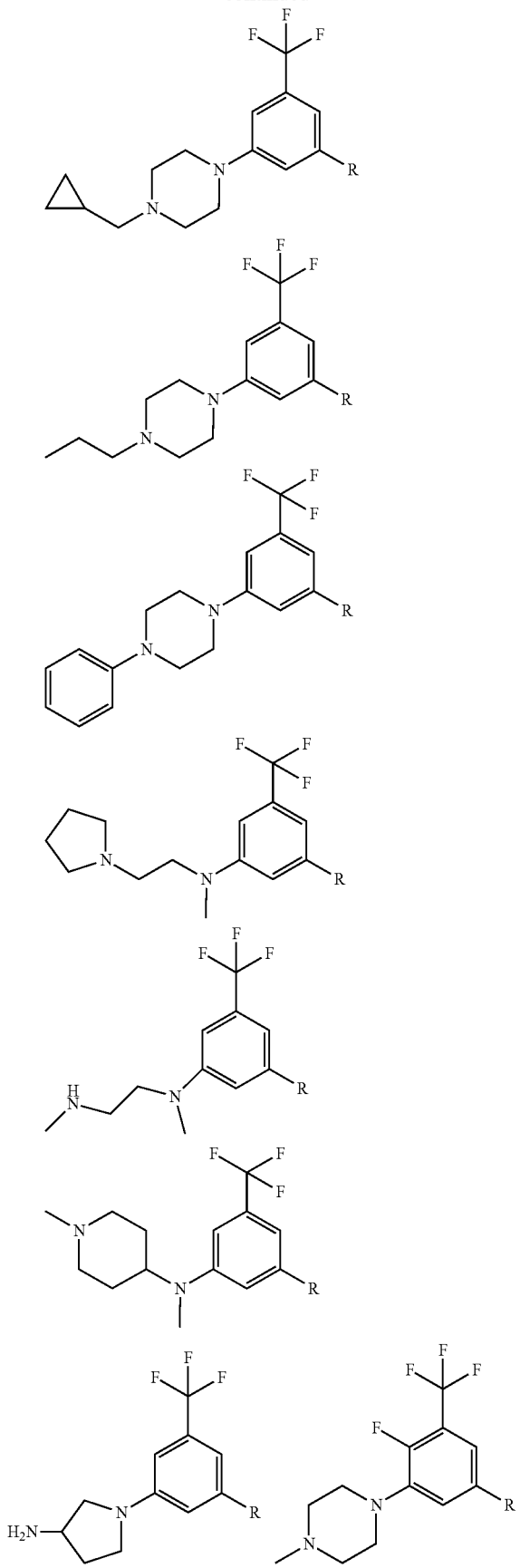
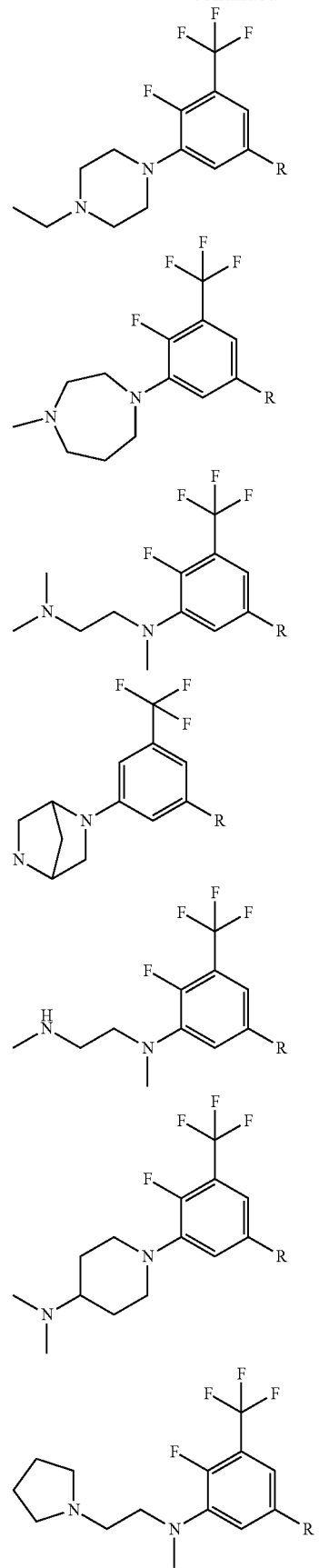

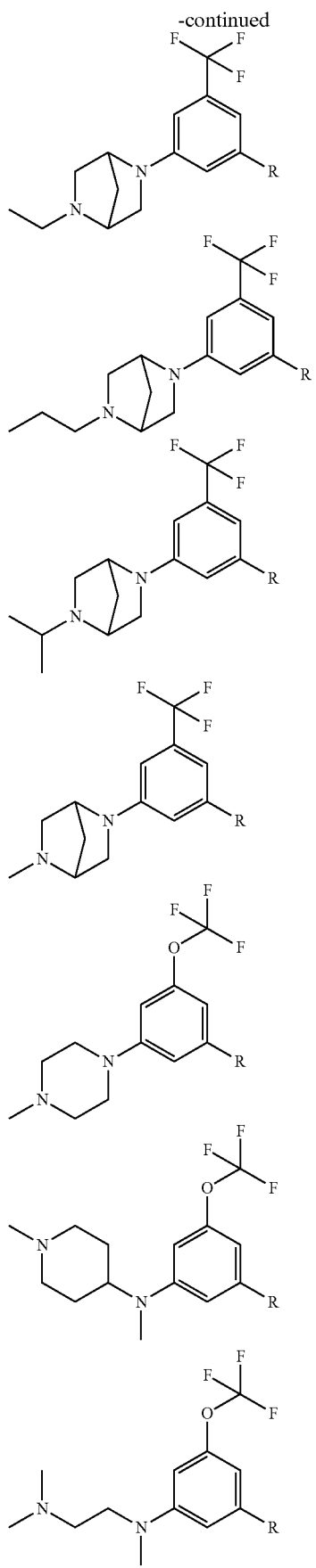
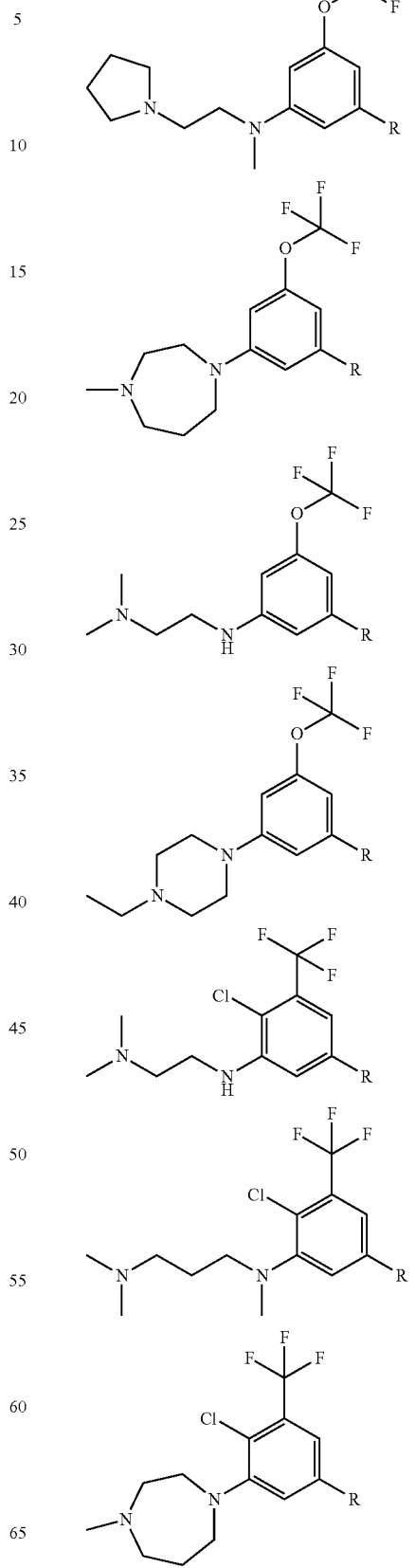

23
-continued
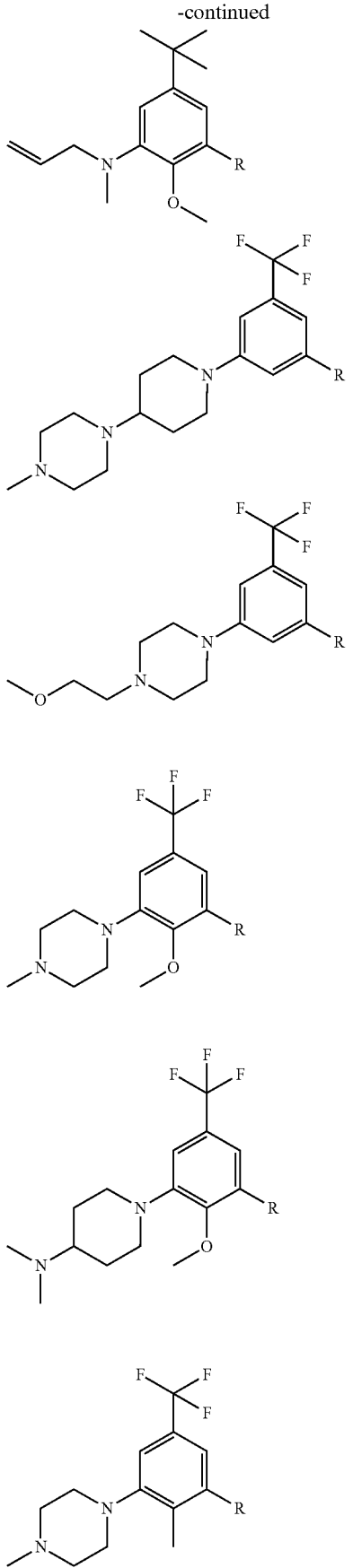
24
-continued
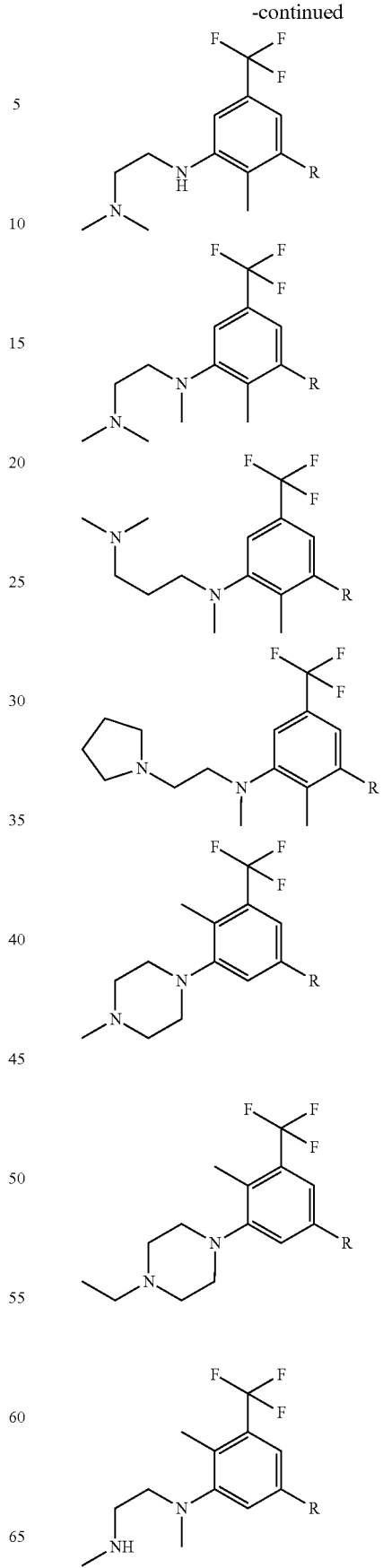

25
-continued
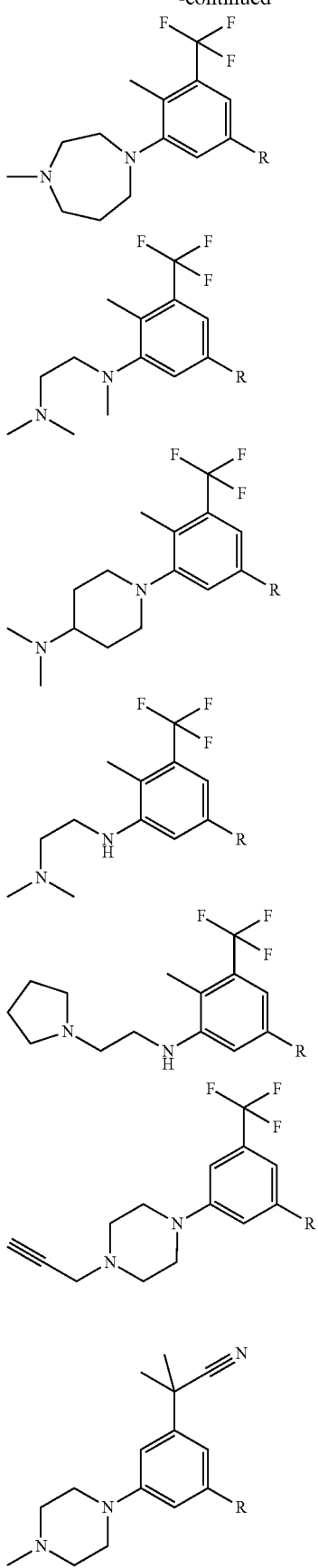
26
-continued
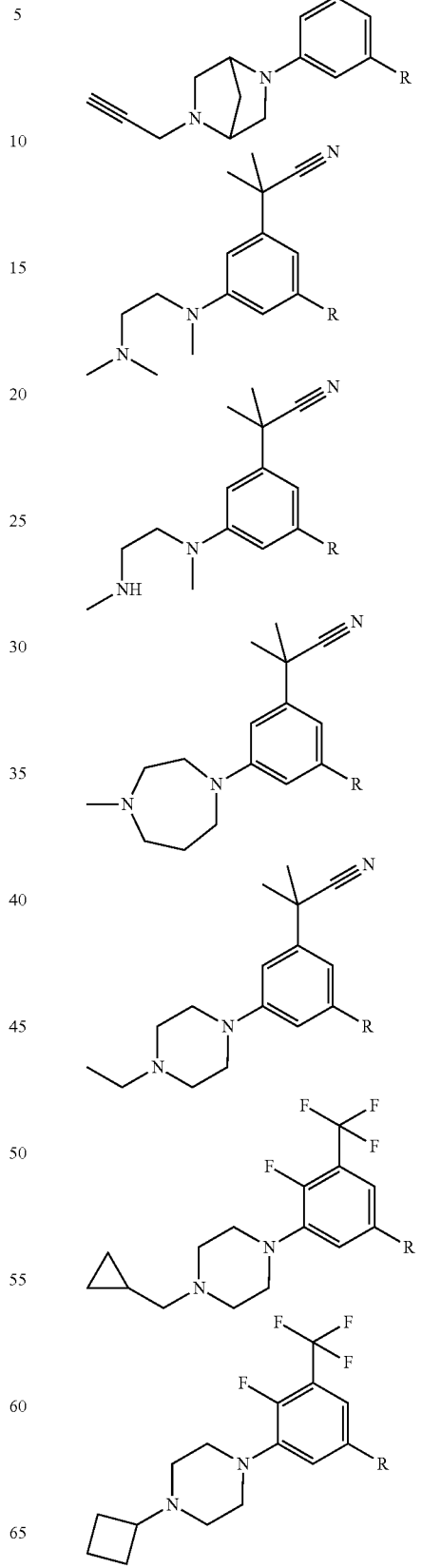

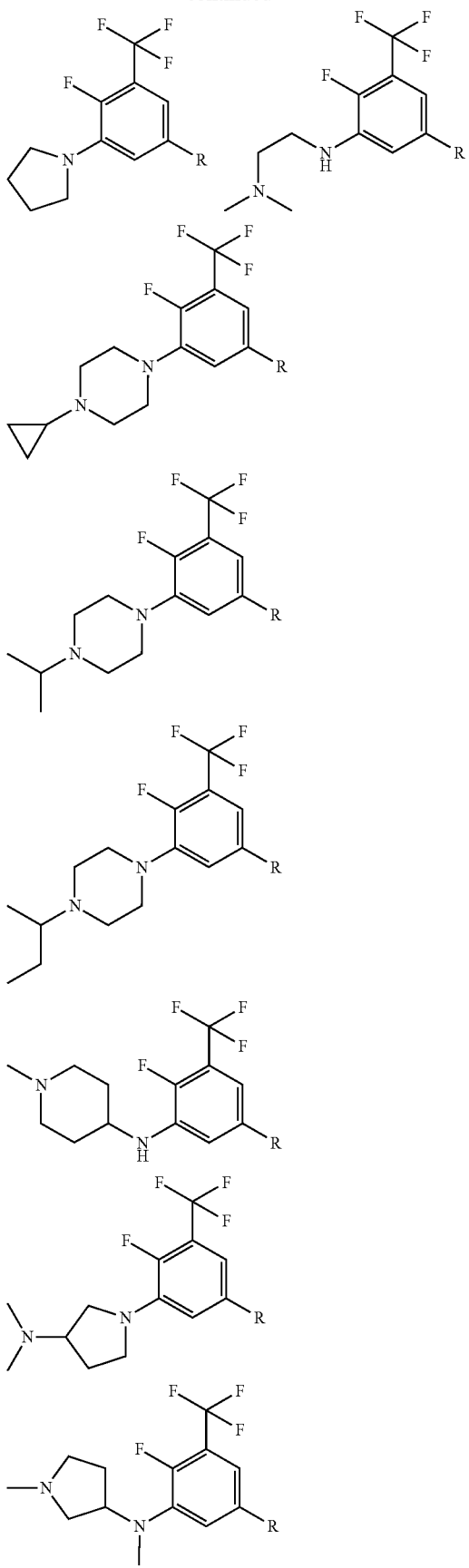
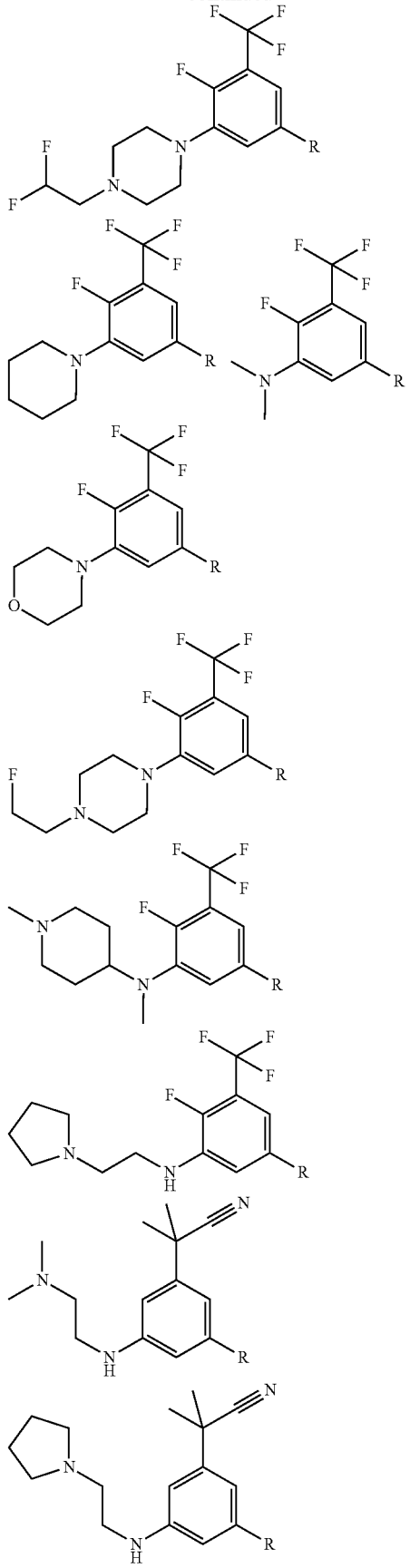

-continued
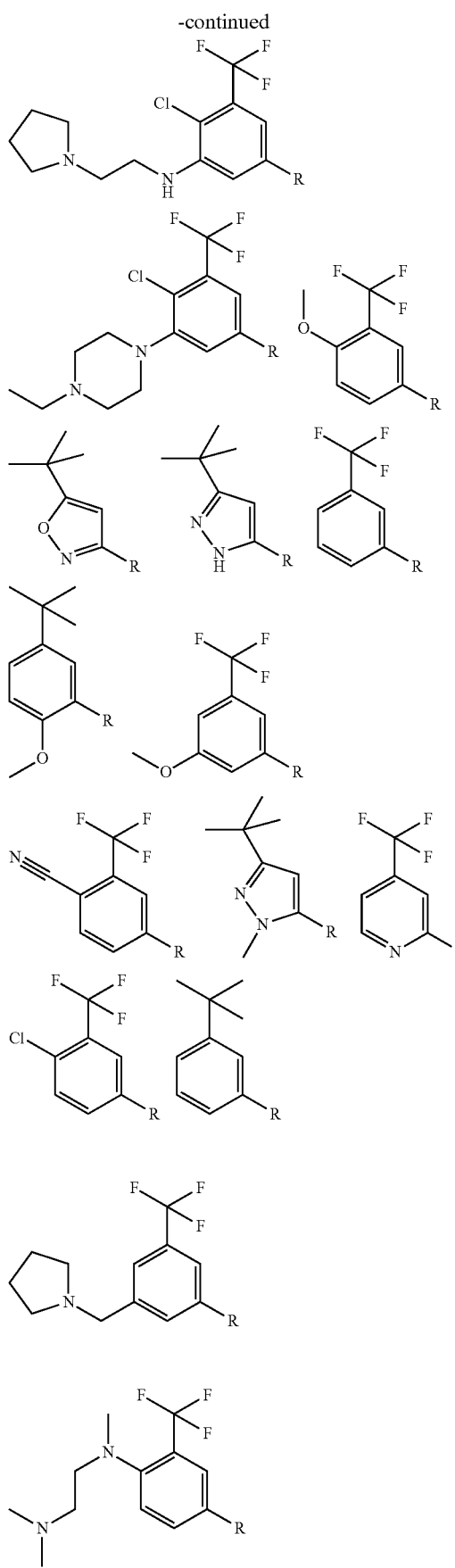
-continued
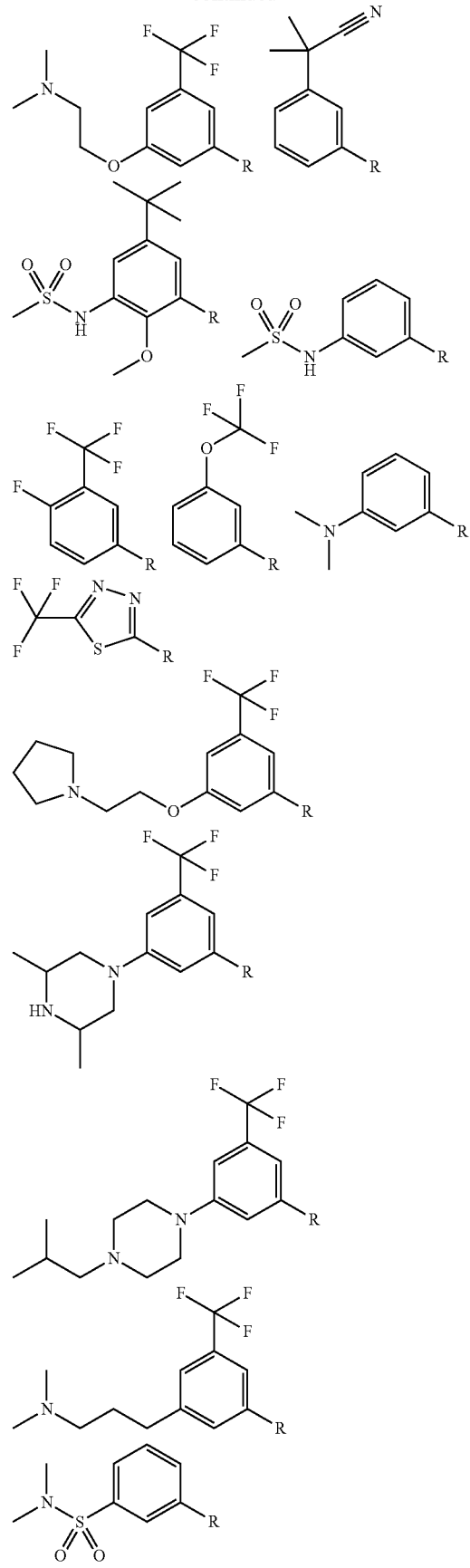

31
-continued
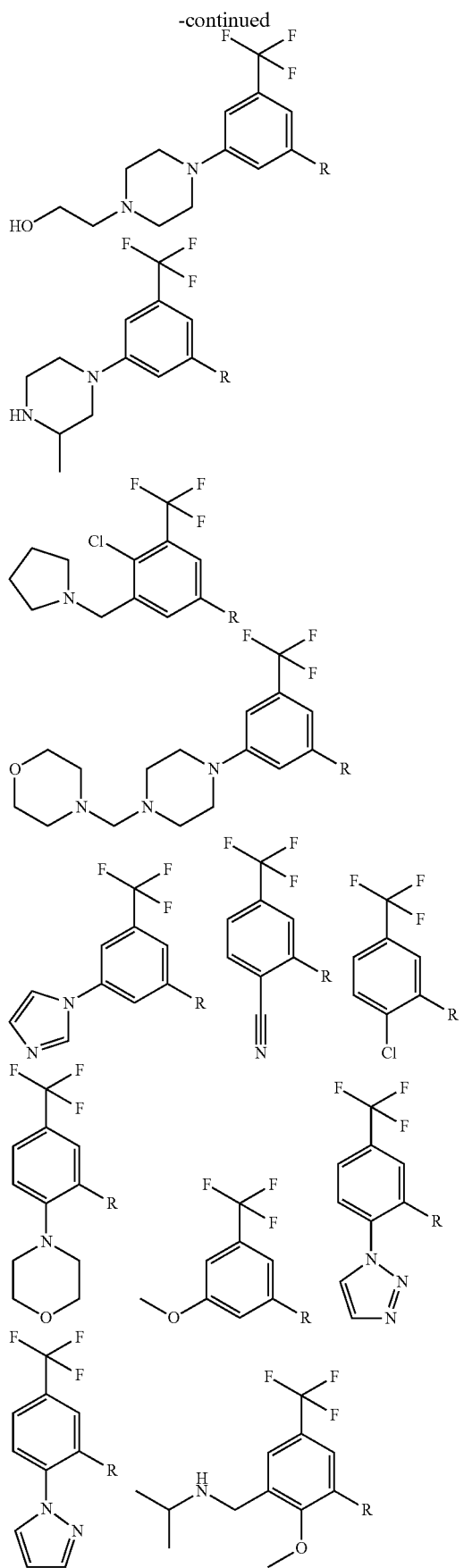
32
-continued
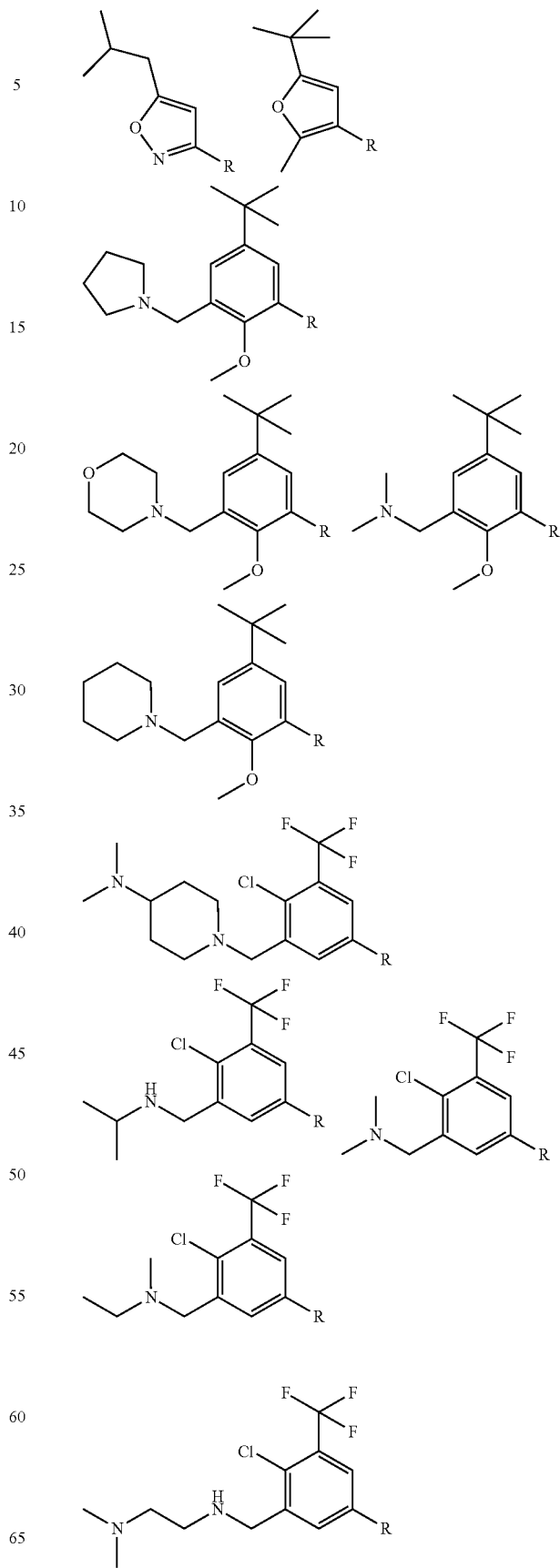

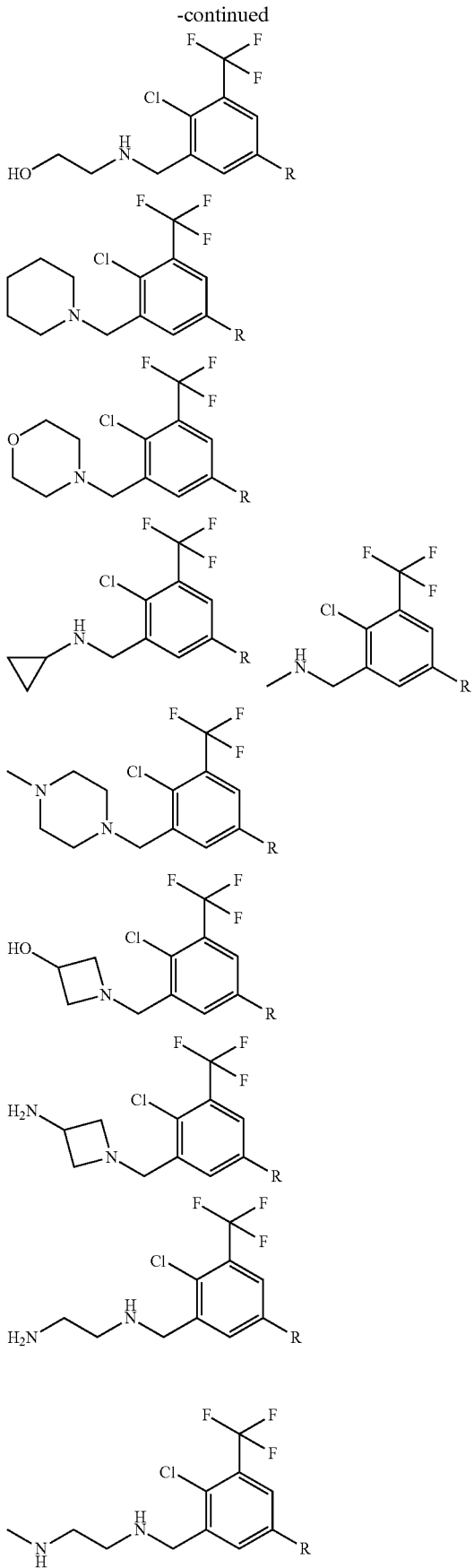

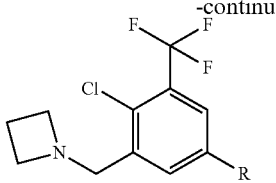

and R' denotes the binding site to the linker unit $L^2$.

In another aspect the invention relates to compounds (1), wherein $L^2$ denotes —C(O)NH—, while in the notation used above $L^2$ on the left binds to $R^2$ and $R^2$ is as hereinbefore defined.

In another aspect the invention relates to compounds (1), wherein $L^2$ denotes —NHC(O)—, while in the notation used above $L^2$ on the left binds to $R^2$ and $R^2$ is as hereinbefore defined.

In another aspect the invention relates to compounds (1), wherein each $R^b$ is a suitable substituent and is selected independently of one another from among —$OR^c$, —$NR^cR^c$, —$N(OR^c)R^c$, halogen, —CN, —$NO_2$, —$C(O)R^c$, —$C(O)OR^c$, —$C(O)NR^cR^c$, —$C(O)NR^gNR^cR^c$, —$C(O)NR^gOR^c$, —$S(O)_2R^c$, —$S(O)_2NR^cR^c$, —$NR^gC(O)R^c$, —$NR^gC(O)OR^c$, —$NR^gC(O)NR^cR^c$, —$NR^gS(O)_2R^c$ and the bivalent substituent =O, while this bivalent substituent may only be substituent in non-aromatic ring systems;

each $R^c$ independently denotes hydrogen or a group optionally substituted by one or more, identical or different $R^d$ and/or $R^e$, selected from among $C_{1-6}$alkyl, $C_{1-6}$haloalkyl, $C_{3-10}$cycloalkyl, $C_{6-10}$aryl, 5-12 membered heteroaryl and 3-14 membered heterocycloalkyl;

each $R^d$ is a suitable substituent and is independently selected from among —$OR^e$, —$NR^eR^e$, —$N(OR^e)R^e$, halogen, —CN, —$NO_2$, —$C(O)R^e$, —$C(O)OR^e$, —$C(O)NR^eR^e$, —$C(O)NR^gNR^eR^e$, —$C(O)NR^gOR^e$, —$S(O)_2R^e$, —$S(O)_2NR^eR^e$, —$NR^gC(O)R^e$, —$NR^gC(O)OR^e$, —$NR^gC(O)NR^eR^e$, —$NR^gS(O)_2R^e$ and the bivalent substituent =O, while this bivalent substituent may only be substituent in non-aromatic ring systems;

each $R^e$ independently denotes hydrogen or a group optionally substituted by one or more, identical or different $R^f$ and/or $R^g$, selected from among $C_{1-6}$alkyl, $C_{1-6}$haloalkyl, $C_{3-10}$cycloalkyl, $C_{6-10}$aryl, 5-12 membered heteroaryl and 3-14 membered heterocycloalkyl;

each $R^f$ is a suitable substituent and is independently selected from among —$OR^g$, —$NR^gR^g$, —$N(OR^g)R^g$, halogen, —CN, —$NO_2$, —$C(O)R^g$, —$C(O)OR^g$, —$C(O)NR^gR^g$, —$C(O)NR^hNR^gR^g$, —$C(O)NR^hOR^g$, —$S(O)_2R^g$, —$S(O)_2NR^gR^g$, —$NR^hC(O)R^g$, —$NR^hC(O)OR^g$, —$NR^hC(O)NR^gR^g$, —$NR^hS(O)_2R^g$ and the bivalent substituent =O, while this bivalent substituent may only be substituent in non-aromatic ring systems;

each $R^g$ independently denotes hydrogen or a group optionally substituted by one or more, identical or different $R^h$, selected from among $C_{1-6}$alkyl, $C_{1-6}$haloalkyl, $C_{3-10}$cycloalkyl, $C_{6-10}$aryl, 5-12 membered heteroaryl and 3-14 membered heterocycloalkyl and each $R^h$ is independently selected from among hydrogen, $C_{1-6}$alkyl, $C_{1-6}$haloalkyl, $C_{3-10}$cycloalkyl, $C_{6-10}$aryl, 5-12 membered heteroaryl and 3-14 membered heterocycloalkyl.

All the above-mentioned structural aspects relating to different molecular parts of the compounds (1) according to the invention may be combined with one another as desired, so as to obtain preferred compounds (1).

In another aspect the invention relates to compounds—or the pharmacologically acceptable salts thereof—of general formula (1) as medicaments.

In another aspect the invention relates to pharmaceutical preparations, containing as active substance one or more compounds of general formula (1) or the pharmacologically acceptable salts thereof, optionally in combination with conventional excipients and/or carriers.

In another aspect the invention relates to compounds of general formula (1)—or the pharmacologically acceptable salts thereof—for use in the treatment and/or prevention of cancer, infections, inflammations and autoimmune diseases.

In another aspect the invention relates to compounds of general formula (1)—or the pharmacologically acceptable salts thereof—for use in the treatment and/or prevention of cancer.

In another aspect the invention relates to compounds of general formula (1)—or the pharmacologically acceptable salts thereof—for use in the treatment and/or prevention of metastatic melanoma, colorectal carcinoma, thyroid tumors and gall bladder/bile duct tumors.

In another aspect the invention relates to a pharmaceutical preparation comprising a compound of general formula (1), while the compounds (1) may optionally also be present in the form of the tautomers, racemates, enantiomers, diastereomers and mixtures thereof or as the respective pharmacologically acceptable salts of all the above-mentioned forms, and at least one other cytostatic or cytotoxic active substance different from formula (1).

Definitions

As used herein, the following definitions apply, unless stated otherwise:

The use of the prefix $C_{x-y}$, where x and y in each case denote a natural number (x<y), indicates that the chain or cyclic structure or combination of chain and cyclic structure referred to and mentioned in direction connection may consist in total of a maximum of y and a minimum of x carbon atoms.

The information as to the number of members in groups containing one or more heteroatom(s) (heteroalkyl, heteroaryl, heteroarylalkyl, heterocycloalkyl, heterocycloalkylalkyl) refers to the total atomic number of all the ring members or chain members or the total of all the ring and chain members.

Alkyl is made up of the sub-groups saturated hydrocarbon chains and unsaturated hydrocarbon chains, while the latter may be further subdivided into hydrocarbon chains with a double bond (alkenyl) and hydrocarbon chains with a triple bond (alkynyl). Alkenyl contains at least one double bond, alkynyl at least one triple bond. If a hydrocarbon chain should have both at least one double bond and at least one triple bond, by definition it belongs to the alkynyl sub-group. All the above-mentioned sub-groups may be further subdivided into straight-chain (unbranched) and branched. If an alkyl is substituted, it may be mono- or polysubstituted independently of one another at all the hydrogen-carrying carbon atoms.

Examples of Individual Sub-Groups are Listed Below.

Straight-Chain (Unbranched) or Branched, Saturated Hydrocarbon Chains:

methyl; ethyl; n-propyl; isopropyl (1-methylethyl); n-butyl; 1-methylpropyl; isobutyl (2-methylpropyl); sec.-butyl (1-methylpropyl); tert.-butyl (1.1-dimethylethyl); n-pentyl; 1-methylbutyl; 1-ethylpropyl; isopentyl (3-methylbutyl); neopentyl (2,2-dimethyl-propyl); n-hexyl; 2,3-dimethylbutyl; 2,2-dimethylbutyl; 3,3-dimethylbutyl; 2-methyl-pentyl; 3-methylpentyl; n-heptyl; 2-methylhexyl; 3-methylhexyl; 2,2-dimethylpentyl; 2,3-dimethylpentyl; 2,4-dimethylpentyl; 3,3-dimethylpentyl; 2,2,3-trimethylbutyl; 3-ethylpentyl; n-octyl; n-nonyl; n-decyl etc.

Straight-Chained (Unbranched) or Branched Alkenyl:

vinyl (ethenyl); prop-1-enyl; allyl (prop-2-enyl); isopropenyl; but-1-enyl; but-2-enyl; but-3-enyl; 2-methyl-prop-2-enyl; 2-methyl-prop-1-enyl; 1-methyl-prop-2-enyl; 1-methyl-prop-1-enyl; 1-methylidenepropyl; pent-1-enyl; pent-2-enyl; pent-3-enyl; pent-4-enyl; 3-methyl-but-3-enyl; 3-methyl-but-2-enyl; 3-methyl-but-1-enyl; hex-1-enyl; hex-2-enyl; hex-3-enyl; hex-4-enyl; hex-5-enyl; 2,3-dimethyl-but-3-enyl; 2,3-dimethyl-but-2-enyl; 2-methylidene-3-methylbutyl; 2,3-dimethyl-but-1-enyl; hexa-1,3-dienyl; hexa-1,4-dienyl; penta-1,4-dienyl; penta-1,3-dienyl; buta-1,3-dienyl; 2,3-dimethylbuta-1,3-diene etc.

Straight-Chain (Unbranched) or Branched Alkynyl:

ethynyl; prop-1-ynyl; prop-2-ynyl; but-1-ynyl; but-2-ynyl; but-3-ynyl; 1-methyl-prop-2-ynyl etc.

By the terms propyl, butyl, pentyl, hexyl, heptyl, octyl, nonyl, decyl etc. Unless otherwise stated are meant saturated hydrocarbon groups with the corresponding number of carbon atoms, including all the isomeric forms.

By the terms propenyl, butenyl, pentenyl, hexenyl, heptenyl, octenyl, nonenyl, decenyl etc. unless otherwise stated are meant unsaturated hydrocarbon groups with the corresponding number of carbon atoms and a double bond, including all the isomeric forms, also (Z)/(E)-isomers, where applicable.

By the terms butadienyl, pentadienyl, hexadienyl, heptadienyl, octadienyl, nonadienyl, decadienyl etc. Unless otherwise stated are meant unsaturated hydrocarbon groups with the corresponding number of carbon atoms and two double bonds, including all the isomeric forms, also (Z)/(E)-isomers, where applicable.

By the terms propynyl, butynyl, pentynyl, hexynyl, heptynyl, octynyl, nonynyl, decynyl etc. Unless otherwise stated are meant unsaturated hydrocarbon groups with the corresponding number of carbon atoms and a triple bond, including all the isomeric forms.

From alkyl as hereinbefore defined and its subgroups the term alkylene can also be derived. Alkylene unlike alkyl is bivalent and requires two bonding partners. Formally the second valency is produced by removing a hydrogen atom from an alkyl. Corresponding groups are for example —CH$_3$ and —CH$_2$—, —CH$_2$CH$_3$ and —CH$_2$CH$_2$— or >CHCH$_3$ etc. For all the subgroups of alkyl there are correspondences for alkylene.

By heteroatoms are meant oxygen, nitrogen and sulphur atoms.

By the term heteroalkyl are meant groups which are derived from the alkyl as hereinbefore defined in its widest sense by replacing, in the hydrocarbon chains, one or more of the groups —CH$_3$ independently of one another by the groups —OH, —SH or —NH$_2$, one or more of the groups —CH$_2$— independently of one another by the groups —O—, —S— or —NH—, one or more of the groups >CH— by the group >N, one or more of the groups =CH— by the group =N, one or more of the groups =CH$_2$ by the group =NH or one or more of the groups ☐CH by the group ☐N, while a total of not more than three heteroatoms may be present in one heteroalkyl, there must be at least one carbon atom between two oxygen atoms and between two sulphur atoms or between one oxygen and one sulphur atom and the group as a whole must have chemical stability.

A direct result of the indirect definition/derivation from alkyl is that heteroalkyl is made up of the sub-groups saturated hydrocarbon chains with heteroatom(s), heteroalkenyl and heteroalkynyl, and it may be further subdivided into straight-chain (unbranched) and branched. If a heteroalkyl is substituted, it may be mono- or polysubstituted independently of one another at all the hydrogen-carrying oxygen, sulphur, nitrogen and/or carbon atoms. Heteroalkyl itself as a substituent may be attached to the molecule both through a carbon atom and through a heteroatom.

The following are listed by way of example:
dimethylaminomethyl; dimethylaminoethyl (1-dimethylaminoethyl; 2-dimethyl-aminoethyl); dimethylaminopropyl (1-dimethylaminopropyl, 2-dimethylaminopropyl, 3-dimethylamino-propyl); diethylaminomethyl; diethylaminoethyl (1-diethylaminoethyl, 2-diethylaminoethyl); diethylaminopropyl (1-diethylaminopropyl, 2-diethylamino-propyl, 3-diethylaminopropyl); diisopropylaminoethyl (1-diisopropylaminoethyl, 2-di-isopropylaminoethyl); bis-2-methoxyethylamino; [2-(dimethylamino-ethyl)-ethyl-amino]methyl; 3-[2-(dimethylamino-ethyl)-ethyl-amino]-propyl; hydroxymethyl; 2-hydroxy-ethyl; 3-hydroxypropyl; methoxy; ethoxy; propoxy; methoxymethyl; 2-methoxyethyl etc.

From heteroalkyl as hereinbefore defined and its subgroups the term heteroalkylene can also be derived. Heteroalkylene unlike heteroalkyl is bivalent and requires two bonding partners. Formally the second valency is produced by removing a hydrogen atom from a heteroalkyl. Corresponding groups are for example —CH$_2$NH$_2$ and —CH$_2$NH or >CHNH$_2$, —NHCH$_3$ and >NCH$_3$ or —NHCH$_2$, —CH$_2$OCH$_3$ and —CH$_2$OCH$_2$ or >CHOCH$_3$ etc. For all the subgroups of heteroalkyl there are correspondences for heteroalkylene.

Haloalkyl is derived from alkyl as hereinbefore defined in its broadest sense, by replacing one or more hydrogen atoms of the hydrocarbon chain independently of one another by halogen atoms, which may be identical or different. A direct result of the indirect definition/derivation from alkyl is that haloalkyl is made up of the sub-groups saturated hydro-halogen chains, haloalkenyl and haloalkynyl, and it may be further subdivided into straight-chain (unbranched) and branched. If a haloalkyl is substituted, it may be mono- or polysubstituted independently of one another at all the hydrogen-carrying carbon atoms.

Typical examples are listed below:
—CF$_3$; —CHF$_2$; —CH$_2$F; —CF$_2$CF$_3$; —CHFCF$_3$; —CH$_2$CF$_3$; —CF$_2$CH$_3$; —CHFCH$_3$; —CF$_2$CF$_2$CF$_3$; —CF$_2$CH$_2$CH$_3$; —CF=CF$_2$; —CCl=CH$_2$; —CBr=CH$_2$; —CI=CH$_2$; —C☐C—CF$_3$; —CHFCH$_2$CH$_3$; —CHFCH$_2$CF$_3$ etc.

From haloalkyl as hereinbefore defined and its subgroups the term haloalkylene can also be derived. Haloalkylene unlike haloalkyl is bivalent and requires two bonding partners. Formally the second valency is produced by removing a hydrogen atom from a haloalkyl. Corresponding groups are for example —CH$_2$F and —CHF, —CHFCH$_2$F and —CHFCHF or >CFCH$_2$F etc. For all the subgroups of haloalkyl there are correspondences for haloalkylene.

Halogen encompasses fluorine, chlorine, bromine and/or iodine atoms.

Cycloalkyl is made up of the sub-groups monocyclic hydrocarbon rings, bicyclic hydrocarbon rings and spirohydrocarbon rings, while each sub-group may be further subdivided into saturated and unsaturated (cycloalkenyl). By unsaturated is meant that there is at least one double bond in the ring system, but no aromatic system is formed. In bicyclic hydrocarbon rings two rings are linked such that they share at least two carbon atoms. In spirohydrocarbon rings one carbon atom (spiroatom) is shared by two rings. If a cycloalkyl is substituted, it may be mono- or polysubstituted independently of one another at all the hydrogen-carrying carbon atoms. Cycloalkyl itself as a substituent may be attached to the molecule through any suitable position of the ring system.

The following individual sub-groups are listed by way of example:
Monocyclic Hydrocarbon Rings, Saturated:
cyclopropyl; cyclobutyl; cyclopentyl; cyclohexyl; cycloheptyl etc.

Monocyclic Hydrocarbon Rings, Unsaturated:
cycloprop-1-enyl; cycloprop-2-enyl; cyclobut-1-enyl; cyclobut-2-enyl; cyclopent-1-enyl; cyclopent-2-enyl; cyclopent-3-enyl; cyclohex-1-enyl; cyclohex-2-enyl; cyclohex-3-enyl; cyclohept-1-enyl; cyclohept-2-enyl; cyclohept-3-enyl; cyclohept-4-enyl; cyclobuta-1,3-dienyl; cyclopenta-1,4-dienyl; cyclopenta-1,3-dienyl; cyclopenta-2,4-dienyl; cyclohexa-1,3-dienyl; cyclohexa-1,5-dienyl; cyclohexa-2,4-dienyl; cyclohexa-1,4-dienyl; cyclohexa-2,5-dienyl etc.

Bicyclic Hydrocarbon Rings (Saturated and Unsaturated):
bicyclo[2.2.0]hexyl; bicyclo[3.2.0]heptyl; bicyclo[3.2.1]octyl; bicyclo[2.2.2]octyl; bicyclo[4.3.0]nonyl (octahydroindenyl); bicyclo[4.4.0]decyl (decahydronaphthalene); bicyclo[2.2.1]heptyl (norbornyl); (bicyclo[2.2.1]hepta-2,5-dienyl (norborna-2,5-dienyl); bicyclo[2.2.1]hept-2-enyl (norbornenyl); bicyclo[4.1.0]heptyl (norcaranyl); bicyclo-[3.1.1]heptyl (pinanyl) etc.

Spirohydrocarbon Rings (Saturated and Unsaturated):
spiro[2.5]octyl, spiro[3.3]heptyl, spiro[4.5]dec-2-ene, etc.

If the free valency of a cycloalkyl is saturated off, an alicyclic ring is obtained.

From cycloalkyl as hereinbefore defined and its subgroups the term cycloalkylene can also be derived. Cycloalkylene unlike cycloalkyl is bivalent and requires two bonding partners. Formally the second valency is produced by removing a hydrogen atom from a cycloalkyl. Corresponding groups are for example cyclohexyl and

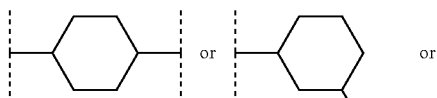

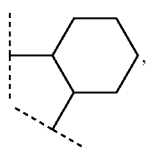

cyclopentenyl and

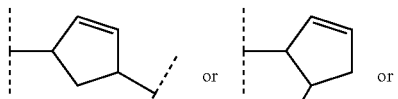

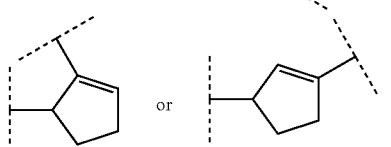

etc.

For all the subgroups of cycloalkyl there are correspondences for cycloalkylene.

Cycloalkylalkyl refers to the combination of the alkyl in question, as hereinbefore defined, with cycloalkyl, both in their widest sense. Alternatively cycloalkylalkyl may also be regarded as a combination of cycloalkyl with alkylene. Formally, cycloalkylalkyl is obtained by first linking an alkyl as substituent directly with the molecule and then substituting with a cycloalkyl. The linking of alkyl and cycloalkyl may be carried out in both groups using carbon atoms that are suitable for this purpose. The respective subgroups of alkyl (alkylene) and cycloalkyl are also included in the combination of the two groups.

Aryl denotes mono-, bi- or tricyclic carbon rings with at least one aromatic ring. If an aryl is substituted, the substitution may be mono- or polysubstitution in each case, at all the hydrogen-carrying carbon atoms, independently of one another. Aryl itself may be linked to the molecule as substituent via any suitable position of the ring system.

Typical examples are listed below:

phenyl, naphthyl, indanyl (2,3-dihydroindenyl), 1,2,3,4-tetrahydronaphthyl; fluorenyl, etc.

If the free valency of an aryl is saturated off, an aromatic group is obtained.

From aryl as hereinbefore defined the term arylene can also be derived. Arylene unlike aryl is bivalent and requires two bonding partners. Formally the second valency is produced by removing a hydrogen atom from an aryl. Corresponding groups are for example phenyl and

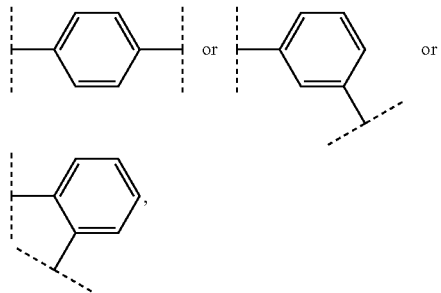

naphthyl and

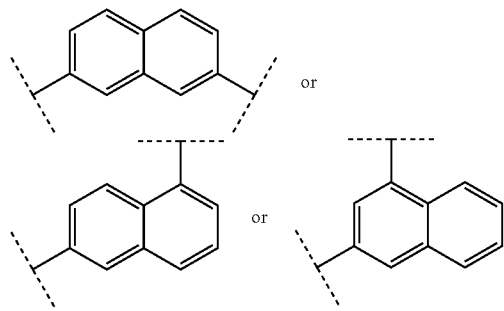

etc.

For all the subgroups of aryl there are correspondences for arylene.

Arylalkyl denotes the combination of the groups alkyl and aryl as hereinbefore defined, in each case in their broadest sense. Alternatively arylalkyl may also be regarded as a combination of aryl with alkylene. Formally, arylalkyl is obtained by first linking an alkyl as substituent directly to the molecule and substituting it with an aryl group. The alkyl and aryl may be linked in both groups via any carbon atoms suitable for this purpose. The respective sub-groups of alkyl (alkylene) and aryl are also included in the combination of the two groups.

Typical examples are listed below:

benzyl; 1-phenylethyl; 2-phenylethyl; phenylvinyl; phenylallyl etc.

Heteroaryl denotes monocyclic aromatic rings or polycyclic rings with at least one aromatic ring, which, compared with corresponding aryl or cycloalkyl, contain instead of one or more carbon atoms one or more identical or different heteroatoms, selected independently of one another from among nitrogen, sulphur and oxygen, while the resulting group must be chemically stable. The prerequisite for the presence of heteroaryl is a heteroatom and an aromatic system, although it need not necessarily be a heteroaromatic system. Thus 2,3-dihydro-1H-indol-6-yl

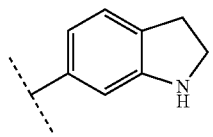

may according to the definition be a heteroaryl.

If a heteroaryl is substituted, the substitution may be mono- or polysubstitution in each case, at all the hydrogen-carrying carbon and/or nitrogen atoms, independently of one another. Heteroaryl itself as substituent may be linked to the molecule via any suitable position of the ring system, both carbon and nitrogen.

Typical examples are listed below.

Monocyclic Heteroaryls:

furyl; thienyl; pyrrolyl; oxazolyl; thiazolyl; isoxazolyl; isothiazolyl; pyrazolyl; imidazolyl; triazolyl; tetrazolyl; oxadiazolyl; thiadiazolyl; pyridyl; pyrimidyl; pyridazinyl; pyrazinyl; triazinyl; pyridyl-N-oxide; pyrrolyl-N-oxide; pyrimidinyl-N-oxide; pyridazinyl-N-oxide; pyrazinyl-N-oxide; imidazolyl-N-oxide; isoxazolyl-N-oxide; oxazolyl-N-oxide; thiazolyl-N-oxide; oxadiazolyl-N-oxide; thiadiazolyl-N-oxide; triazolyl-N-oxide; tetrazolyl-N-oxide etc.

Polycyclic Heteroaryls indolyl; isoindolyl; benzofuryl; benzothienyl; benzoxazolyl; benzothiazolyl; benzisoxazolyl; dihydroindolyl; benzisothiazolyl; benzimidazolyl; indazolyl; isoquinolinyl; quinolinyl; quinoxalinyl; cinnolinyl; phthalazinyl; quinazolinyl; benzotriazinyl; indolizinyl; oxazolopyridyl; imidazopyridyl; naphthyridinyl; indolinyl; isochromanyl; chromanyl; tetrahydroisoquinolinyl; isoindolinyl; isobenzotetrahydrofuryl; isobenzotetrahydrothienyl; isobenzothienyl; benzoxazolyl; pyridopyridyl; benzotetrahydrofuryl; benzotetrahydro-thienyl; purinyl; benzodioxolyl; phenoxazinyl; phenothiazinyl; pteridinyl; benzothiazolyl; imidazopyridyl; imidazothiazolyl; dihydrobenzisoxazinyl; benzisoxazinyl; benzoxazinyl; dihydrobenzisothiazinyl; benzopyranyl; benzothiopyranyl; coumarinyl; isocoumarinyl; chromonyl; chromanonyl; tetrahydroquinolinyl; dihydroquinolinyl; dihydroquinolinonyl; dihydroisoquinolinonyl; dihydrocoumarinyl; dihydroisocoumarinyl; isoindolinonyl; benzodioxanyl; benzoxazolinonyl; quinolinyl-N-oxide; indolyl-N-oxide; indolinyl-N-oxide; isoquinolyl-N-oxide; quinazolinyl-N-oxide; quinoxalinyl-N-oxide; phthalazinyl-N-oxide; indolizinyl-N-oxide; indazolyl-N-oxide; benzothiazolyl-N-oxide; benzimidazolyl-N-oxide; benzothiopyranyl-S-oxide and benzothiopyranyl-S,S-dioxide etc.

If the free valency of a heteroaryl is saturated off, a heteroaromatic group is obtained.

From heteroaryl as hereinbefore defined the term heteroarylene can also be derived. Heteroarylene unlike heteroaryl is bivalent and requires two bonding partners. Formally the second valency is produced by removing a hydrogen atom from a heteroaryl.

Corresponding groups are for example pyrrolyl and

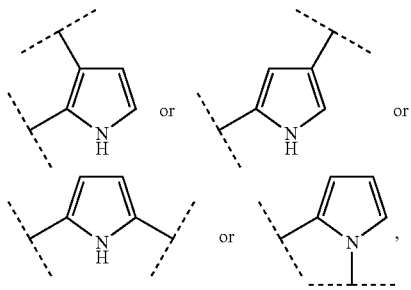

2,3-dihydro-1H-indolyl and

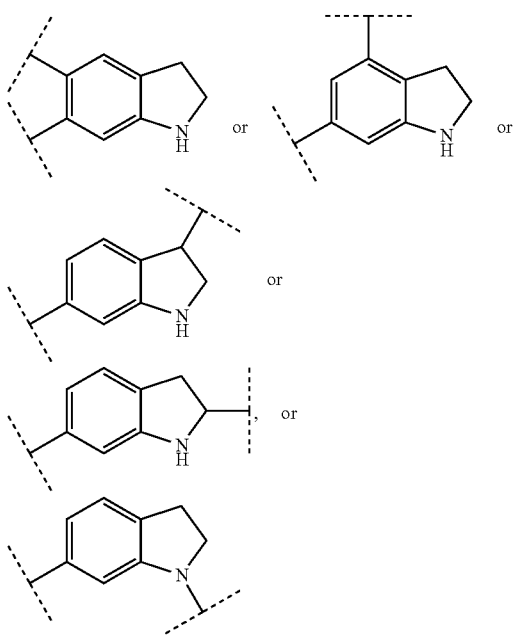

etc.

For all the subgroups of heteroaryl there are correspondences for heteroarylene.

Heteroarylalkyl denotes the combination of the alkyl in question as hereinbefore defined with heteroaryl, both in their broadest sense. Alternatively heteroarylalkyl may also be regarded as a combination of heteroaryl with alkylene. Formally heteroarylalkyl is obtained by first linking an alkyl as substituent directly with the molecule and then substituting it with a heteroaryl. The linking of the alkyl and heteroaryl may be achieved on the alkyl side via any carbon atoms suitable for this purpose and on the heteroaryl side via any carbon or nitrogen atoms suitable for this purpose. The respective subgroups of alkyl (alkylene) and heteroaryl are also included in the combination of the two groups.

By the term heterocycloalkyl are meant groups which are derived from the cycloalkyl as hereinbefore defined if in the hydrocarbon rings one or more of the groups —CH$_2$— are replaced independently of one another by the groups —O—, —S— or —NH— or one or more of the groups =CH— are replaced by the group =N—, while not more than five heteroatoms may be present in total, there must be at least one carbon atom between two oxygen atoms and between two sulphur atoms or between one oxygen and one sulphur atom and the group as a whole must be chemically stable. Heteroatoms may simultaneously be present in all the possible oxidation stages (sulphur→sulphoxide —SO—, sulphone —SO$_2$—; nitrogen→N-oxide). It is immediately apparent from the indirect definition/derivation from cycloalkyl that heterocycloalkyl is made up of the sub-groups monocyclic hetero-rings, bicyclic hetero-rings and spirohetero-rings, while each sub-group can also be further subdivided into saturated and unsaturated (heterocycloalkenyl). The term unsaturated means that in the ring system in question there is at least one double bond, but no aromatic system is formed. In bicyclic hetero-rings two rings are linked such that they have at least two atoms in common. In spirohetero-rings one carbon atom (spiroatom) is shared by two rings. If a heterocycloalkyl is substituted, the substitution may be mono- or polysubstitution in each case, at all the hydrogen-carrying carbon and/or nitrogen atoms, independently of one another. Heterocycloalkyl itself as substituent may be linked to the molecule via any suitable position of the ring system.

Typical examples of individual sub-groups are listed below.

Monocyclic Heterorings (Saturated and Unsaturated):

tetrahydrofuryl; pyrrolidinyl; pyrrolinyl; imidazolidinyl; thiazolidinyl; imidazolinyl; pyrazolidinyl; pyrazolinyl; piperidinyl; piperazinyl; oxiranyl; aziridinyl; azetidinyl; 1,4-dioxanyl; azepanyl; diazepanyl; morpholinyl; thiomorpholinyl; homomorpholinyl; homopiperidinyl; homopiperazinyl; homothiomorpholinyl; thiomorpholinyl-5-oxide; thiomorpholinyl-S,S-dioxide; 1,3-dioxolanyl; tetrahydropyranyl; tetrahydrothiopyranyl; [1,4]-oxazepanyl; tetrahydrothienyl; homothiomorpholinyl-S,S-dioxide; oxazolidinonyl; dihydropyrazolyl; dihydropyrrolyl; dihydropyrazinyl; dihydropyridyl; dihydro-pyrimidinyl; dihydrofuryl; dihydropyranyl; tetrahydrothienyl-S-oxide; tetrahydrothienyl-S,S-dioxide; homothiomorpholinyl-S-oxide; 2,3-dihydroazet; 2H-pyrrolyl; 4H-pyranyl; 1,4-dihydro-pyridinyl etc.

Bicyclic Heterorings (Saturated and Unsaturated):

8-azabicyclo[3.2.1]octyl; 8-azabicyclo[5.1.0]octyl; 2-oxa-5-azabicyclo[2.2.1]heptyl; 8-oxa-3-aza-bicyclo[3.2.1]octyl; 3,8-diaza-bicyclo[3.2.1]octyl; 2,5-diaza-bicyclo-[2.2.1]heptyl; 1-aza-bicyclo[2.2.2]octyl; 3,8-diaza-bicyclo[3.2.1]octyl; 3,9-diaza-bicyclo[4.2.1]nonyl; 2,6-diaza-bicyclo[3.2.2]nonyl etc.

Spiro-Heterorings (Saturated and Unsaturated):

1,4-dioxa-spiro[4.5]decyl; 1-oxa-3.8-diaza-spiro[4.5]decyl; and 2,6-diaza-spiro[3.3]heptyl; 2,7-diaza-spiro[4.4]nonyl; 2,6-diaza-spiro[3.4]octyl; 3,9-diaza-spiro[5.5]undecyl; 2,8-diaza-spiro[4.5]decyl etc.

If the free valency of a heterocycloalkyl is saturated off, then a heterocyclic ring is obtained.

From heterocycloalkyl as hereinbefore defined the term heterocycloalkylene can also be derived. Heterocycloalkylene unlike heterocycloalkyl is bivalent and requires two bonding partners. Formally the second valency is produced by removing a hydrogen atom from a heterocycloalkyl. Corresponding groups are for example piperidinyl and

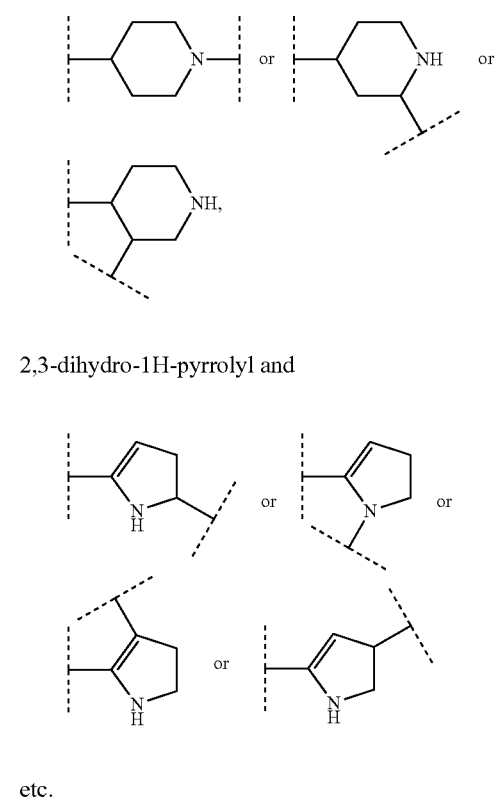

2,3-dihydro-1H-pyrrolyl and etc.

For all the subgroups of heterocycloalkyl there are correspondences for heterocycloalkylene.

Heterocycloalkylalkyl denotes the combination of the alkyl in question as hereinbefore defined with heterocycloalkyl, both in their broadest sense. Alternatively heterocyclo-alkylalkyl may also be regarded as a combination of heterocycloalkyl with alkylene. Formally heterocycloalkyl is obtained by first linking an alkyl as substituent directly with the molecule and then substituting it with a heterocycloalkyl. The linking of the alkyl and heterocycloalkyl may be achieved on the alkyl side via any carbon atoms suitable for this purpose and on the heterocycloalkyl side via any carbon or nitrogen atoms suitable for this purpose. The respective sub-groups of alkyl and heterocycloalkyl are also included in the combination of the two groups.

By is substituted is meant that a hydrogen atom that is bound directly to the atom under consideration is replaced by another atom or another group of atoms (substituent). Depending on the starting conditions (number of hydrogen atoms) mono- or polysubstitution may take place at an atom.

Bivalent substituents such as for example =S, =NR, =NOR, =NNRR, =NN(R)C(O)NRR, =N$_2$ or the like may only be substituents at carbon atoms, while the bivalent substituent =O may also be a substituent of sulphur. Generally speaking, substitution by a bivalent substituent may only take place at ring systems and requires exchange for two geminal hydrogen atoms, i.e. hydrogen atoms that are bound to the same carbon atom saturated before the substitution. Substitution by a bivalent substituent is therefore only possible at the group —CH$_2$— or sulphur atoms of a ring system.

In addition to this, the term "suitable substituent" denotes a substituent which on the one hand is suitable on account of its valency and on the other hand leads to a system with chemical stability.

The following are some abbreviated notations and their structural correspondences:

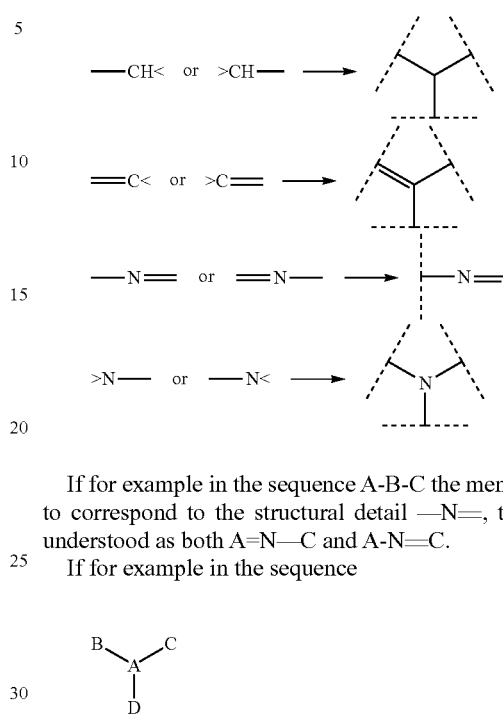

If for example in the sequence A-B-C the member B were to correspond to the structural detail —N=, this is to be understood as both A=N—C and A-N=C.

If for example in the sequence

the member A were to correspond to the structural detail >C= this is to be understood as being

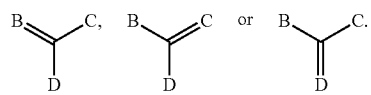

In a diagram such as for example

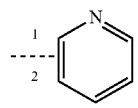

the dotted line indicates that the ring system may be attached to the molecule via the carbon 1 or 2, i.e. is equivalent to the following diagram

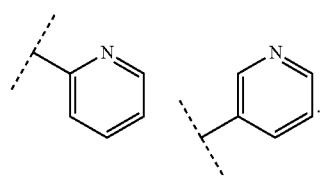

Groups or substituents are frequently selected from among alternative groups/substituents with a corresponding group designation (e.g. $R^a$, $R^b$ etc). If a group of this kind is used repeatedly to define a compound according to the invention in different parts of the molecule, it should always be borne in mind that the respective uses are to be regarded as being totally independent of one another.

List of Abbreviations

| | |
|---|---|
| Ac | acetyl |
| ATP | adenosine triphosphate |
| Bn | benzyl |
| Boc | tert-butyloxycarbonyl |
| Bu | butyl |
| c | concentration |
| chex | cyclohexane |
| d | day(s) |
| TLC | thin layer chromatography |
| DCM | dichloromethane |
| DEA | diethylamine |
| DIPEA | N-ethyl-N,N-diisopropylamine (HÜNIG base) |
| DMAP | 4-N,N-dimethylaminopyridine |
| DME | 1,2-dimethoxyethane |
| DMF | N,N-dimethylformamide |
| DMSO | dimethylsulphoxide |
| DPPA | diphenylphosphorylazide |
| EDTA | ethylenediaminetetraacetic acid |
| EE | ethyl acetate |
| EGTA | ethyleneglycoltetraacetic acid |
| eq | equivalent(s) |
| ESI | electron spray ionization |
| Et | ethyl |
| $Et_2O$ | diethyl ether |
| EtOH | ethanol |
| h | hour |
| HATU | O-(7-azabenzotriazol-1-yl)-N,N,N',N'-tetramethyl-uronium hexafluorophosphate |
| hex | hexyl |
| HPLC | high performance liquid chromatography |
| Hünig-base | N-ethyl-N,N-diisopropylamine |
| i | iso |
| cat., cat. | catalyst, catalytic |
| conc. | concentrated |
| LC | liquid chromatography |
| sln. | solution |
| mCPBA | meta-chloroperbenzoic acid |
| Me | methyl |
| MeOH | methanol |
| min | minutes |
| MPLC | medium pressure liquid chromatography |
| MS | mass spectrometry |
| NMP | N-methylpyrrolidone |
| NP | normal phase |
| n.a. | not available |
| PBS | phosphate-buffered saline |
| Ph | phenyl |
| PMSF | benzylsulphonic acid fluoride |
| Pr | propyl |
| Py | pyridine |
| rac | racemic |
| red. | reduction |
| $R_f$(Rf) | retention factor |
| RP | reversed phase |
| RT | ambient temperature |
| $S_N$ | nucleophilic substitution |
| TBAF | tetrabutylammonium fluoride |
| TBME | tert-butylmethylether |
| TBTU | O-(benzotriazol-1-yl)-N,N,N',N'-tetramethyl-uronium tetrafluoroborate |
| TEA | triethylamine |
| temp. | temperature |
| tert. | tertiary |
| Tf | triflate |
| TFA | trifluoroacetic acid |
| THF | tetrahydrofuran |
| TMS | trimethylsilyl |
| $t_{Ret}$ | retention time (HPLC) |
| TRIS | tris(hydroxymethyl)-aminomethane |
| TsOH | para-toluenesulphonic acid |
| UV | ultraviolet |

Features and advantages of the present invention will become apparent from the following detailed Examples, which illustrate the fundamentals of the invention by way of example, without restricting its scope:

Preparation of the Compounds According to the Invention

General

Unless stated otherwise, all the reactions are carried out in commercially obtainable apparatus using methods that are commonly used in chemical laboratories. Starting materials that are sensitive to air and/or moisture are stored under protective gas and corresponding reactions and manipulations therewith are carried out under protective gas (nitrogen or argon).

Microwave reactions are carried out in an initiator/reactor made by Biotage or in an Explorer made by CEM in sealed containers (preferably 2, 5 or 20 mL), preferably with stirring.

Chromatography

For preparative medium pressure chromatography (MPLC) silica gel made by Millipore (name: Granula Silica Si-60A 35-70 μm, NP phase) or C-18 RP-silica gel (RP-phase) made by Macherey Nagel (name: Polygoprep 100-50 C18) is used. Automated normal phase chromatography is also carried out on a CombiFlash Companion XL apparatus in combination with a CombiFlash Foxy 200 fraction collector made by Isco. For this, commercially obtainable RediSepRf (120 g silica gel) one-way columns are used. The thin layer chromatography is carried out on ready-made silica gel 60 TLC plates on glass (with fluorescence indicator F-254) made by Merck.

The preparative high pressure chromatography (HPLC) of the example compounds according to the invention is carried out with columns made by Waters (names: XTerra Prep. MS C18, 5 μm, 30×100 mm or XTerra Prep. MS C18, 5 μm, 50×100 mm OBD or Symmetrie C18, 5 μm, 19×100 mm or Sunfire C18 OBD, 19×100 mm, 5 μm or Sunfire Prep C 10 μm OBD 50×150 mm or X-Bridge Prep C18 5 μm OBD 19×50 mm), Agilent (name: Zorbax SB-C8 5 μm PrepHT 21.2×50 mm) and Phenomenex (names: Gemini C18 5 μm AXIA 21.2×50 mm or Gemini C18 10 μm 50×150 mm).

The analytical HPLC (reaction control) of intermediate compounds is carried out using columns made by Agilent (names: Zorbax SB-C8, 5 μm, 21.2×50 mm or Zorbax SB-C8 3.5 μm 2.1×50 mm) and Phenomenex (name: Gemini C18 3 μm 2×30 mm). The analytical equipment is also equipped with a mass detector in each case.

HPLC-Mass Spectroscopy/UV-Spectrometry

The retention times/MS-ESI⁺ for characterising the example compounds according to the invention are produced using an HPLC-MS apparatus (high performance liquid chromatography with mass detector). Compounds that elute at the injection peak are given the retention time $t_{Ret.}$=0.00.

Specific Details of the Method:

HPLC-MS method 1

HPLC: Agilent 1100 Series

MS: Agilent LC/MSD SL

Column: Waters, Xterra MS C18, 2.5 μm, 2.1×30 mm, Part. No. 186000592

Eluant: A: $H_2O$ with 0.1% HCOOH; B: acetonitrile (HPLC grade)

Detection: MS: positive and negative mode

Mass range: 20-900 m/z

Flow 1.10 mL/min

Column temp.: 40° C.

Gradient: 0.00 min: 5% eluant B 0.00-2.50 min: 5%→95% eluant B 2.50-2.80 min: 95% eluant B 2.81-3.10 min: 95%→5% eluant B The compounds according to the invention are prepared by the methods of synthesis described hereinafter, in which the substituents of the general formulae have the meanings given hereinbefore. These methods are intended as an illustration of the invention, without restricting its subject matter and the scope of the compounds claimed to these examples. Where the preparation of starting compounds is not described, they are commercially obtainable or may be prepared analogously to known compounds or methods described herein. Substances described in the literature are prepared according to the published methods of synthesis.

Example Compounds of Type I:

4,6-disubstituted pyrido[3,4-d]pyrimidines I may be obtained for example by the following methods (reaction plan A, synthesis methods 1-3):

Starting from 4,6-dichloro-pyrido[3,4-d]pyrimidine P-1a the 4-position is substituted by the components A-1 or A-2, preferably at elevated temperature. The components A-1 and A-2 are preferably anilines ($L^1$=—NH—), but may also be

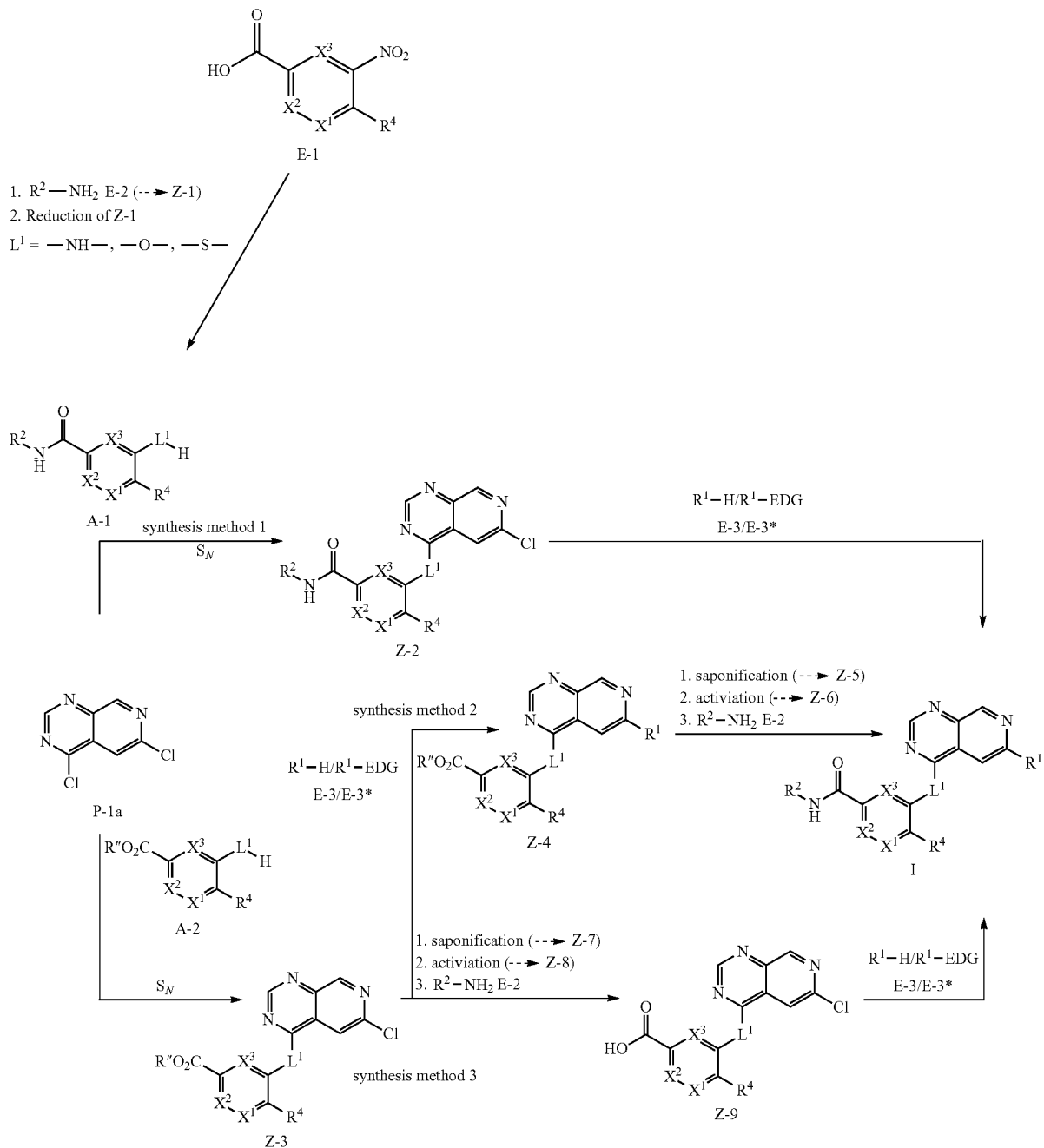

thiophenols and phenols (L¹=—S—, —O—) or the corresponding phenoxides.

When A-1 is used (synthesis method 1), as a result the complete left-hand part of the molecule of the end compounds I is introduced into the intermediate compound Z-2, so that finally there remains only the substitution in the 6-position by components R¹—H (E-3), which are preferably primary and secondary (also cyclic) amines. These substitution reactions are conventional nucleophilic substitutions. It is also possible to attach a C—C bond between R¹ and the pyrido[3,4-d]pyrimidine structure. This requires corresponding C-nucleophiles and transition metalcatalysed cross-coupling reactions. The types of reaction that are additionally suitable for introducing the above-mentioned groups R¹ include the BUCHWALD-HARTWIG, SUZUKI, KUMADA, STILLE, NEGISHI, HECK and SONOGASHIRA reaction. In addition to reagents R¹—H (E-3), compounds R¹-EDG (E-3*) are needed in some of these reactions, EDG being activating electron-pushing groups. Reagents E-3* are particularly boric acids or boric acid ester derivatives [EDG= —B(OH)₂/—B(OR''')₂], organic magnesium and zinc halides (EDG=—MgHal, —ZnHal) and stannans (EDG=—SnR'''₃). Suitable groups R''' are generally known in the art. Aniline components A-1 are obtained by amide coupling of the nitro-carboxylic acids E-1 with amines E-2 to form the intermediate product Z-1 and subsequent reduction of the nitro group. For the amide coupling, optionally common coupling reagents are used, such as those used in peptide chemistry (e.g. HATU or TBTU), or the nitro acids E-1 are activated in some other way, e.g. as acid halides (e.g. with thionyl chloride, oxalyl chloride, GHOSEZ reagent). Instead of E-1, (hetero-)aromatic 3-hydroxy- or 3-mercapto-carboxylic acids may be coupled with E-2 analogously to form components A-1.

By contrast, when using A-2 (synthesis methods 2 and 3) first of all only the central phenyl or heteroaryl ring and a protected linker fragment (carboxylate) of the later linker L² (e.g. amide) is incorporated before the group R¹ is introduced. With the intermediate compound Z-3 there are the alternative possibilities of either substituting/coupling the 6-position with a component E-3/E-3* and then, after saponification, introducing the group R² (through the component E-2) (synthesis method 2) or first of all carrying out saponification and amide coupling of E-2 followed by nucleophilic substitution/cross-coupling by/with E-3/E-3* (synthesis method 3).

Alternatively to P-1a other educts P-1 are also possible which allow successive and selective substitution, i.e. have access to other leaving groups. In particular, bromides and iodides may also be present as halogen leaving groups.

Both the group R¹ and the group R² of compounds I according to the invention may be modified in other reaction steps (not shown), to obtain more compounds I according to the invention. These reaction steps may be reactions of substitution, alkylation, acylation, reduction, deprotection or addition.

a) Method for Synthesising P-1a:

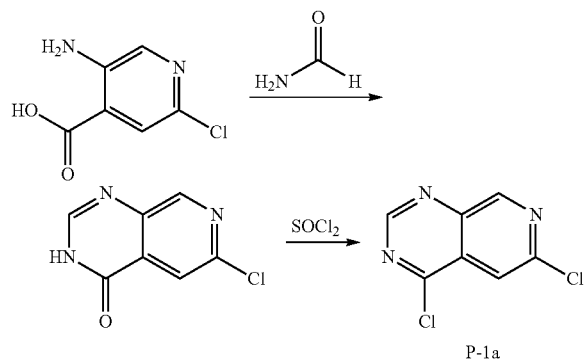

P-1a 5-amino-2-chloro-isonicotinic acid (4 g, 23.18 mmol) is taken up in the form of the amide (50 mL) and stirred for 12 h at 140° C. The reaction mixture is cooled to RT and mixed with water. The precipitate formed is filtered off, washed with water and then dried at 60° C. for 24 h in the vacuum drying cupboard.

The intermediate product obtained, 6-chloro-3H-pyrido[3,4-d]pyrimidin-4-one (745 mg, 4.1 mmol), is suspended in thionyl chloride (10 mL), mixed with one drop of DMF and refluxed for 16 h. The excess thionyl chloride is distilled off. The residue is taken up in DCM, washed 1× with semisaturated NaHCO₃ solution and saturated NaCl solution, dried on Na₂SO₄ and concentrated to dryness by rotary evaporation. The crude product P-1a is further used directly.

b) Method for Synthesising A-1a:

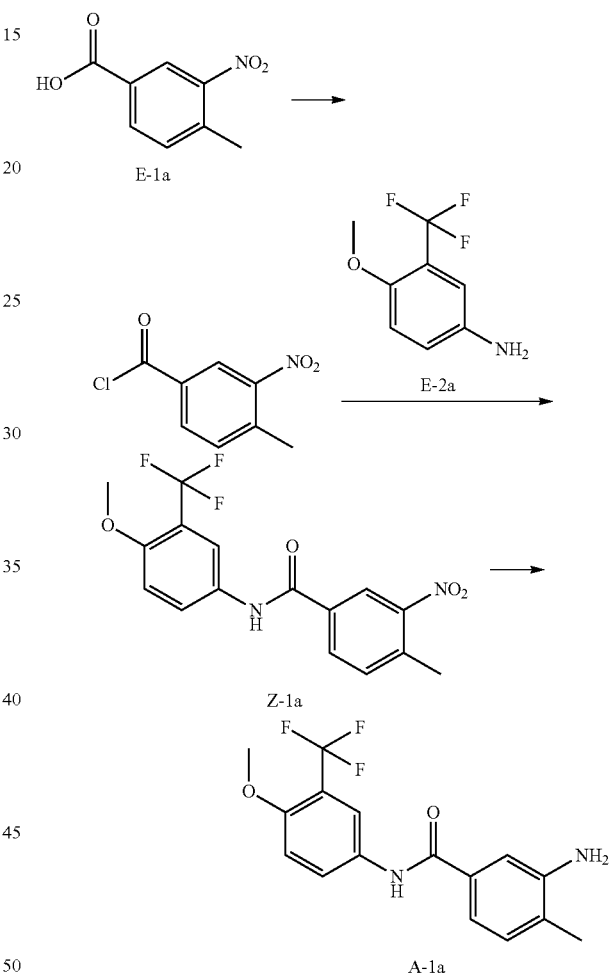

4-methyl-3-nitrobenzoic acid E-1a (1.0 g, 5.47 mmol) is taken up in thionyl chloride (5 mL, 68.5 mmol). The reaction mixture is refluxed for 4 h. Excess thionyl chloride is distilled off and the acid chloride obtained is further used directly.

4-methoxy-3-trifluoromethylaniline E-2a (1.12 g, 5.74 mmol) is taken up in DCM (30 mL), combined with pyridine (1.5 mL, 18.36 mmol) and cooled in the ice bath. Then the acid chloride (1.09 g, 5.46 mmol) dissolved in 20 mL DCM is added dropwise. The reaction mixture is stirred for 10 min in the ice bath and for 1 h at RT, diluted with water and the phases are separated. The organic phase is extracted 2× with semisaturated KHSO₄ solution, 1× with semisaturated NaHCO₃ solution and 1× with saturated NaCl solution and dried on magnesium sulphate, evaporated down and the intermediate compound Z-1a (HPLC-MS: $t_{Ret.}$=1.95 min; MS (M+H)⁺=355) is obtained.

The aromatic nitro compound Z-1a (780 mg, 2.2 mmol) is taken up in MeOH (100 mL), combined with Pd/C (100 mg, 10%) and hydrogenated for 4 h at 4 bar. The reaction mixture is filtered off from the catalyst and the filtrate obtained is dried using the rotary evaporator. The crude product obtained A-1a is further used directly.

c) Method for Synthesising Z-2a:

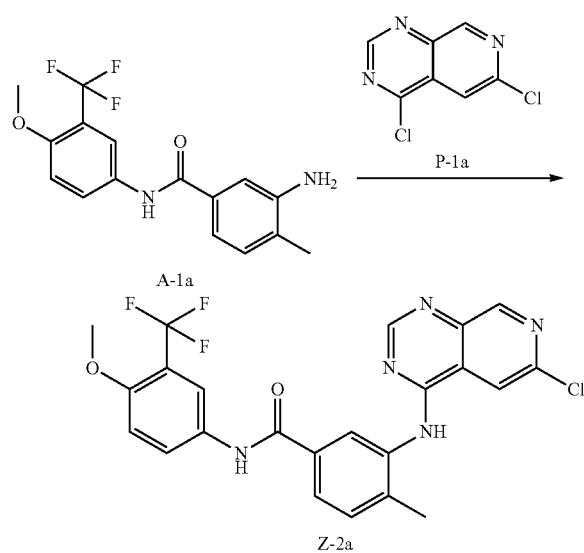

Aniline A-1a (505 mg, 1.56 mmol) is taken up in isopropanol (6 mL), combined with 4,6-dichloro-pyrido[3,4-c]pyrimidine P-1a (330 mg, 1.65 mmol), refluxed for 1 h and stirred overnight at RT. The intermediate product Z-2a obtained as precipitate is filtered off, washed with isopropanol and dried overnight at 60° C.

d) Method for Synthesising Example Compound I-1:

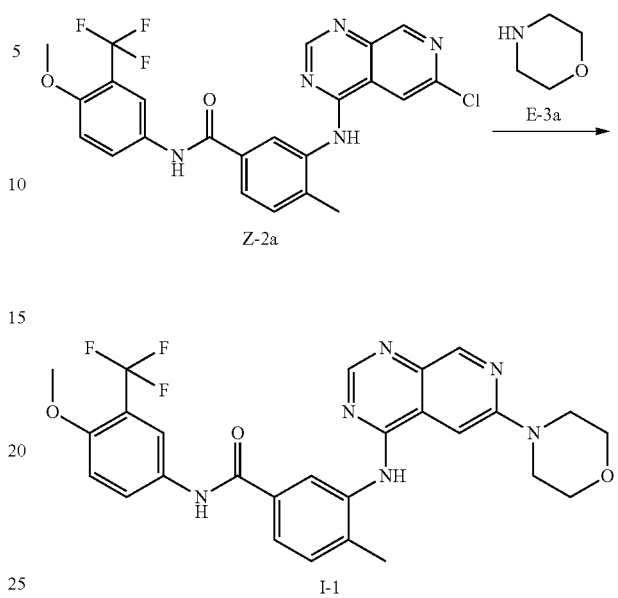

Z-2a (100 mg, 0.21 mmol) is placed in isopropanol (0.5 mL) and NMP (0.5 mL), combined with morpholine E-3a (50 µL, 0.57 mmol) and triethylamine (43 µL, 0.31 mmol) and stirred for 3 h at 160° C. in the microwave reactor. The reaction mixture is filtered and purified by preparative HPLC. The product-containing fractions of I-1 (HPLC-MS: $t_{Ret.}$=1.80 min; MS (M+H)$^+$=539) are freeze-dried.

Analogously to methods a) to d) (synthesis method 1) in addition to I-1 the following novel compounds I-2 to I-4 are prepared (Table 1).

TABLE 1

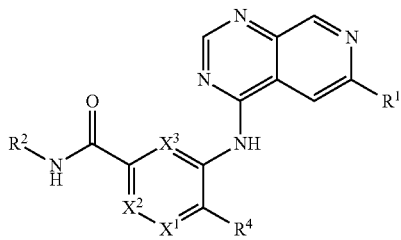

Example compounds I-1 to I-4

| # | Structure | $t_{Ret.}$ (HPLC) [min] | MS (M + H)$^+$ |
|---|-----------|------------------------|----------------|
| I-1 | 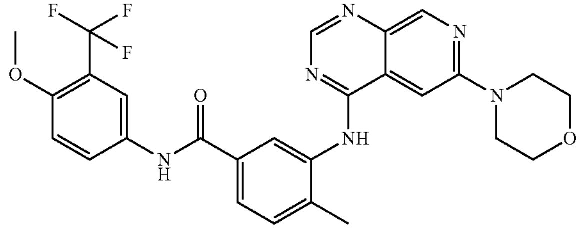 [SMILES: COc1ccc(NC(=O)c2ccc(C)c(Nc3ncnc4cnc(N5CCOCC5)cc34)c2)cc1C(F)(F)F] | 1.80 | 539 |

TABLE 1-continued
Example compounds I-1 to I-4
| # | Structure | $t_{Ret.}$ (HPLC) [min] | MS $(M + H)^+$ |
|---|---|---|---|
| I-2 | 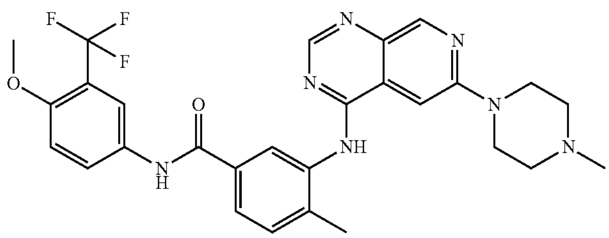 [SMILES: COc1ccc(NC(=O)c2ccc(C)c(Nc3ncnc4cnc(N5CCN(C)CC5)cc34)c2)cc1C(F)(F)F] | 1.79 | 552 |
| I-3 | 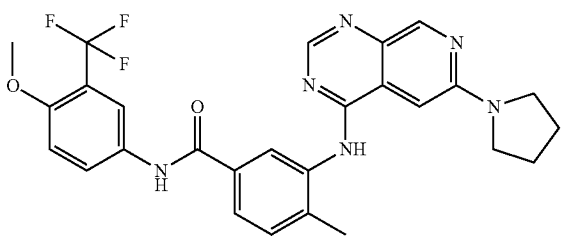 [SMILES: COc1ccc(NC(=O)c2ccc(C)c(Nc3ncnc4cnc(N5CCCC5)cc34)c2)cc1C(F)(F)F] | 1.93 | 523 |
| I-4 | 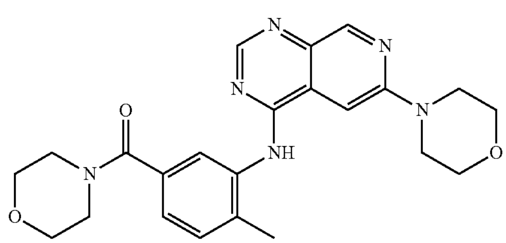 [SMILES: Cc1ccc(C(=O)N2CCOCC2)cc1Nc1ncnc2cnc(N3CCOCC3)cc12] | 1.27 | 435 |
Reaction scheme B
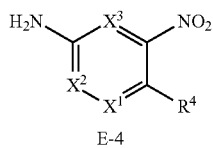
1. $R^2$—COOH E-5 (--→ Z-10)
2. reduction of Z-10
$L^1$ = —NH—, —O—, —S—
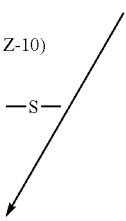

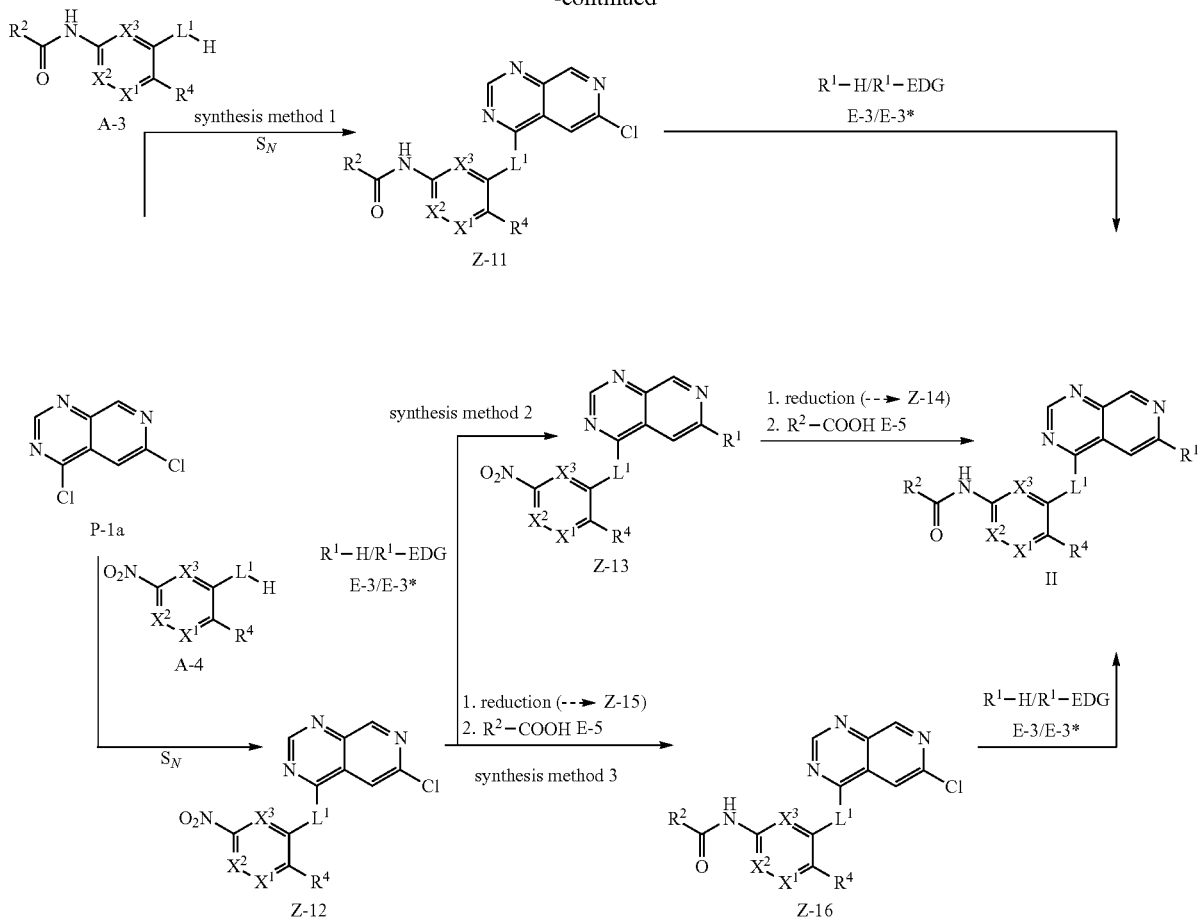

Example Compounds of Type II:

Example compounds II differ from those of type I by an inverted amide bond between the central (hetero-)aromatic six-membered ring and the group $R^2$ (reaction scheme B). These compounds are obtained by an analogous method to compounds I, but the reactivities are inverted in the educt components E-4 and E-5 or A-4 (compared with E-1 and E-2 or A-2). The following synthesis methods are possible for example for compounds of type II: Starting from P-1a the 4-position is substituted by components A-3 or A-4, preferably at elevated temperature. The components A-3 and A-4 are preferably anilines ($L^1$=—NH—), but may also be thiophenols and phenols ($L^1$=—S—, —O—) or the corresponding phenoxides. With regard to the use of A-3 reference should be made to the remarks in connection with reaction scheme A (synthesis method 1 via intermediate compound Z-2).

Aniline components A-3 are obtained by amide coupling of the nitroanilines E-4 with carboxylic acids E-5 to obtain intermediate product Z-10 and subsequent reduction of the nitro group. Instead of E-4, 3-nitro- or 3-aminophenols or -thiophenols may also be reacted analogously to form components A-3.

When A-4 is used (synthesis methods 2 and 3) first of all only the central phenyl or heteroaryl ring and the precursor of a linker fragment (nitro→amino) of the later linker $L^2$ is incorporated. With the intermediate compound Z-12 there are the alternative possibilities of either substituting/coupling the 6-position with a component E-3/E-3* and then, after reduction, introducing the group $R^2$ (through the component E-5) (synthesis method 2) or first of all carrying out reduction and amide coupling with E-5 followed by nucleophilic substitution/coupling by E-3/E-3* (synthesis method 3).

Both the group $R^1$ and the group $R^2$ of compounds II according to the invention may be modified in other reaction steps (not shown), to obtain more compounds II according to the invention. These reaction steps may be reactions of substitution, alkylation, acylation, reduction, deprotection or addition.

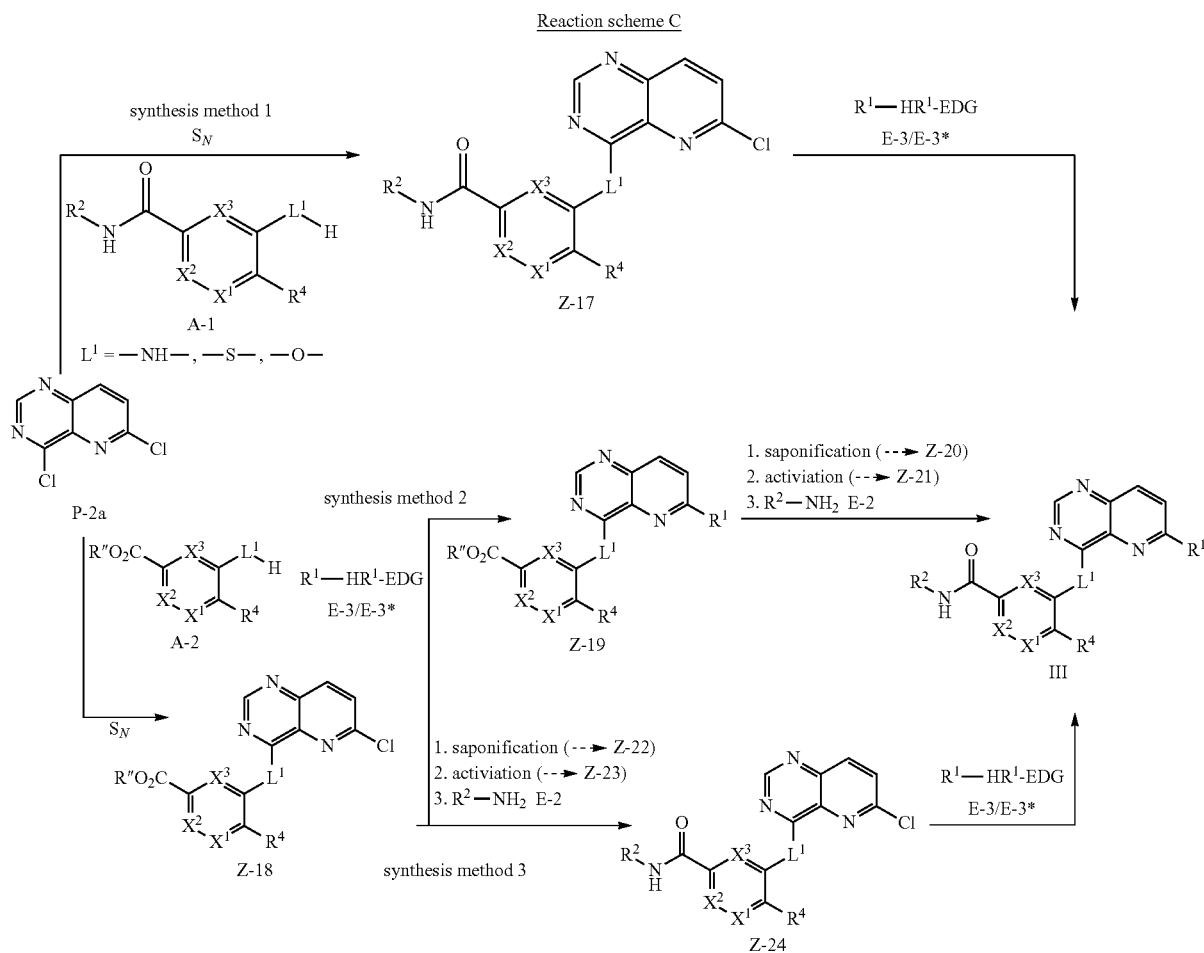

Reaction scheme C

Example Compounds of Type III:

4,6-disubstituted pyrido[3,2-d]pyrimidines III may be obtained for example by the following methods (reaction plan C, synthesis methods 1-3):

Starting from 4,6-dichloro-pyrido[3,2-d]pyrimidine P-2a the 4-position is substituted by the aniline or (thio)phenol components (or the corresponding phenoxides) A-1 or A-2, preferably at elevated temperature.

When A-1 is used (synthesis method 1), as a result the complete left-hand part of the molecule of the end compounds III is introduced into the intermediate compound Z-17, so that finally there remains only the substitution in the 6-position by components $R^1$—H (E-3), which are preferably primary and secondary (also cyclic) amines (for the synthesis of components A-1 cf. the remarks under Reaction scheme A). These substitution reactions are conventional nucleophilic substitutions. It is also possible to attach a C—C bond between $R^1$ and the pyrido[3,2-d]pyrimidine structure. This requires corresponding C-nucleophiles and transition metal-catalysed cross-coupling reactions. The types of reaction that are additionally suitable for introducing the above-mentioned groups $R^1$ include the BUCHWALD-HARTWIG, SUZUKI, KUMADA, STILLE, NEGISHI, HECK and SONOGASHIRA reaction. In addition to reagents $R^1$—H (E-3), compounds $R^1$-EDG (E-3*) are needed in some of these reactions, EDG being activating electron-pushing groups. Reagents E-3* are particularly boric acids or boric acid ester derivatives [EDG= —B(OH)$_2$/—B(OR''')$_2$], organic magnesium and zinc halides (EDG=—MgHal, —ZnHal) and stannans (EDG=—SnR'''$_3$). Suitable groups R''' are generally known in the art.

By contrast, when using A-2 (synthesis methods 2 and 3) first of all only the central phenyl or heteroaryl ring and a protected linkter fragment (carboxylate) of the later linker $L^2$ (e.g. amide) is incorporated before the group $R^1$ is introduced. With the intermediate compound Z-18 there are the alternative possibilities of either substituting/coupling the 6-position with a component E-3/E-3* and then, after saponification, introducing the group $R^2$ (through the component E-2) (synthesis method 2) or first of all carrying out saponification and amide coupling of E-2 followed by nucleophilic substitution/cross-coupling by E-3/E-3* (synthesis method 3).

Alternatively to P-2a other educts P-2 are also possible which allow successive and selective substitution, i.e. have access to other leaving groups. In particular, bromides and iodides may also be present as halogen leaving groups.

Both the group $R^1$ and the group $R^2$ of compounds III according to the invention may be modified in other reaction steps (not shown), to obtain more compounds III according to the invention. These reaction steps may be reactions of substitution, alkylation, acylation, reduction, deprotection or addition.

a) Method for Synthesising P-2a:

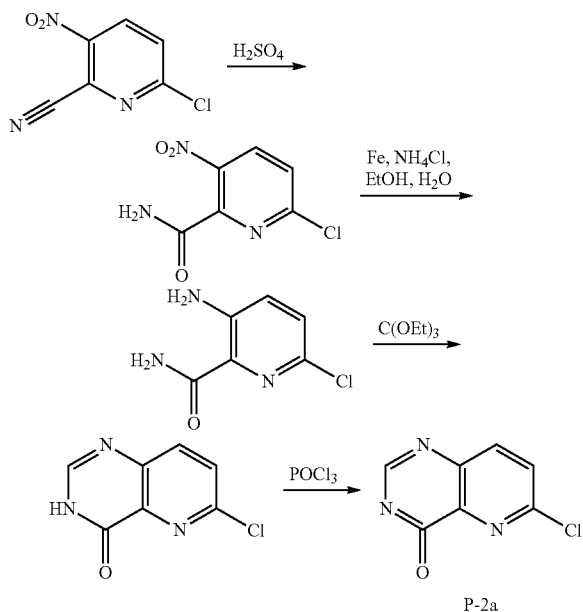

6-chloro-2-cyano-3-nitropyridine (9.50 g, 51.76 mmol) is taken up in 150 mL of 90% H₂SO₄ solution. The reaction mixture is stirred for 4 h at 70° C., cooled and slowly added dropwise to ice water. The precipitate formed is filtered off, washed with water and dried. The aqueous filtrate is extracted 6× with DCM. The organic phases are combined, dried on Na₂SO₄, filtered off and concentrated by rotary evaporation. The residue is mixed with the precipitate, dried overnight at 50° C. in the drying cupboard and 6-chloro-3-nitro-pyridine-2-carboxylic acid amide (HPLC-MS: $t_{Ret.}$=0.43 min; MS $(M+H)^+$=202) is obtained.

6-chloro-3-nitro-pyridine-2-carboxylic acid amide (10.43 g, 51.75 mmol) is taken up in EtOH (250 mL), combined with ammonium chloride (1.384 g, 25.87 mmol) in water (250 mL) and heated to 60° C. At this temperature iron powder (8.67 g, 155.23 mmol) is added batchwise and the mixture is stirred for 1 h at 60° C. After cooling it is concentrated by rotary evaporation, filtered through silica gel, washed with DCM/MeOH (90/10 to 80/20), the resulting filtrate is evaporated down using the rotary evaporator and 3-amino-6-chloro-pyridine-2-carboxylic acid amide (HPLC-MS: $t_{Ret.}$=0.90 min; MS $(M+H)^+$=172) is obtained.

3-amino-6-chloro-pyridine-2-carboxylic acid amide (7.45 g, 43.41 mmol) is taken up in triethylorthoformate (150 mL) and stirred for 3 h at 145° C. After cooling the precipitate formed is filtered off, washed with Et₂O, dried and 6-chloro-3H-pyrido[3,2-d]pyrimidin-4-one (HPLC-MS: $t_{Ret.}$=0 min; MS $(M+H)^+$=182) is obtained.

6-chloro-3H-pyrido[3,2-d]pyrimidin-4-one (7.16 g, 39.43 mmol) and N,N-diethylaniline (9.505 mL, 59.14 mmol) are taken up in toluene (185 mL) and heated to 110° C. Then POCl₃ (3.713 mL, 39.43 mmol) is slowly added dropwise. The reaction mixture is stirred for a further 4 h at 110° C. After cooling the mixture is diluted with toluene, washed 2× with water, 2× with 20% NaOH solution and 1× with 1M HCl solution. The organic phase is dried on MgSO₄, filtered off, evaporated down and P-2a is obtained (HPLC-MS: $t_{Ret.}$=1.14 min).

Method of synthesis from: *J. Med. Chem.* 1996, 39, 1823-1835.

b) Method for Synthesising A-2a:

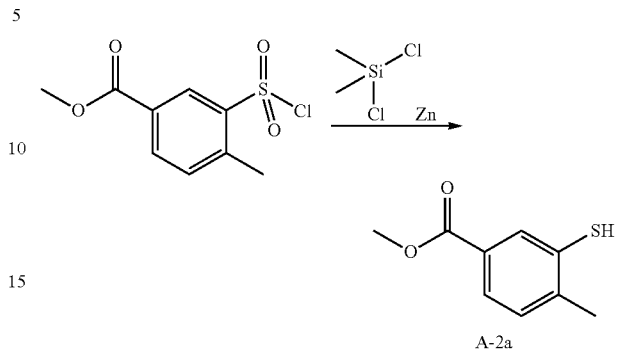

Zinc powder (950 mg, 14.53 mmol) and dichlorodimethylsilane (1.7 mL, 14.11 mmol) are taken up in 1,2-dichloroethane (7 mL) under argon. Methyl 3-chlorosulphonyl-4-methyl-benzoate (1.0 g, 4.02 mmol) and dimethylacetamide (1.125 mL, 12.18 mmol) are dissolved in 1,2-dichloroethane (8 mL) and added dropwise to the zinc suspension while cooling with an ice bath. The reaction mixture is heated to RT and stirred for 2 h at this temperature. For working up the mixture is filtered off, washed with MeOH and concentrated by rotary evaporation. The residue is taken up in MeOH, filtered off, concentrated by rotary evaporation and A-2a is obtained.

c) Method for Synthesising Z-18a:

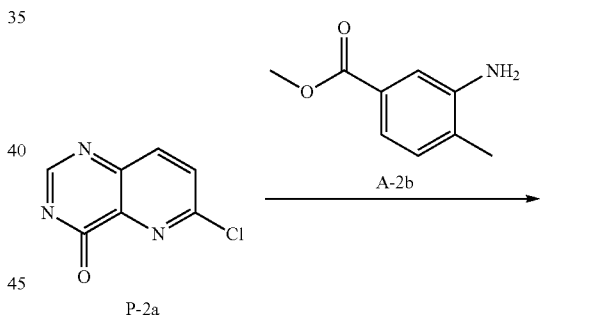

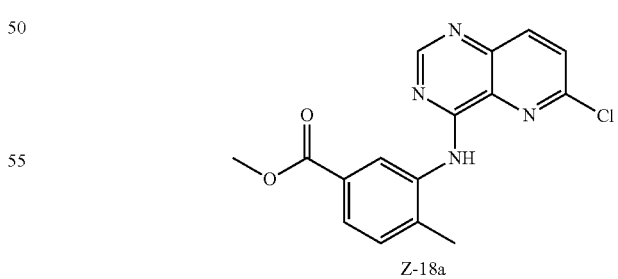

4,6-dichloro-pyrido[3,2-d]pyrimidine P-2a (3.50 g, 17.50 mmol) and methyl 3-amino-4-methyl-benzoate A-2b (2.89 g, 17.50 mmol) are taken up in isopropanol (70 mL) and stirred for 30 min at 85° C. After cooling the precipitate formed is filtered off, washed with cyclohexane, dried and Z-18a is obtained (HPLC-MS: $t_{Ret.}$=2.01 min; MS $(M+H)^+$=329).

d) Method for Synthesising Z-18b:

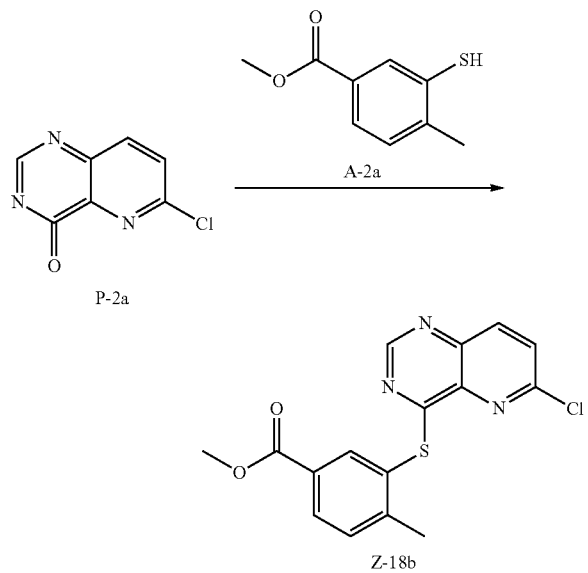

4,6-dichloro-pyrido[3,2-d]pyrimidine P-2a (800 mg, 4.0 mmol) and methyl 3-mercapto-4-methyl-benzoate A-2a (733 mg, 4.0 mmol) are taken up in isopropanol (6 mL) and stirred for 1 h at RT. The precipitate formed is filtered off, washed with cyclohexane, dried and Z-18b is obtained (HPLC-MS: $t_{Ret.}$=1.98 min; MS (M+H)$^+$=346/348).

Analogously to the method for synthesising Z-18a and Z-18b other intermediate compounds Z-18 are obtained by reacting components A-2 with P-2a.

e) Method for Synthesising Z-19a:

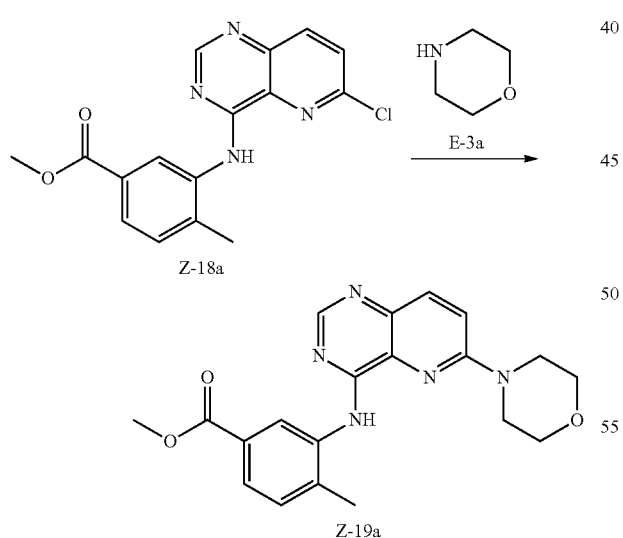

Z-18a (1.10 g, 3.35 mmol) is placed in isopropanol (9 mL) and NMP (3 mL), combined with morpholine E-3a (584 μL, 6.69 mmol) and stirred for 2 h at 150° C. in the microwave reactor. After cooling the precipitate formed is filtered off, washed with isopropanol, dried and Z-19a is obtained (HPLC-MS: $t_{Ret.}$=1.61 min; MS (M+H)$^+$=380).

f) Method for Synthesising Z-19b:

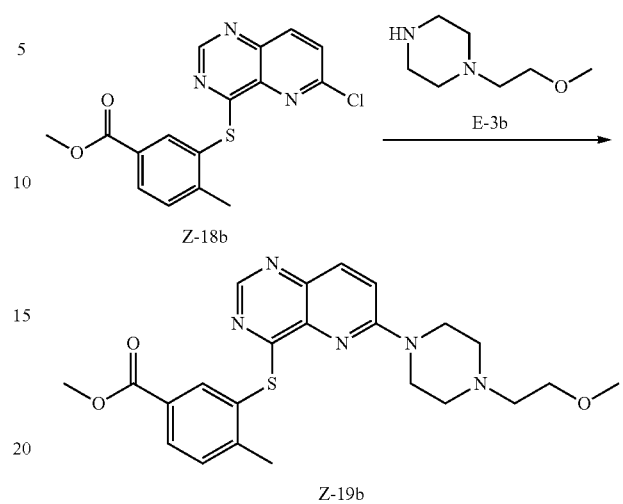

Z-18b (1.30 g, 3.76 mmol) is placed in isopropanol (6.5 mL) and NMP (6.5 mL), combined with 1-(2-methoxyethyl)-piperazine E-3b (773 mg, 5.36 mmol) and stirred for 1 h at 80° C. in the microwave reactor. The reaction mixture is evaporated down by half, filtered and purified by preparative HPLC. The product-containing fractions of Z-19b (HPLC-MS: $t_{Ret.}$=1.90 min; MS (M+H)$^+$=454) are freeze-dried.

Analogously to the method for synthesising Z-19a and Z-19b further intermediate compounds Z-19 are obtained by reacting components Z-18 with educts E-3.

g) Method for Synthesising Z-20a:

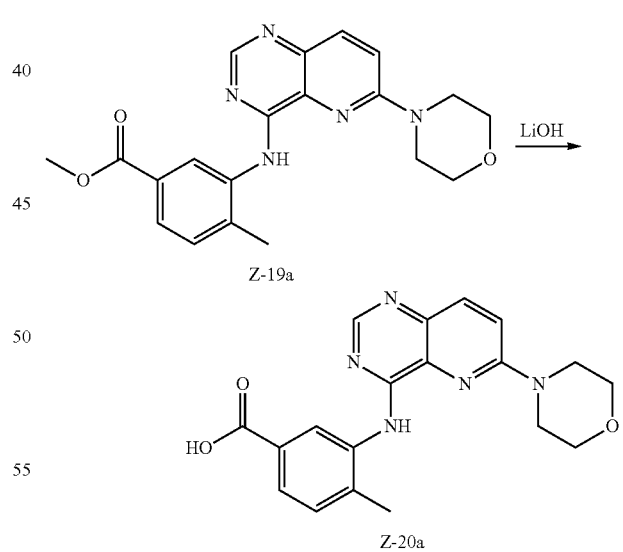

Z-19a (1.36 g, 3.58 mmol) is placed in THF (20 mL), combined with LiOH (594 mg, 14.34 mmol) in 10 mL water and refluxed for 2 h. After cooling the THF is concentrated by rotary evaporation and the aqueous residue is combined with 1M HCl solution. The precipitate formed is filtered off, washed with water, dried overnight at 50° C. and Z-20a is obtained (HPLC-MS: $t_{Ret.}$=0.91 min; MS (M+H)$^+$=366).

h) Method for Synthesising Z-20b:

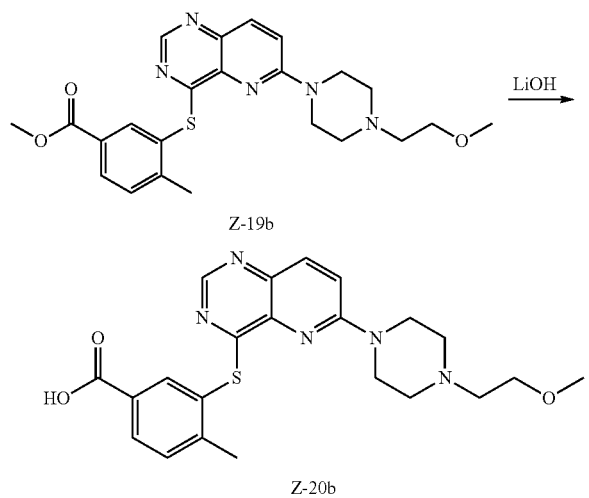

Z-19b (389 mg, 0.86 mmol) is placed in THF (15 mL), combined with LiOH (142 mg, 3.43 mmol) in 6 mL water and stirred overnight at RT. The THF is concentrated by rotary evaporation. The aqueous residue is diluted with DMF, filtered and purified by preparative HPLC. The product-containing fractions of Z-20b (HPLC-MS: $t_{Ret.}$=1.08 min; MS $(M+H)^+$=440) are freeze-dried.

i) Method for Synthesising Example Compound III-1:

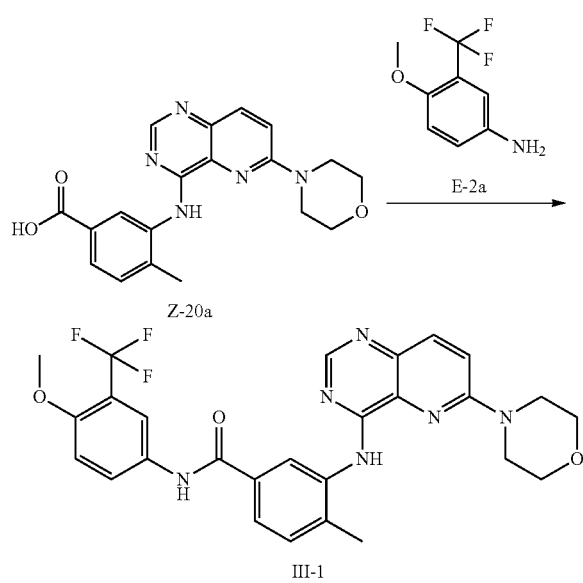

Z-20a (100 mg, 0.27 mmol) is placed in NMP (0.8 mL), combined with DIPEA (106 mg, 0.82 mmol) and HATU (115 mg, 0.30 mmol) and stirred for 30 min at RT. The resulting active ester Z-21a is combined with 4-methoxy-3-trifluoromethylaniline E-2a (63 mg, 0.33 mmol) and stirred overnight at RT. The reaction mixture is filtered and purified by preparative HPLC. The product-containing fractions of III-1 (HPLC-MS: $t_{Ret.}$=2.11 min; MS $(M+H)^+$=539) are freeze-dried.

j) Method for Synthesising Example Compound III-52:

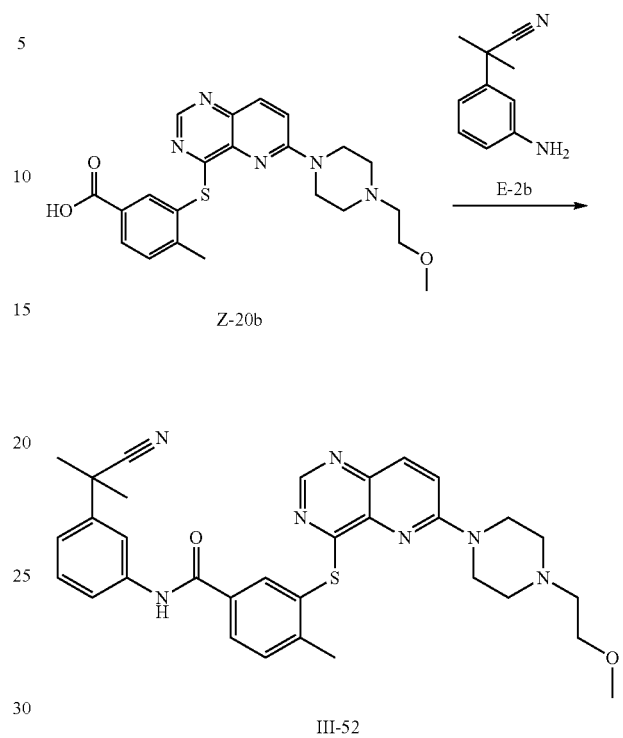

Z-20b (78 mg, 0.18 mmol) is placed in NMP (0.8 mL), combined with DIPEA (69 mg, 0.53 mmol) and HATU (74 mg, 0.20 mmol) and stirred for 30 min at RT. The resulting active ester Z-21b is combined with aniline E-2b (34 mg, 0.21 mmol) and stirred for 3 h at RT. The reaction mixture is filtered and purified by preparative HPLC. The product-containing fractions of III-52 (HPLC-MS: $t_{Ret.}$=1.97 min; MS $(M+H)^+$=582) are freeze-dried.

k) Method for Synthesising Z-22a:

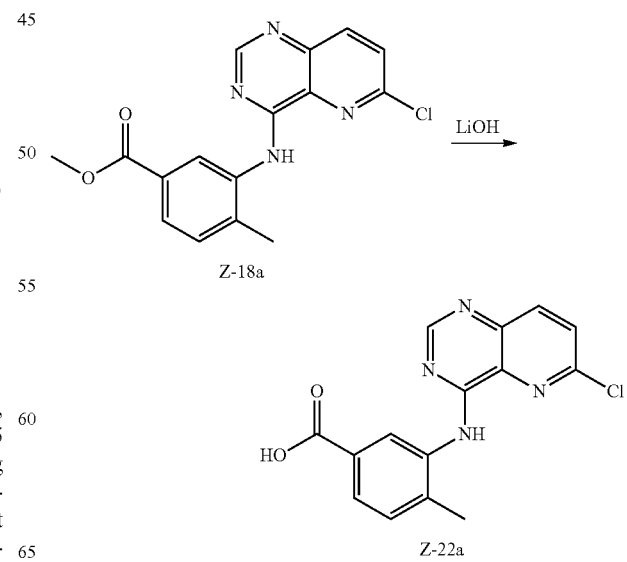

Z-18a (1.48 g, 4.50 mmol) is placed in THF (30 mL), combined with LiOH (746 mg, 18.0 mmol) in 15 mL water and stirred overnight at RT. The THF is concentrated by rotary evaporation and the aqueous residue is combined with 2M HCl solution. The precipitate formed is filtered off, washed with water, dried overnight at 50° C. and Z-22a is obtained (HPLC-MS: $t_{Ret}$=0 min; MS (M+H)$^+$=315).

l) Method for Synthesising Z-24a:

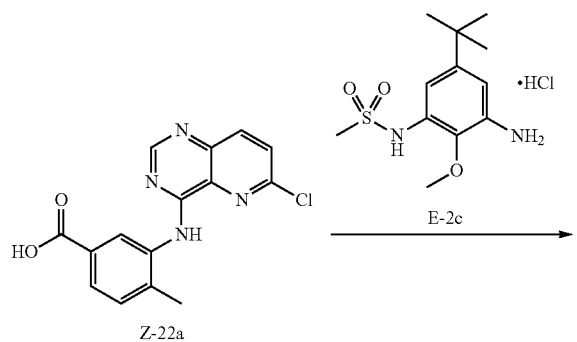

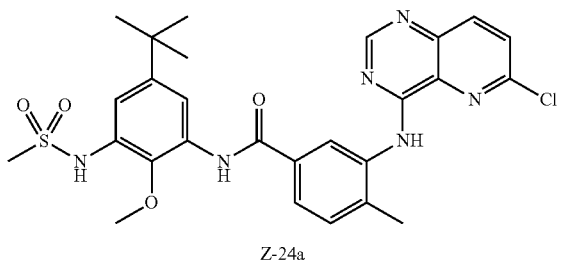

Z-22a (970 mg, 3.08 mmol) is placed in DMF (10 mL), combined with DIPEA (1.583 mL, 9.25 mmol) and HATU (1.289 g, 3.39 mmol) and stirred for 1.5 h at RT. The active ester formed Z-23a is diluted with 10 mL DMF, combined with aniline E-2c (as hydrochloride; 952 mg, 3.082 mmol) and stirred overnight at 40° C. After cooling the mixture is mixed with water, the precipitate formed is filtered off, washed with water, dried and Z-24a (HPLC-MS: $t_{Ret}$=1.71 min; MS (M+H)$^+$=569/571) is obtained.

m) Method for Synthesising Example Compound III-19:

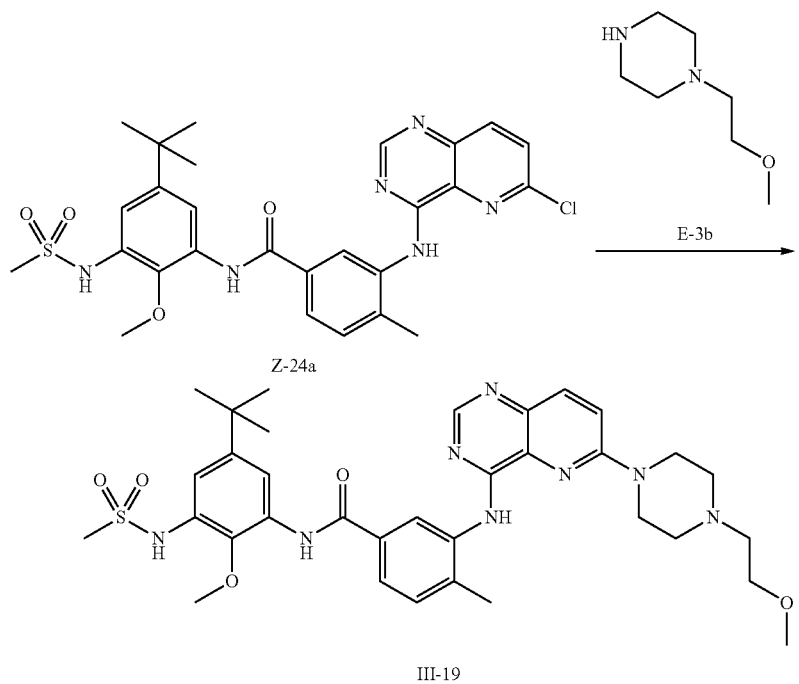

Z-24a (100 mg, 0.15 mmol) is placed in isopropanol (0.5 mL) and NMP (0.5 mL), combined with 1-(2-methoxyethyl)-piperazine E-3b (26 mg, 0.18 mmol) and stirred for 1 h at 120° C. in the microwave reactor. The reaction mixture is filtered and purified by preparative HPLC. The product-containing fractions of III-19 (HPLC-MS: $t_{Ret}$=1.78 min; MS (M+H)$^+$=677) are freeze-dried.

n) Method for Synthesising Example Compounds III-31 and III-36 (via III-56 and III-57):

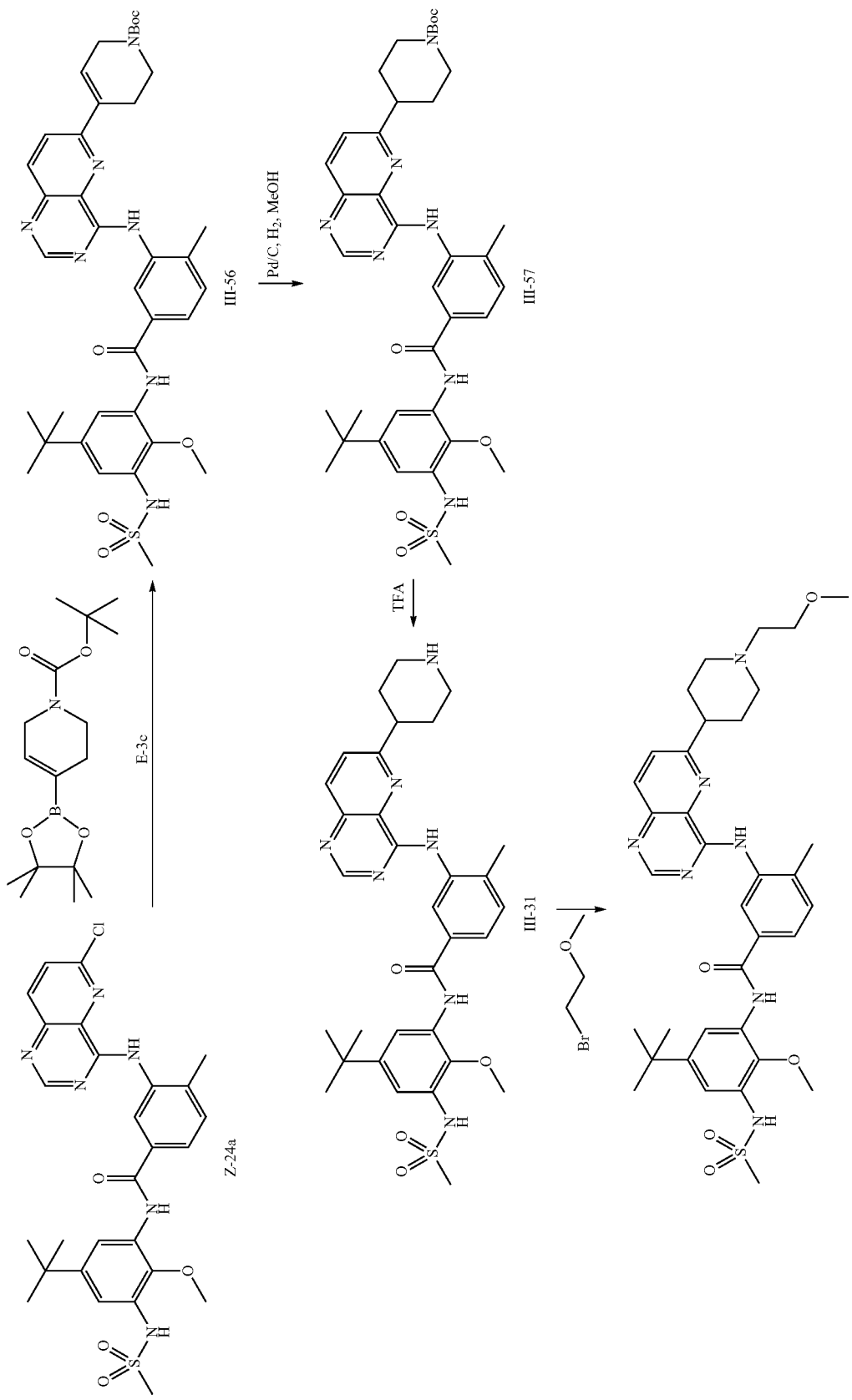

Z-24a (600 mg, 1.05 mmol), N-Boc-4-(pinacoloboric acid ester)-piperidine (400 mg, 1.29 mmol), [1,1'-bis(diphenylphosphino)ferrocene]palladium(II)-dichloride dichloromethane complex (101 mg, 0.12 mmol) and K$_2$CO$_3$ (514 mg, 3.72 mmol) are placed under argon in dioxane (9 mL) and water (3 mL) and stirred for 1.5 h at 100° C. in the microwave reactor. After cooling the precipitate formed is filtered off, washed with water, dried and III-56 (HPLC-MS: $t_{Ret.}$=2.08 min; MS (M+H)$^+$=716) is obtained.

Example compound III-56 (570 mg, 0.80 mmol) is taken up in MeOH (80 mL), combined with Pd/C (100 mg, 10%) and hydrogenated for 2 days at 4 bar. The reaction mixture is filtered through Celite®, washed with MeOH, the filtrate obtained is dried using the rotary evaporator and III-57 (HPLC-MS: $t_{Ret.}$=2.10 min; MS (M+H)$^+$=718) is obtained.

Example compound III-57 (570 mg, 0.80 mmol) is taken up in DCM (10 mL), combined with TFA (0.8 mL) and stirred for 4 h at RT. For working up the mixture is concentrated by rotary evaporation, dissolved in DMF, filtered and purified by preparative HPLC. The product-containing fractions of III-31 (HPLC-MS: $t_{Ret.}$=1.79 min; MS (M+H)$^+$=618) are freeze-dried.

Example compound III-31 (100 mg, 0.16 mmol) and TEA (35 µL, 0.24 mmol) are taken up in THF (1 mL). 2-Bromoethyl-methylether (68 mg, 0.49 mmol) is added dropwise and the reaction mixture is stirred overnight at 60° C. For working up it is concentrated by rotary evaporation, taken up in DMSO, filtered and purified by preparative HPLC. The product-containing fractions of III-36 (HPLC-MS: $t_{Ret.}$=1.82 min; MS (M+H)$^+$=676) are freeze-dried.

o) Method for Synthesising Example Compound III-43 (via III-58):

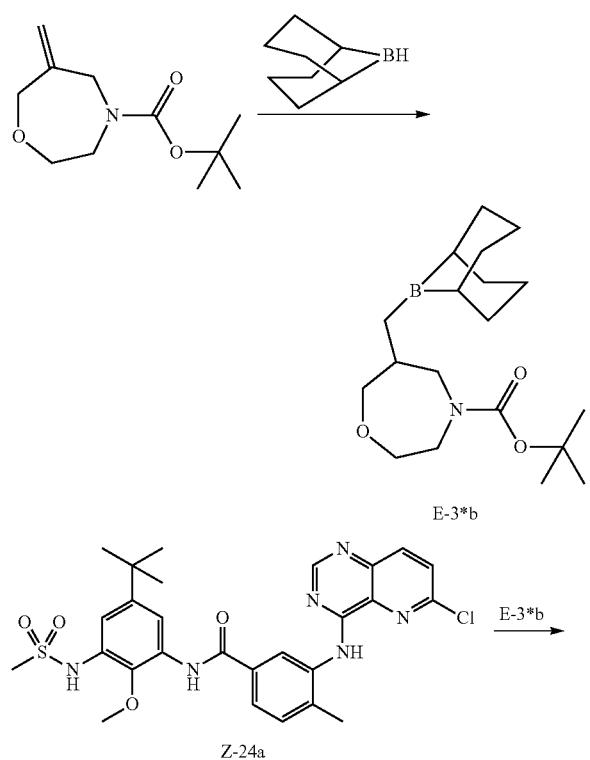

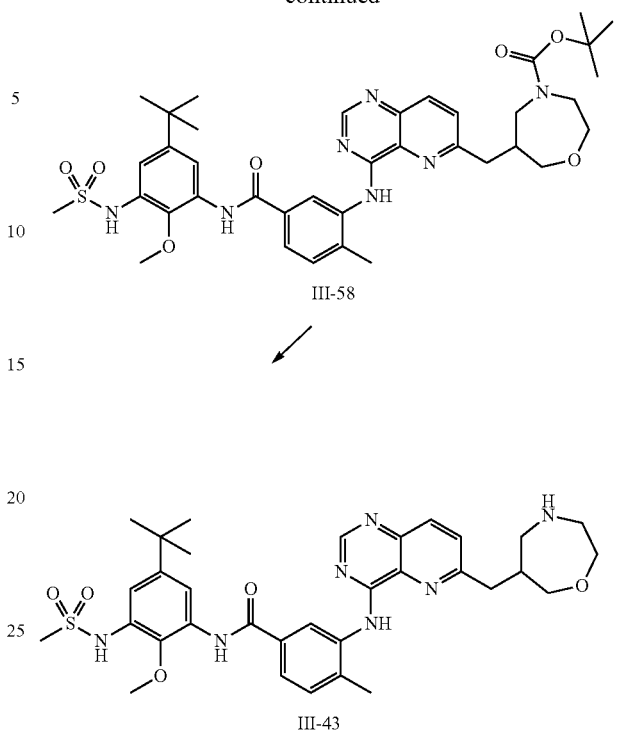

tert-Butyl 6-methylene-perhydro-1,4-oxazepine-4-carboxylate (84 mg, 0.39 mmol) is taken and 9-borabicyclo[3.3.1]nonane solution in THF (0.5 M; 1.05 mL, 0.53 mmol) is added dropwise under argon. The mixture is heated, stirred for 1 h at 65° C. and then cooled to RT. The solution of E-3*b thus obtained is used directly in the next step.

Z-24a (150 mg, 0.26 mmol), [1,1'-bis(diphenylphosphino)ferrocene]palladium(II)-dichloride dichloromethane complex (11 mg, 0.013 mmol) and K$_2$CO$_3$ (42 mg, 0.3 mmol) are placed under argon in DMF (0.75 mL) and water (0.15 mL). The solution of E-3*b is added dropwise, the reaction mixture is stirred for 40 min at 60° C. and then cooled to RT. For working up the mixture is diluted with 1 mL DMF, filtered and purified by preparative HPLC. The product-containing fractions of III-58 (HPLC-MS: $t_{Ret.}$=2.08 min; MS (M+H)$^+$=748) are freeze-dried.

Example compound III-58 (41 mg, 0.06 mmol) is taken up in DCM (2 mL) and combined with TFA (0.2 mL). The reaction mixture is stirred overnight at RT. For working up the mixture is concentrated by rotary evaporation, taken up in DMF, filtered and purified by preparative HPLC. The product-containing fractions of III-43 (HPLC-MS: $t_{Ret.}$=1.81 min; MS (M+H)$^+$=648) are freeze-dried.

In addition to III-1, III-19, III-31, III-36, III-43, III-52, III-56, III-57 and III-58, the following novel compounds III-2 to III-55 (Table 2) are prepared analogously to methods a) to j) (synthesis method 2), a), c), d) and k) to o) (synthesis method 3) or synthesis method 1 as shown.

TABLE 2

Example compounds III-1 bis III-58

| # | Structure | $t_{Ret.}$ (HPLC) | MS $(M + H)^+$ |
|---|---|---|---|
| III-1 | 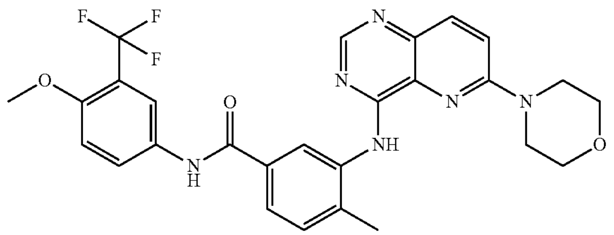 [SMILES: COc1ccc(NC(=O)c2ccc(C)c(Nc3ncnc4ccc(N5CCOCC5)nc34)c2)cc1C(F)(F)F] | 2.11 | 539 |
| III-2 | 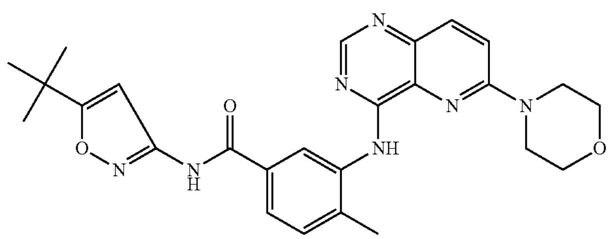 [SMILES: Cc1ccc(C(=O)Nc2cc(C(C)(C)C)on2)cc1Nc1ncnc2ccc(N3CCOCC3)nc12] | 2.08 | 488 |
| III-3 | 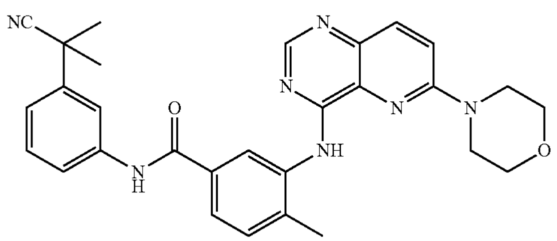 [SMILES: Cc1ccc(C(=O)Nc2cccc(C(C)(C)C#N)c2)cc1Nc1ncnc2ccc(N3CCOCC3)nc12] | 2.09 | 508 |
| III-4 | 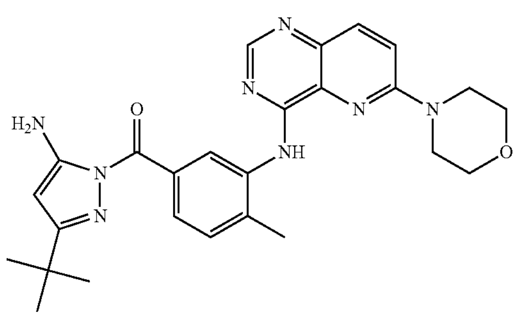 [SMILES: Cc1ccc(C(=O)n2nc(C(C)(C)C)cc2N)cc1Nc1ncnc2ccc(N3CCOCC3)nc12] | 2.22 | 487 |
| III-5 | 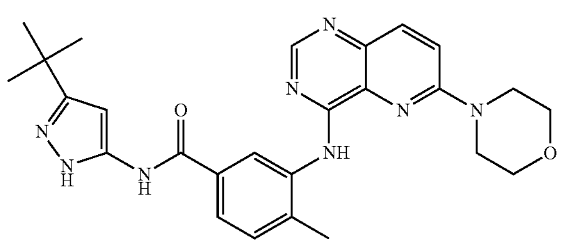 [SMILES: Cc1ccc(C(=O)Nc2cc(C(C)(C)C)n[nH]2)cc1Nc1ncnc2ccc(N3CCOCC3)nc12] | 1.94 | 487 |

TABLE 2-continued

Example compounds III-1 bis III-58

| # | Structure | $t_{Ret.}$ (HPLC) | MS $(M + H)^+$ |
|---|---|---|---|
| III-6 | 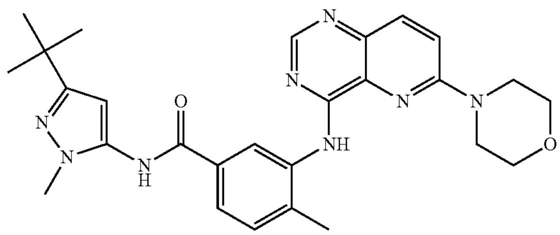 [SMILES: Cc1ccc(C(=O)Nc2cc(C(C)(C)C)nn2C)cc1Nc1ncnc2ccc(N3CCOCC3)nc12] | 1.98 | 501 |
| III-7 | 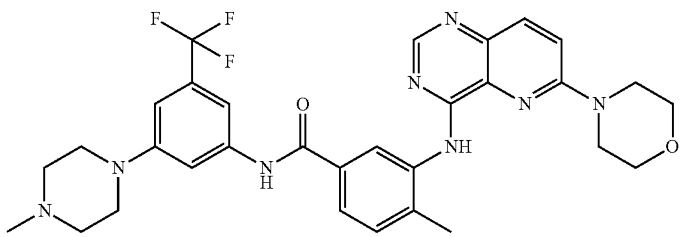 [SMILES: Cc1ccc(C(=O)Nc2cc(N3CCN(C)CC3)cc(C(F)(F)F)c2)cc1Nc1ncnc2ccc(N3CCOCC3)nc12] | 2.18 | 607 |
| III-8 | 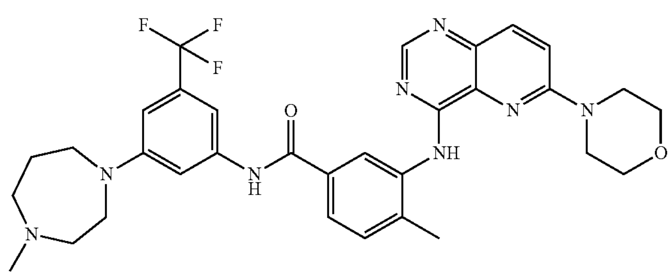 [SMILES: Cc1ccc(C(=O)Nc2cc(N3CCCN(C)CC3)cc(C(F)(F)F)c2)cc1Nc1ncnc2ccc(N3CCOCC3)nc12] | 2.22 | 621 |
| III-9 | 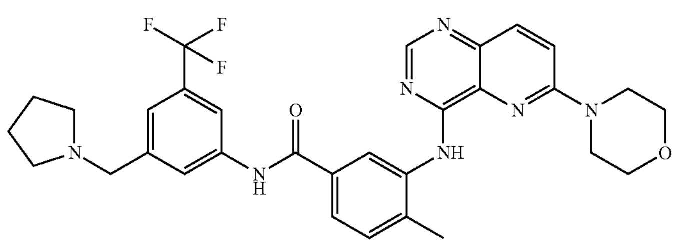 [SMILES: Cc1ccc(C(=O)Nc2cc(CN3CCCC3)cc(C(F)(F)F)c2)cc1Nc1ncnc2ccc(N3CCOCC3)nc12] | 2.27 | 592 |
| III-10 | 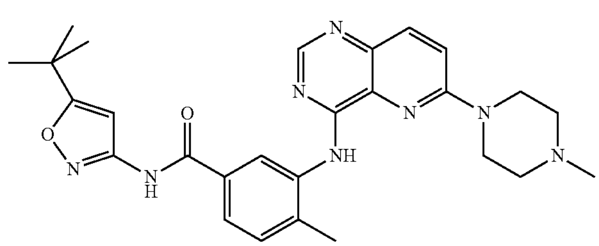 [SMILES: Cc1ccc(C(=O)Nc2cc(C(C)(C)C)on2)cc1Nc1ncnc2ccc(N3CCN(C)CC3)nc12] | 1.85 | 501 |

TABLE 2-continued

Example compounds III-1 bis III-58

| # | Structure | $t_{Ret.}$ (HPLC) | MS $(M + H)^+$ |
|---|---|---|---|
| III-11 | 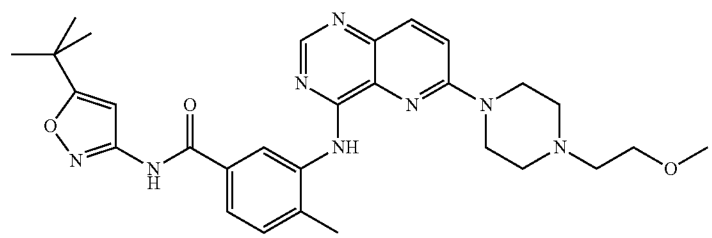 [SMILES: COCCN1CCN(c2ccc3ncnc(Nc4cc(C(=O)Nc5cc(C(C)(C)C)on5)ccc4C)c3n2)CC1] | 1.88 | 545 |
| III-12 | 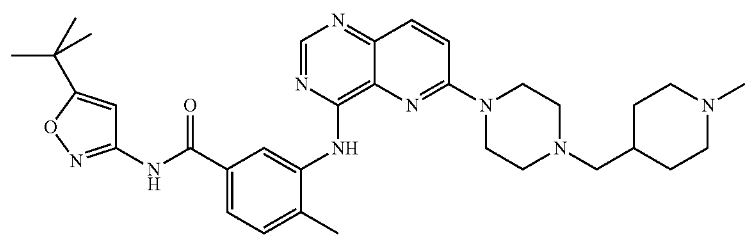 [SMILES: Cc1ccc(C(=O)Nc2cc(C(C)(C)C)on2)cc1Nc1ncnc2ccc(N3CCN(CC4CCN(C)CC4)CC3)nc12] | 2.21 | 598 |
| III-13 | 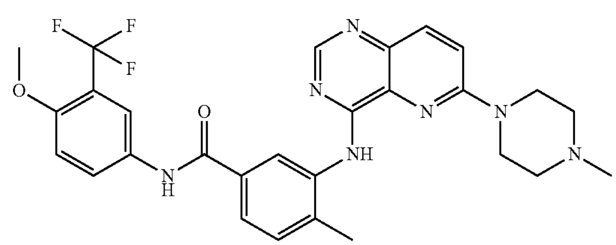 [SMILES: COc1ccc(NC(=O)c2ccc(C)c(Nc3ncnc4ccc(N5CCN(C)CC5)nc34)c2)cc1C(F)(F)F] | 1.90 | 552 |
| III-14 | 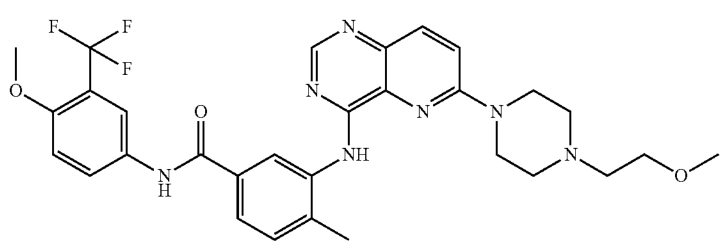 [SMILES: COCCN1CCN(c2ccc3ncnc(Nc4cc(C(=O)Nc5ccc(OC)c(C(F)(F)F)c5)ccc4C)c3n2)CC1] | 1.92 | 596 |
| III-15 | 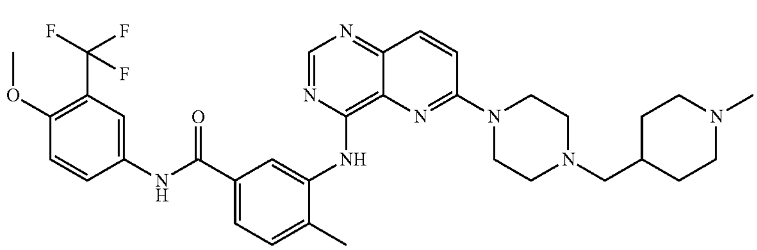 [SMILES: COc1ccc(NC(=O)c2ccc(C)c(Nc3ncnc4ccc(N5CCN(CC6CCN(C)CC6)CC5)nc34)c2)cc1C(F)(F)F] | 2.17 | 649 |

TABLE 2-continued

Example compounds III-1 bis III-58

| # | Structure | t$_{Ret.}$ (HPLC) | MS (M + H)$^+$ |
|---|---|---|---|
| III-16 | 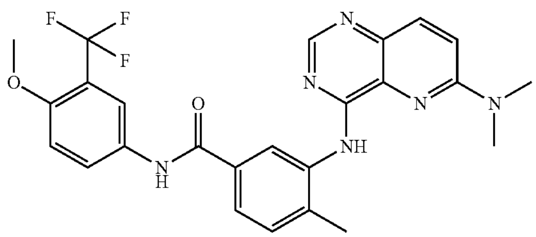 [SMILES: COc1ccc(NC(=O)c2ccc(C)c(Nc3ncnc4ccc(N(C)C)nc34)c2)cc1C(F)(F)F] | 2.04 | 497 |
| III-17 | 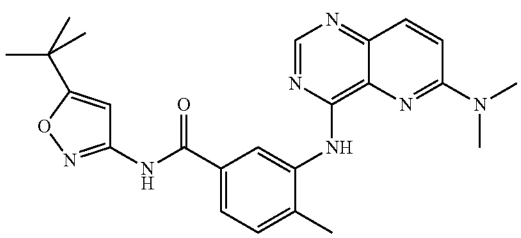 [SMILES: Cc1ccc(C(=O)Nc2cc(C(C)(C)C)on2)cc1Nc1ncnc2ccc(N(C)C)nc12] | 2.00 | 446 |
| III-18 | 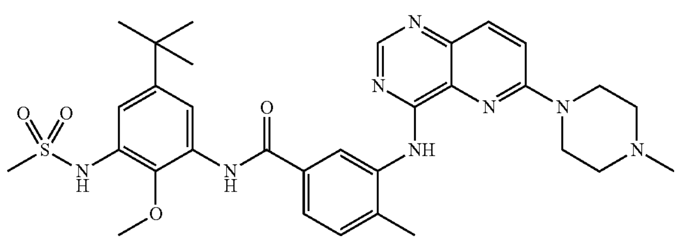 | 1.75 | 633 |
| III-19 | 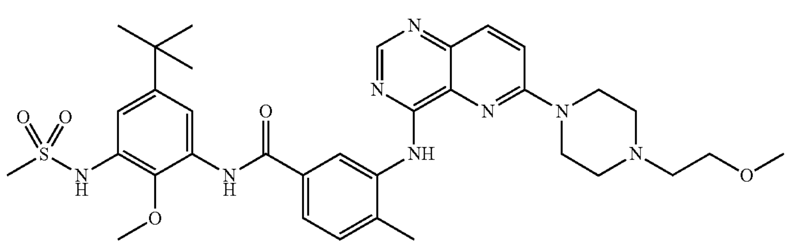 | 1.78 | 677 |
| III-20 | 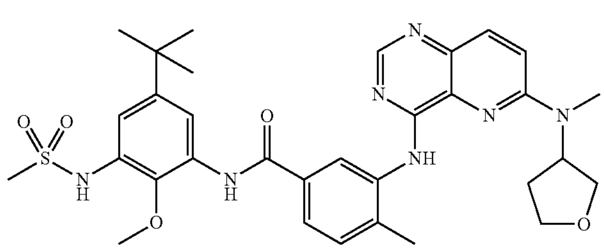 | 1.85 | 634 |

TABLE 2-continued

Example compounds III-1 bis III-58

| # | Structure | $t_{Ret.}$ (HPLC) | MS $(M + H)^+$ |
|---|---|---|---|
| III-21 | 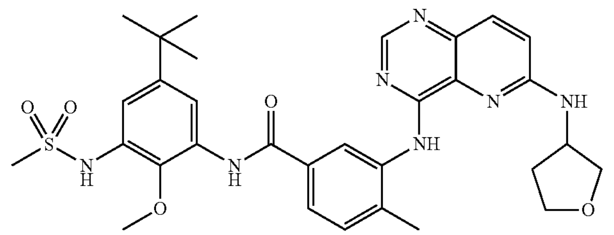 [SMILES: COc1c(NC(=O)c2ccc(C)c(Nc3ncnc4ccc(NC5CCOC5)nc34)c2)cc(C(C)(C)C)cc1NS(C)(=O)=O] | 1.75 | 620 |
| III-22 | 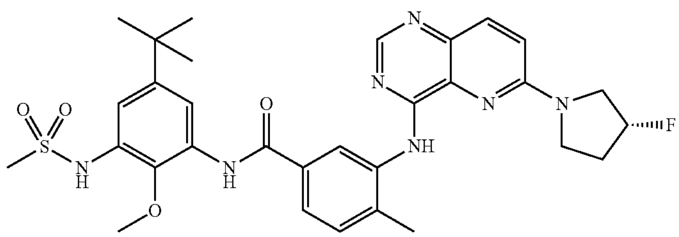 [SMILES: COc1c(NC(=O)c2ccc(C)c(Nc3ncnc4ccc(N5CC[C@@H](F)C5)nc34)c2)cc(C(C)(C)C)cc1NS(C)(=O)=O] | 1.95 | 622 |
| III-23 | 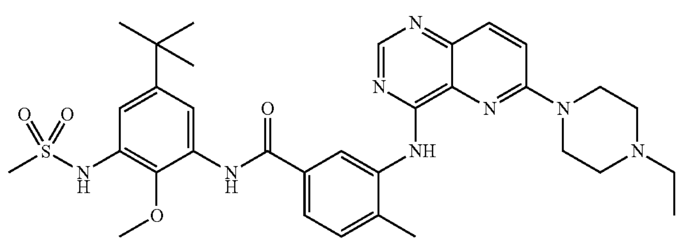 [SMILES: CCN1CCN(c2ccc3ncnc(Nc4cc(C(=O)Nc5cc(C(C)(C)C)cc(NS(C)(=O)=O)c5OC)ccc4C)c3n2)CC1] | 1.86 | 647 |
| III-24 | 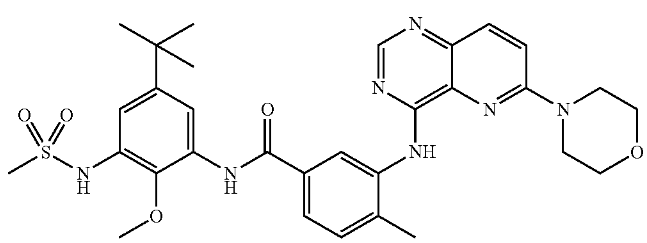 [SMILES: COc1c(NC(=O)c2ccc(C)c(Nc3ncnc4ccc(N5CCOCC5)nc34)c2)cc(C(C)(C)C)cc1NS(C)(=O)=O] | 1.75 | 620 |
| III-25 | 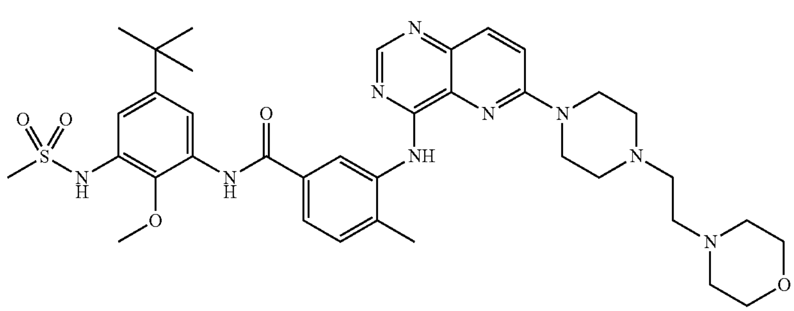 [SMILES: COc1c(NC(=O)c2ccc(C)c(Nc3ncnc4ccc(N5CCN(CCN6CCOCC6)CC5)nc34)c2)cc(C(C)(C)C)cc1NS(C)(=O)=O] | 1.72 | 732 |

TABLE 2-continued

Example compounds III-1 bis III-58

| # | Structure | $t_{Ret.}$ (HPLC) | MS $(M + H)^+$ |
|---|---|---|---|
| III-26 | 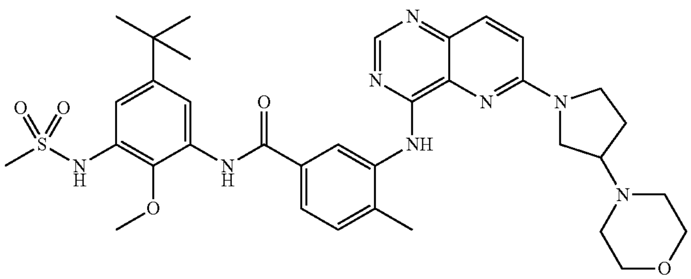 [SMILES: COc1c(NC(=O)c2ccc(C)c(Nc3ncnc4ccc(N5CCC(N6CCOCC6)C5)nc34)c2)cc(C(C)(C)C)cc1NS(C)(=O)=O] | 1.79 | 689 |
| III-27 | 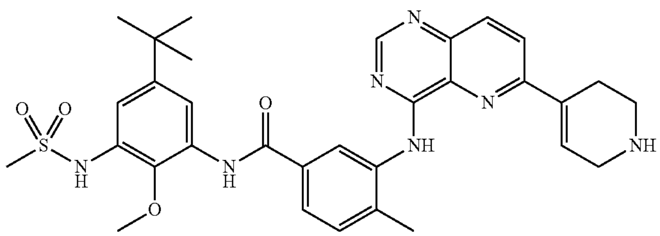 [SMILES: COc1c(NC(=O)c2ccc(C)c(Nc3ncnc4ccc(C5=CCNCC5)nc34)c2)cc(C(C)(C)C)cc1NS(C)(=O)=O] | 1.60 | 616 |
| III-28 | 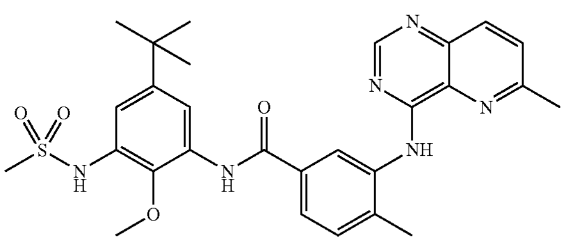 | 1.69 | 549 |
| III-29 | 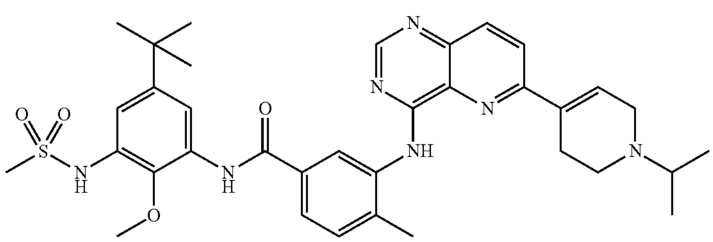 [SMILES: COc1c(NC(=O)c2ccc(C)c(Nc3ncnc4ccc(C5=CCN(C(C)C)CC5)nc34)c2)cc(C(C)(C)C)cc1NS(C)(=O)=O] | 1.99 | 658 |
| III-30 | 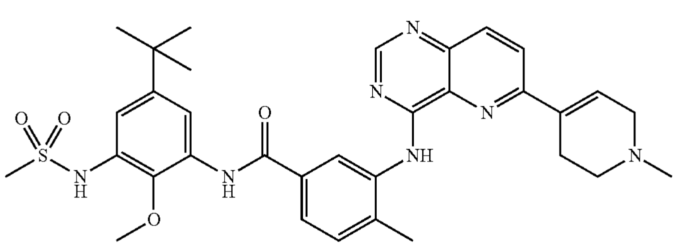 | 1.78 | 630 |

TABLE 2-continued

Example compounds III-1 bis III-58

| # | Structure | $t_{Ret.}$ (HPLC) | MS $(M + H)^+$ |
|---|---|---|---|
| III-31 | 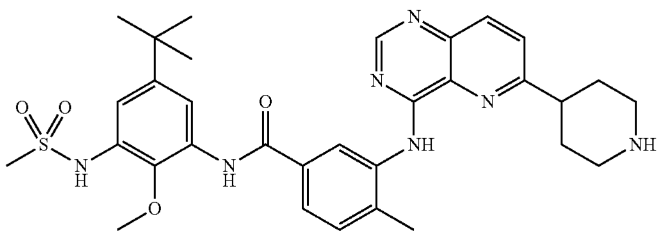 [SMILES: COc1c(NC(=O)c2ccc(C)c(Nc3ncnc4ccc(C5CCNCC5)nc34)c2)cc(C(C)(C)C)cc1NS(C)(=O)=O] | 1.79 | 618 |
| III-32 | 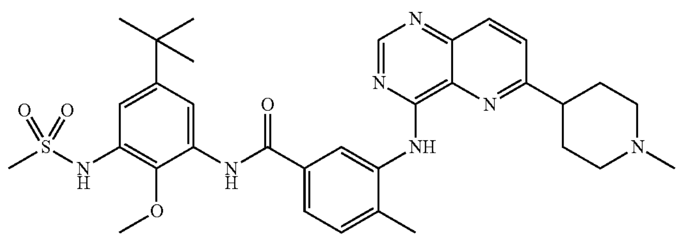 | 1.83 | 632 |
| III-33 | 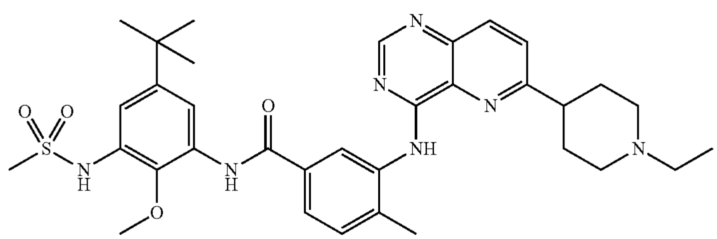 [SMILES: CCN1CCC(c2ccc3ncnc(Nc4cc(C(=O)Nc5cc(C(C)(C)C)cc(NS(C)(=O)=O)c5OC)ccc4C)c3n2)CC1] | 1.95 | 646 |
| III-34 | 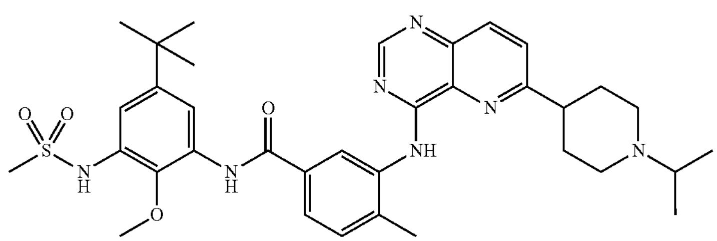 [SMILES: COc1c(NC(=O)c2ccc(C)c(Nc3ncnc4ccc(C5CCN(C(C)C)CC5)nc34)c2)cc(C(C)(C)C)cc1NS(C)(=O)=O] | 2.06 | 660 |
| III-35 | 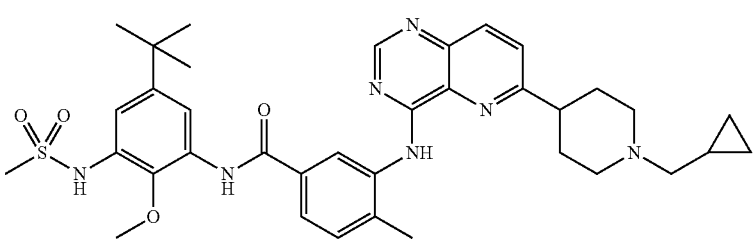 [SMILES: COc1c(NC(=O)c2ccc(C)c(Nc3ncnc4ccc(C5CCN(CC6CC6)CC5)nc34)c2)cc(C(C)(C)C)cc1NS(C)(=O)=O] | 2.07 | 672 |

TABLE 2-continued

Example compounds III-1 bis III-58

| # | Structure | $t_{Ret.}$ (HPLC) | MS $(M + H)^+$ |
|---|---|---|---|
| III-36 | 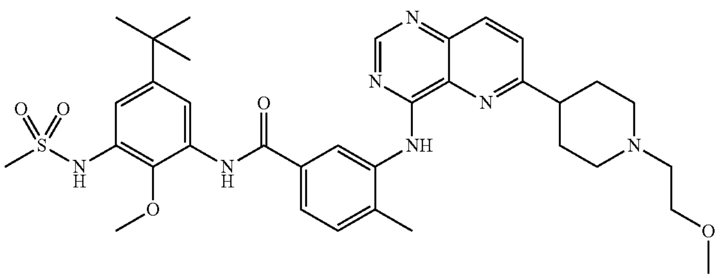 | 1.82 | 676 |
| III-37 | 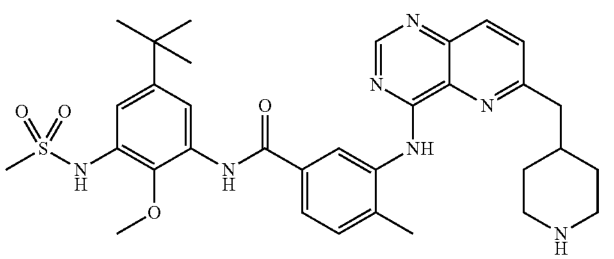 [SMILES: COc1c(NC(=O)c2ccc(C)c(Nc3ncnc4ccc(CC5CCNCC5)nc34)c2)cc(C(C)(C)C)cc1NS(C)(=O)=O] | 1.65 | 632 |
| III-38 | 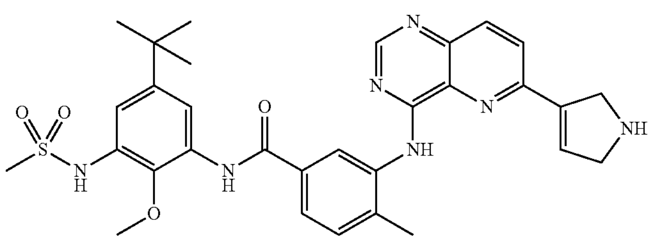 [SMILES: COc1c(NC(=O)c2ccc(C)c(Nc3ncnc4ccc(C5=CCNC5)nc34)c2)cc(C(C)(C)C)cc1NS(C)(=O)=O] | 1.41 | 602 |
| III-39 | 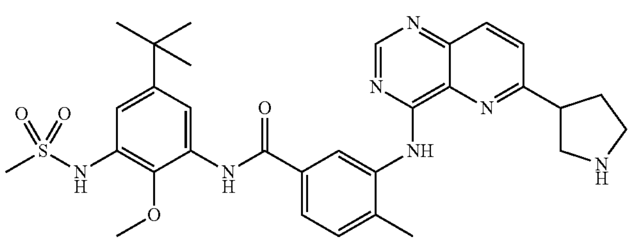 [SMILES: COc1c(NC(=O)c2ccc(C)c(Nc3ncnc4ccc(C5CCNC5)nc34)c2)cc(C(C)(C)C)cc1NS(C)(=O)=O] | 1.73 | 604 |
| III-40 | 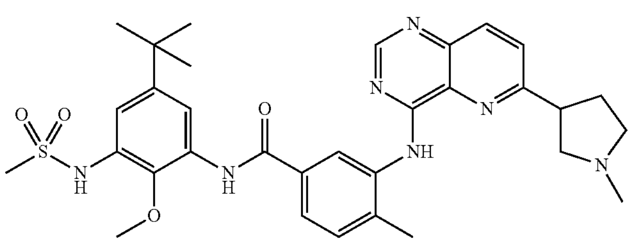 [SMILES: COc1c(NC(=O)c2ccc(C)c(Nc3ncnc4ccc(C5CCN(C)C5)nc34)c2)cc(C(C)(C)C)cc1NS(C)(=O)=O] | 1.87 | 618 |

TABLE 2-continued

Example compounds III-1 bis III-58

| # | Structure | t$_{Ret.}$ (HPLC) | MS (M + H)$^+$ |
|---|---|---|---|
| III-41 | 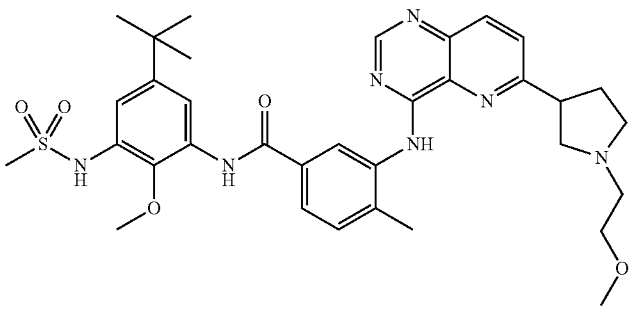 [SMILES: COCCN1CCC(c2ccc3ncnc(Nc4cc(C(=O)Nc5cc(C(C)(C)C)cc(NS(C)(=O)=O)c5OC)ccc4C)c3n2)C1] | 1.87 | 662 |
| III-42 | 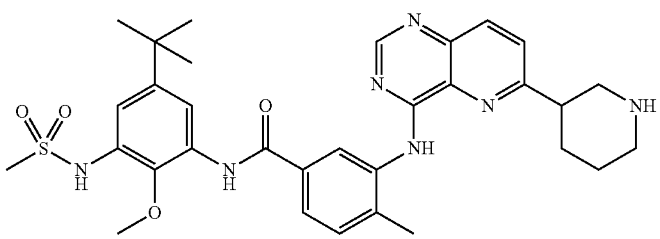 [SMILES: COc1c(NC(=O)c2ccc(C)c(Nc3ncnc4ccc(C5CCCNC5)nc34)c2)cc(C(C)(C)C)cc1NS(C)(=O)=O] | 1.83 | 618 |
| III-43 | 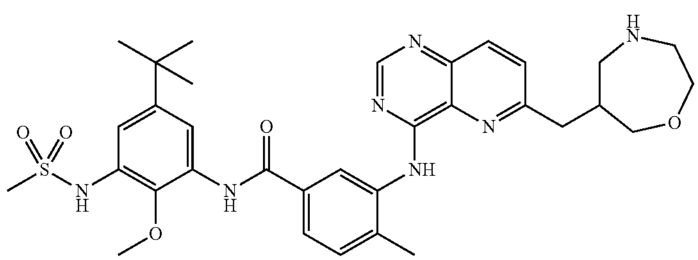 [SMILES: COc1c(NC(=O)c2ccc(C)c(Nc3ncnc4ccc(CC5CNCCOC5)nc34)c2)cc(C(C)(C)C)cc1NS(C)(=O)=O] | 1.81 | 648 |
| III-44 | 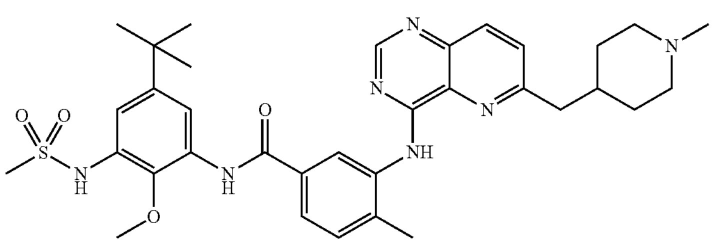 | 1.83 | 646 |
| III-45 | 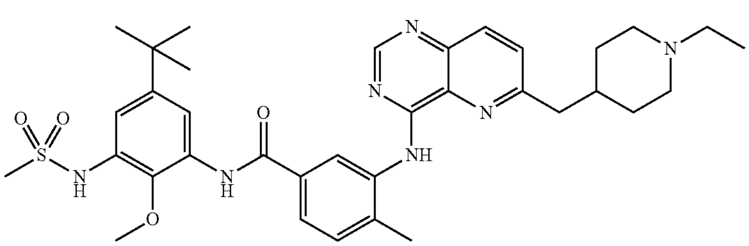 [SMILES: CCN1CCC(Cc2ccc3ncnc(Nc4cc(C(=O)Nc5cc(C(C)(C)C)cc(NS(C)(=O)=O)c5OC)ccc4C)c3n2)CC1] | 1.92 | 660 |

TABLE 2-continued

Example compounds III-1 bis III-58

| # | Structure | $t_{Ret.}$ (HPLC) | MS $(M + H)^+$ |
|---|---|---|---|
| III-46 | 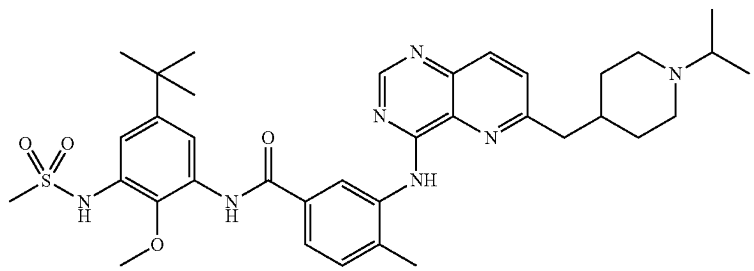 [SMILES: COc1c(NC(=O)c2ccc(C)c(Nc3ncnc4ccc(CC5CCN(C(C)C)CC5)nc34)c2)cc(C(C)(C)C)cc1NS(C)(=O)=O] | 2.03 | 674 |
| III-47 | 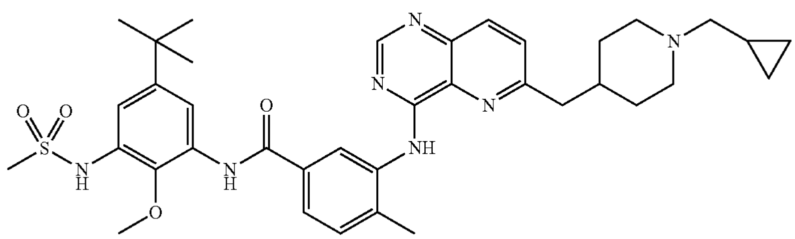 [SMILES: COc1c(NC(=O)c2ccc(C)c(Nc3ncnc4ccc(CC5CCN(CC6CC6)CC5)nc34)c2)cc(C(C)(C)C)cc1NS(C)(=O)=O] | 2.03 | 686 |
| III-48 | 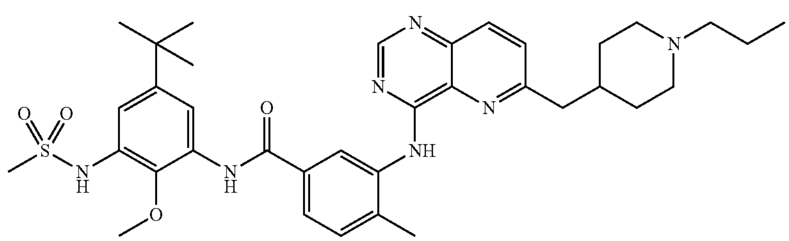 [SMILES: CCCN1CCC(Cc2ccc3ncnc(Nc4cc(C(=O)Nc5cc(C(C)(C)C)cc(NS(C)(=O)=O)c5OC)ccc4C)c3n2)CC1] | 2.05 | 674 |
| III-49 | 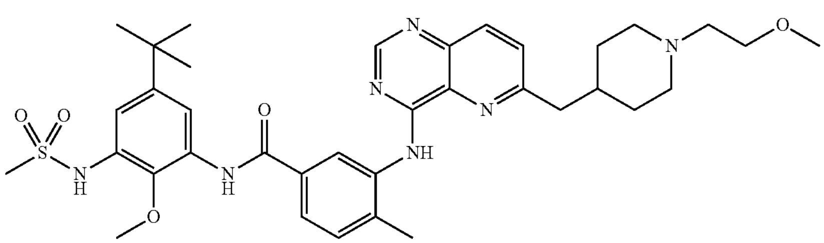 | 1.81 | 690 |
| III-50 | 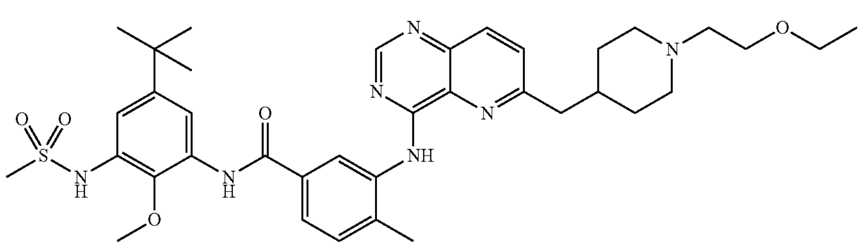 [SMILES: CCOCCN1CCC(Cc2ccc3ncnc(Nc4cc(C(=O)Nc5cc(C(C)(C)C)cc(NS(C)(=O)=O)c5OC)ccc4C)c3n2)CC1] | 1.90 | 704 |

TABLE 2-continued

Example compounds III-1 bis III-58

| # | Structure | $t_{Ret.}$ (HPLC) | MS $(M + H)^+$ |
|---|---|---|---|
| III-51 | 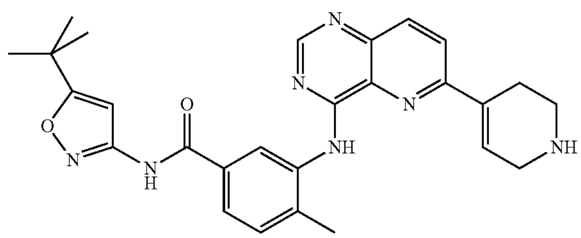 [SMILES: Cc1ccc(C(=O)Nc2cc(C(C)(C)C)on2)cc1Nc1ncnc2ccc(C3=CCNCC3)nc12] | 1.94 | 484 |
| III-52 | 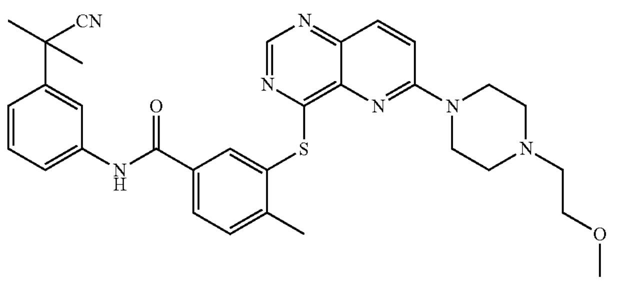 [SMILES: COCCN1CCN(c2ccc3ncnc(Sc4cc(C(=O)Nc5cccc(C(C)(C)C#N)c5)ccc4C)c3n2)CC1] | 1.97 | 582 |
| III-53 | 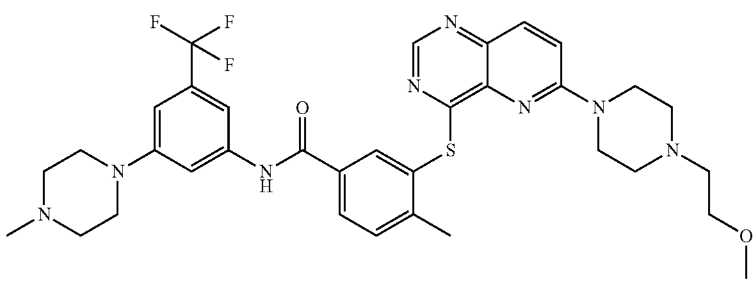 | 2.19 | 681 |
| III-54 | 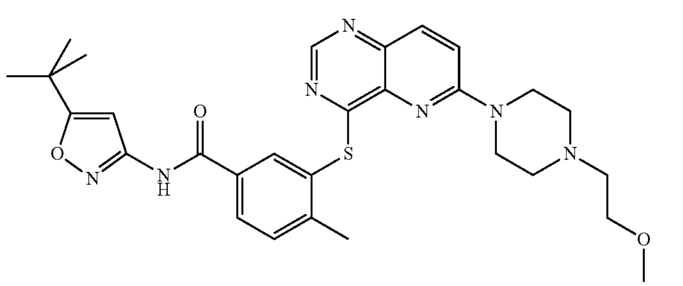 [SMILES: COCCN1CCN(c2ccc3ncnc(Sc4cc(C(=O)Nc5cc(C(C)(C)C)on5)ccc4C)c3n2)CC1] | 2.07 | 562 |

TABLE 2-continued

Example compounds III-1 bis III-58

| # | Structure | $t_{Ret.}$ (HPLC) | MS $(M + H)^+$ |
|---|---|---|---|
| III-55 | 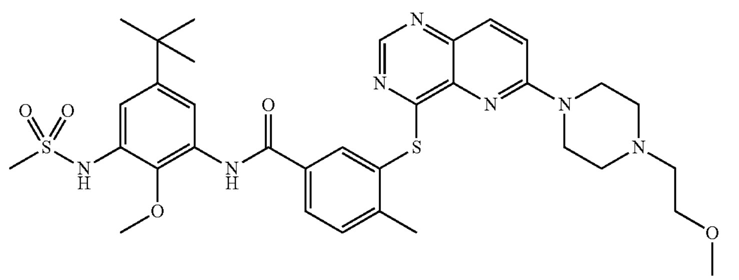 | 1.95 | 694 |
| III-56 | 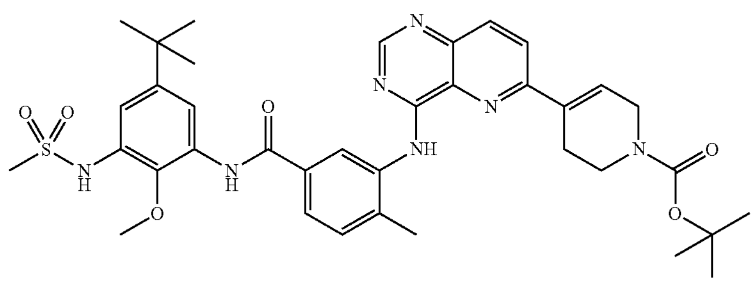 [SMILES: COc1c(NC(=O)c2ccc(C)c(Nc3ncnc4ccc(C5=CCN(C(=O)OC(C)(C)C)CC5)nc34)c2)cc(C(C)(C)C)cc1NS(C)(=O)=O] | 2.08 | 716 |
| III-57 | 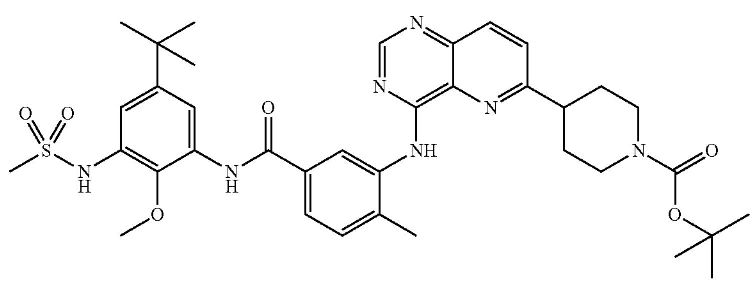 [SMILES: COc1c(NC(=O)c2ccc(C)c(Nc3ncnc4ccc(C5CCN(C(=O)OC(C)(C)C)CC5)nc34)c2)cc(C(C)(C)C)cc1NS(C)(=O)=O] | 2.10 | 718 |
| III-58 | 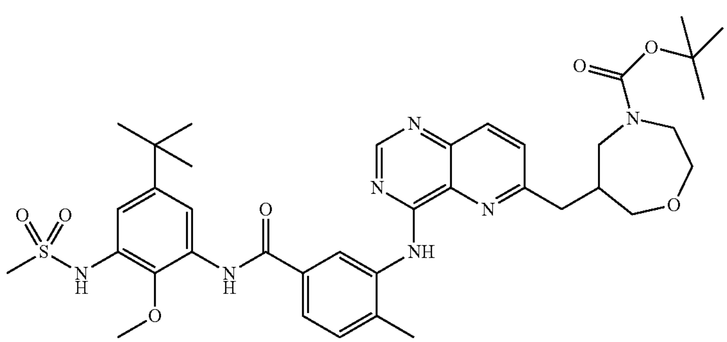 [SMILES: COc1c(NC(=O)c2ccc(C)c(Nc3ncnc4ccc(CC5COCCN(C(=O)OC(C)(C)C)C5)nc34)c2)cc(C(C)(C)C)cc1NS(C)(=O)=O] | 2.08 | 748 |

Reaction scheme D

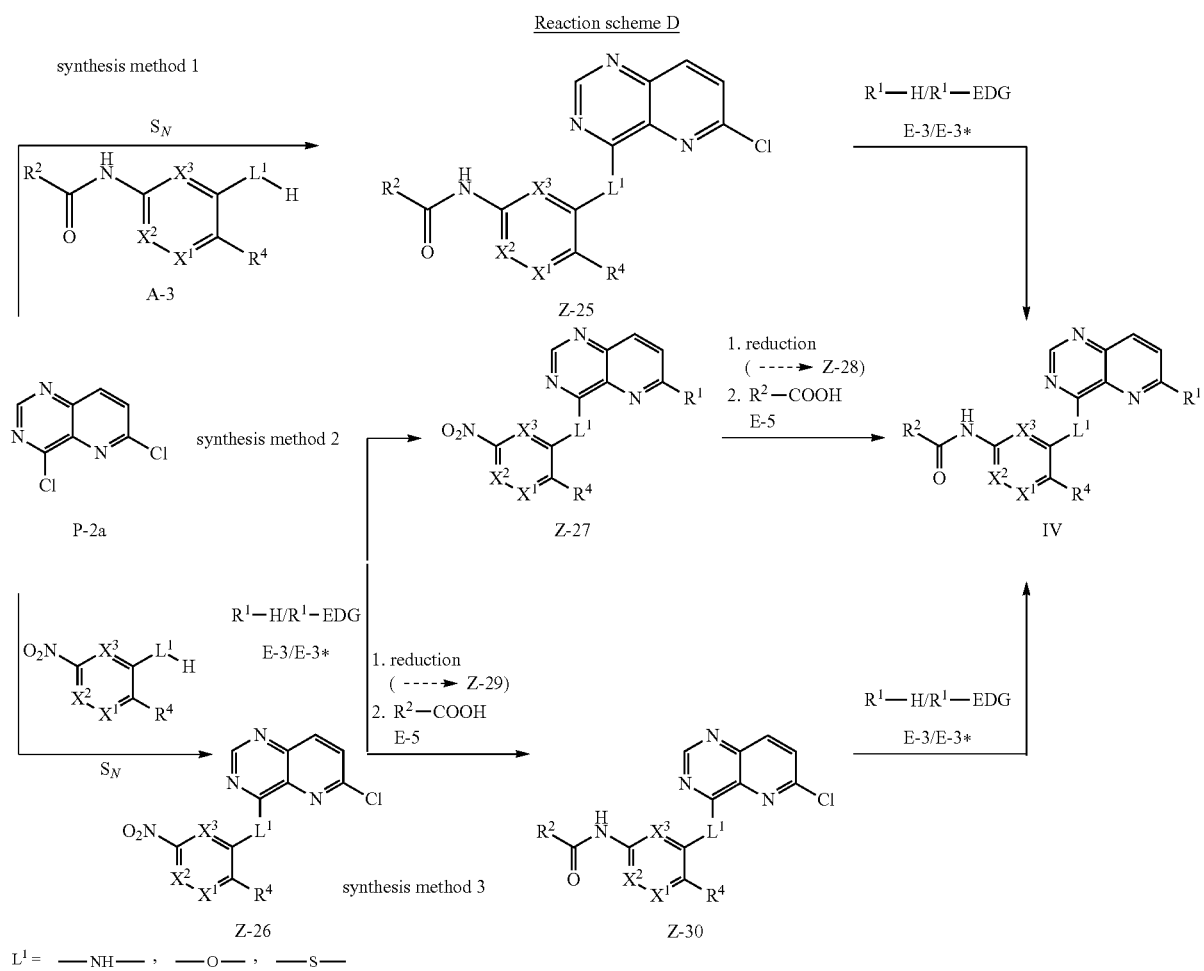

Example Compounds of Type IV:

Example compounds IV differ from those of type III by an inverted amide bond between the central (hetero-)aromatic six-membered ring and the group R² (reaction scheme D). These compounds are obtained by analogous methods to the compounds III, but the reactivities are inverted accordingly in the educt components E-4 and E-5 (for synthesising A-3, cf. reaction scheme B) or A-4 (compared with E-1 and E-2 or A-2, cf. reaction schemes A and C).

For compounds of type IV the following synthesis methods are possible, for example: Starting from P-1a the 4-position is substituted by components A-3 or A-4, preferably at elevated temperature. The components A-3 and A-4 are preferably anilines ($L^1$=—NH—), but also thiophenols and phenols ($L^1$=—S—, —O—) or the corresponding phenoxides.

With regard to the use of A-3 (synthesis method 1, via intermediate compound Z-25) reference may be made to the remarks in connection with reaction scheme B (synthesis method 1).

When A-4 is used (synthesis methods 2 and 3) first of all only the central phenyl or heteroaryl ring and the precursor of a linker fragment (nitro→amino) of the later linker $L^2$ is incorporated. With the intermediate compound Z-26 there are the alternative possibilities of either substituting/coupling the 6-position with a component E-3/E-3* and then, after reduction, introducing the group R² (through the component E-5) (synthesis method 2) or first of all carrying out reduction and amide coupling with E-5 and then carrying out the nucleophilic substitution/coupling by E-3/E-3" (synthesis method 3).

Both the group $R^1$ and the group $R^2$ of compounds IV according to the invention may be modified in other reaction steps (not shown), to obtain more compounds IV according to the invention. These reaction steps may be reactions of substitution, alkylation, acylation, reduction, deprotection or addition.

a) Method for Synthesising A-3a:

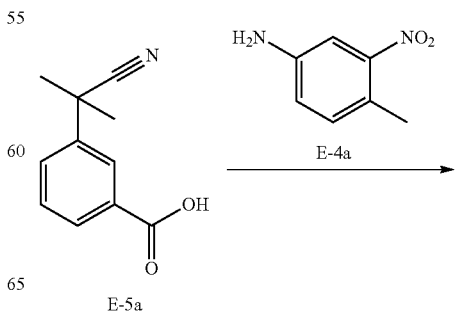

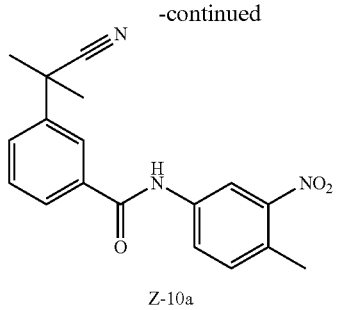

Z-10a

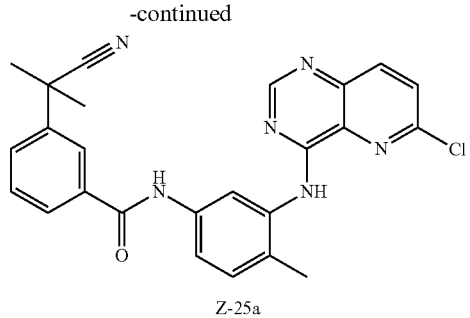

Z-25a

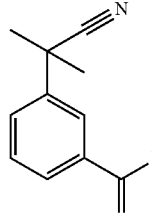

A-3a

Benzoic acid E-5a (1.5 g, 7.93 mmol) is taken up in 20 mL toluene, refluxed, mixed with thionyl chloride (0.9 mL, 12.41 mmol) and refluxed for a further hour with stirring. Then the reaction mixture is evaporated down. The residue is again placed in 20 mL toluene, combined with 4-methyl-3-nitroaniline E-4a (1.206 g, 7.93 mmol) and DIPEA (3.140 mL, 18.30 mmol) and stirred for 3 h at RT. For working up the reaction mixture is combined with 10 mL 8M NaOH solution. The precipitate formed is filtered off, dried overnight at 50° C. dried and Z-10a is obtained.

The aromatic nitro compound Z-10a (2.43 g, 7.52 mmol) is taken up in EtOH (15 mL), combined with ammonium chloride (600 mg, 11.32 mmol) in water (15 mL) and heated to 75° C. At this temperature iron powder (4.0 g, 73 mmol) is added batchwise and the mixture is stirred for a further 30 min at 75° C. After cooling it is filtered through Celite®, washed with EtOH and the filtrate obtained is evaporated down using the rotary evaporator. The residue is mixed with water and extracted 3× with ethyl acetate. The combined organic phases are washed 1× with NaCl solution, dried on MgSO$_4$, evaporated down using the rotary evaporator and A-3a is obtained.

b) Method for Synthesising Z-25a:

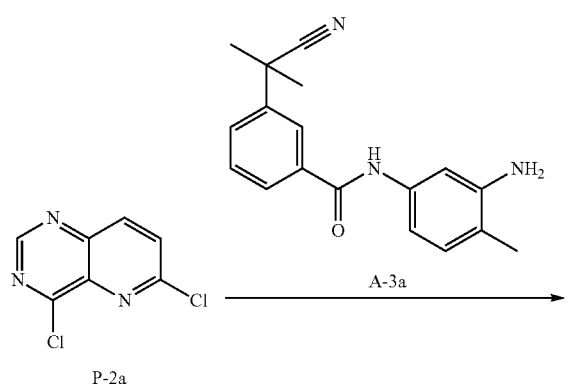

P-2a 4,6-dichloro-pyrido[3,2-d]pyrimidine P-2a (200 mg, 1.0 mmol) and aniline A-3a (300 mg, 1.02 mmol) are placed in isopropanol (5 mL) and heated for 30 min at 100° C. in the microwave reactor. The precipitate formed is filtered off, washed with cyclohexane, dried and Z-25a is obtained (HPLC-MS: t$_{Ret.}$=1.90 min; MS (M+H)$^+$=457/459).

c) Method for Synthesising Example Compound IV-1:

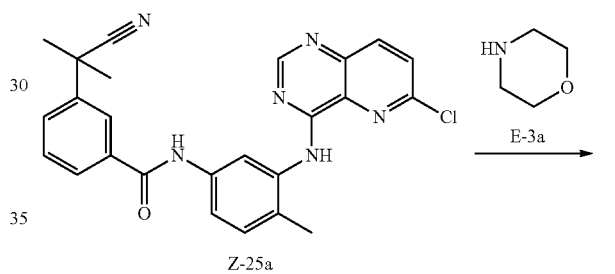

Z-25a

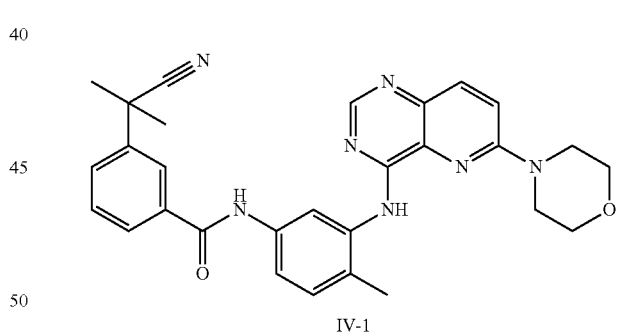

IV-1

Z-25a (82 mg, 0.18 mmol) is taken up in isopropanol (500 µL) and NMP (500 µL). Morpholine E-3a (19 µL, 0.22 mmol) is added and the reaction mixture is stirred for 40 min at 120° C. in the microwave reactor. For working up the mixture is filtered and purified by preparative HPLC. The product-containing fractions of IV-1 (HPLC-MS: t$_{Ret.}$=2.09 min; MS (M+H)$^+$=509) are freeze-dried.

In addition to IV-1 the following novel compounds IV-2 to IV-5 (Table 3) are prepared analogously to methods a) to c) (synthesis method 1).

TABLE 3

Example compounds IV-1 bis IV-5

| # | Structure | $t_{Ret.}$ (HPLC) | MS $(M + H)^+$ |
|---|---|---|---|
| IV-1 | 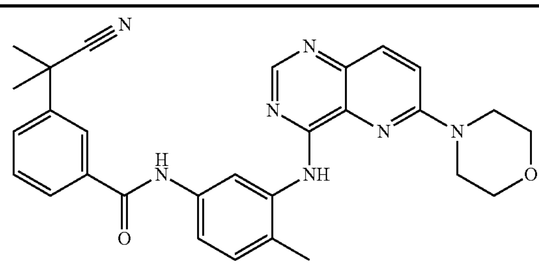 | 1.85 | 508 |
| IV-2 | 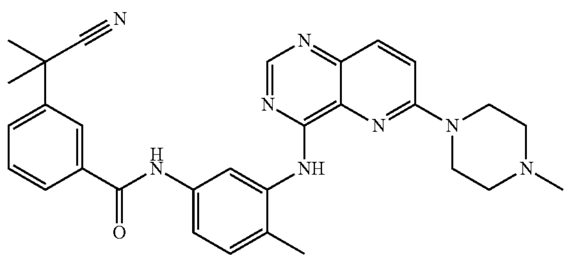 [SMILES: Cc1ccc(NC(=O)c2cccc(C(C)(C)C#N)c2)cc1Nc1ncnc2ccc(N3CCN(C)CC3)nc12] | 1.83 | 521 |
| IV-3 | 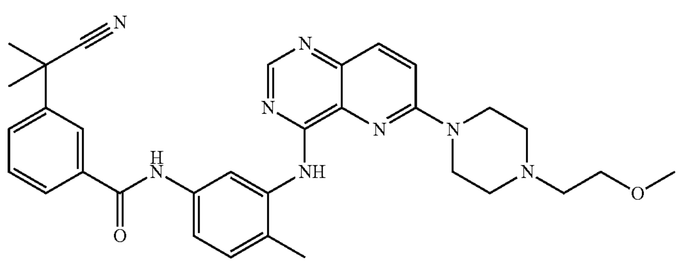 [SMILES: COCCN1CCN(c2ccc3ncnc(Nc4cc(NC(=O)c5cccc(C(C)(C)C#N)c5)ccc4C)c3n2)CC1] | 1.87 | 565 |
| IV-4 | 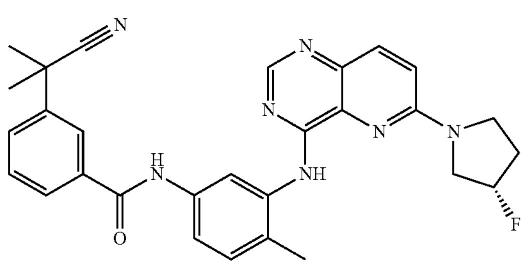 [SMILES: Cc1ccc(NC(=O)c2cccc(C(C)(C)C#N)c2)cc1Nc1ncnc2ccc(N3CC[C@H](F)C3)nc12] | 1.95 | 510 |
| IV-5 | 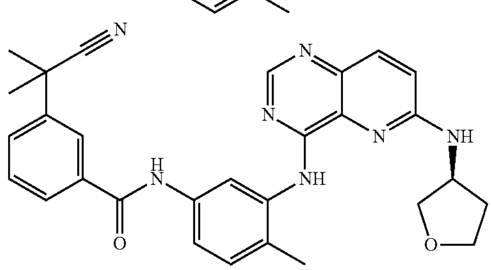 | 1.81 | 508 |

Further References to Reaction Schemes A to D and all the Types of Example Compounds (I to IV):

To synthesise compounds (1) according to the invention the key educts E-1, E-2, E-3, E-4, E-5, A-2 and A-4 are required, in particular. These starting compounds may be obtained in a number of ways. A representative number of synthesis components of this kind are commercially obtainable or maybe prepared by the skilled man using routine methods. In addition, these components and the preparation thereof are known from the prior art or may be prepared analogously to methods in the prior art or be extended thereto. These include in particular methods as published in the following publications: WO 2004/050642, WO 2005/056535, WO 2005/090333, WO 2005/115991, US 2006/100204, WO 2008/003770, WO 2005/023761, WO 2008/021388, WO 2007/075896, WO 2007/056016, WO 2008/089034, WO 2009/003999, WO 2009/003998 and EP 08165437.8

Reference is made in particular to the analogy regarding the methods of synthesis for synthesising pyrimido[5,4-d] pyrimidines in EP 08163897.5.

Besides the primary amines E-2 illustrated in the reaction schemes, secondary cyclic amines such as morpholine, pyrrolidine, pyrrole, pyrazole or imidazole, may also be coupled.

For educts A-4 there is also the alternative possibility of obtaining them from the aromatic nitro acids A-6 by CURTIUS degradation:

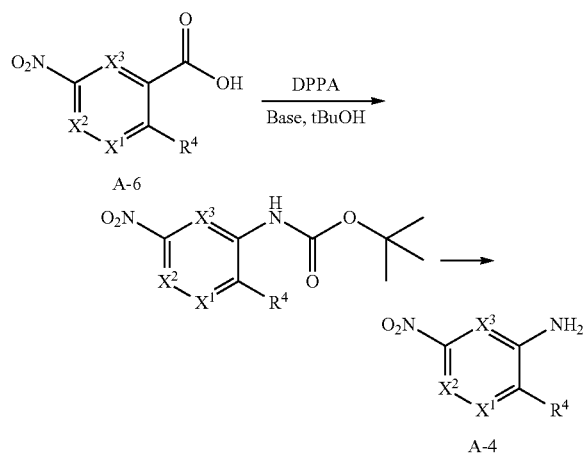

In order to incorporate linker units $L^2$, which are different from —C(O)NH— and —NHC(O)—, the synthesis components needed may be routinely modified. Thus, for example, instead of carboxylic acids, sulphonic acids may be used to synthesise the corresponding sulphonamides. Urea linkers are produced by the reaction of isocyanates with amines or the combination of two amines via a carbonylbiselectrophil (e.g. CDI, triphosgene).

The following Examples describe the biological activity of the compounds according to the invention, without restricting the invention to these Examples.

Compounds of general formula (1) are characterised by their many possible applications in the therapeutic field. Particular mention should be made of those applications in which the inhibition of specific signal enzymes, particularly the inhibiting effect on the proliferation of cultivated human tumour cells but also on the proliferation of other cells such as endothelial cells, for example, are involved.

Kinase Test B-Raf (V600E)

In a dilution series 10 μL of test substance solution are placed in a multiwell plate. The dilution series is selected so that generally a range of concentrations of 2 μM to 0.128 nM or 0.017 nM is covered. If necessary the initial concentration of 2 μM is changed to 50 μM, 10 μM or 0.4 μM or 0.2857 μM and further dilution is carried out accordingly. The final concentration of DMSO is 5%. 10 μL of the B-Raf (V600E)-kinase solution are pipetted in (containing 0.5 ng B-Raf (V600E)-kinase in 20 mM Tris-HCl pH 7.5, 0.1 mM EDTA, 0.1 mM EGTA, 0.286 mM sodium orthovanadate, 10% glycerol, 1 mg/mL bovine serum albumin, 1 mM dithiothreitol) and the mixture is incubated for 1 h at RT under with shaking. The kinase reaction is started by the addition of 20 μL ATP solution [final concentration: 250 μM ATP, 30 mM Tris-HCl pH 7.5, 0.02% Brij, 0.2 mM sodium orthovanadate, 10 mM magnesium acetate, phosphatase cocktail (Sigma, #P2850, dilution recommended by the manufacturer), 0.1 mM EGTA] and 10 μL MEK1 solution [containing 50 ng biotinylated MEK1 (prepared from purified MEK1 according to standard procedure, e.g. with EZ-Link Sulpho-NHS-LC-Biotin reagent, Pierce, #21335) in 50 mM Hepes pH 7.5, 150 mM NaCl, 10% glycerol, 0.02% Brij-35, 0.2 mM PMSF, 0.2 mM benzamidine] and carried out for 60 min at RT with constant shaking. The reaction is stopped by the addition of 12 μL of a 100 mM EDTA solution and incubation is continued for a further 5 min. 55 μL of the reaction solution are transferred into a streptavidin-coated plate (e.g. Streptawell HighBond, Roche, #11989685001) and shaken gently for 1 h at RT, in order to bind biotinylated MEK1 to the plate. After elimination of the liquid the plate is washed five times with 200 μL of 1×PBS and 100 μL solution of primary antibody plus europium-labelled secondary antibody [Anti Phospho-MEK (Ser217/221), Cell Signaling, #9121 and Eu-N1 labeled goat-anti-rabbit antibody, Perkin Elmer, #AD0105], the primary antibody is diluted 1:2000 and the secondary antibody is diluted to 0.4-0.5 μg/mL in Delfia Assay Buffer (Perkin Elmer, #1244-111). After 1 h shaking at RT the solution is poured away and washed five times with 200 μL Delfia Wash Buffer (Perkin Elmer, #4010-0010/#1244-114). After the addition of 200 μL Enhancement Solution (Perkin Elmer, #4001-0010/#1244-105) the mixture is shaken for 10 min at RT and then measured in a Wallac Victor using the program "Delfia Time Resolved Fluorescence (Europium)". $IC_{50}$ values are obtained from these dosage-activity curves using a software program (GraphPadPrizm).

Table 4 gives the $IC_{50}$ values determined for representative example compounds according to the invention using the above B-RAF-kinase test:

TABLE 4

| # | $IC_{50}$ [nM] |
|---|---|
| I-1 | 106 |
| I-2 | 224 |
| I-3 | 316 |
| I-4 | >1400 |
| III-1 | 11 |
| III-2 | 32 |
| III-3 | 7 |
| III-4 | 2060 |
| III-5 | 7 |
| III-6 | 15 |
| III-7 | 4 |
| III-8 | 5 |
| III-9 | 4 |
| III-10 | 12 |
| III-11 | 35 |
| III-12 | 12 |
| III-13 | 57 |

TABLE 4-continued

| # | IC$_{50}$ [nM] |
|---|---|
| III-14 | 140 |
| III-15 | 26 |
| III-16 | 44 |
| III-17 | 9 |
| III-18 | 225 |
| III-19 | 476 |
| III-20 | 24 |
| III-21 | 30 |
| III-22 | 25 |
| III-23 | 508 |
| III-24 | 50 |
| III-25 | 638 |
| III-26 | 1457 |
| III-27 | 101 |
| III-28 | 431 |
| III-29 | 295 |
| III-30 | 344 |
| III-31 | 70 |
| III-32 | 151 |
| III-33 | 185 |
| III-34 | 257 |
| III-35 | 288 |
| III-36 | 443 |
| III-37 | 170 |
| III-38 | 282 |
| III-39 | 151 |
| III-40 | 286 |
| III-41 | 315 |
| III-42 | 229 |
| III-43 | 213 |
| III-44 | 364 |
| III-45 | 530 |
| III-46 | 553 |
| III-47 | 504 |
| III-48 | 583 |
| III-49 | 496 |
| III-50 | 479 |
| III-51 | 23 |
| III-52 | 261 |
| III-53 | 190 |
| III-54 | 269 |
| III-55 | 1617 |
| IV-1 | 4 |
| IV-2 | 8 |
| IV-3 | 18 |
| IV-4 | 11 |
| IV-5 | 5 |

Measurement of the Inhibition of the Proliferation of Cultivated Human Melanoma Cells (SK-MEL-28)

For measuring the proliferation of cultivated human tumour cells, cells of the melanoma cell line SK-MEL-28 [American Type Culture Collection (ATCC)] are cultivated in MEM medium, supplemented with 10% foetal calf serum, 2% sodium bicarbonate, 1 mM to sodium pyruvate, 1% non-essential amino acids (e.g. from Cambrex, #BE13-114E) and 2 mM glutamine. SK-MEL28 cells are placed in 96-well flat bottomed dishes in a density of 2500 cells per well in supplemented MEM medium (see above) and incubated overnight in an incubator (at 37° C. and 5% $CO_2$). The active substances are added to the cells in different concentrations, so that a concentration range of 50 μM to 3.2 nM is covered. If necessary the initial concentration of 50 μM is changed to 10 μM or 2 μM and further dilution is carried out accordingly (to 0.6 nM or 0.12 nM). After an incubation period of a further 72 h 20 □L AlamarBlue reagent (Serotec Ltd., #BUF012B) are added to each well and the cells are incubated for a further 3-6 h. The colour change of the AlamarBlue reagent is determined in a fluorescence spectrophotometer (e.g. Gemini, Molecular Devices). EC$_{50}$ values are calculated using a software program (GraphPadPrizm).

Most of the example compounds of Type I to IV (Tables 1 to 3) exhibit a good to very good activity in the cellular SK-MEL-28 assay, i.e. An EC$_{50}$ value of less than 5 □M, generally less than 1 □M.

Measurement of the Inhibition of the Proliferation of Cultivated Human Melanoma Cells (A375)

For measuring the proliferation of cultivated human tumour cells, cells of the melanoma cell line A375 [American Type Culture Collection (ATCC)] are cultivated in DMEM medium, supplemented with 10% foetal calf serum and 2% sodium bicarbonate. Test substances are tested on A375 cells according to the procedure described for SK-MEL28 cells (see above), but seeding them at 5000 cells per well.

Most of the example compounds of types I to IV (Tables 1 to 3) show good to very good activity in the cellular A375 assay, i.e. an EC$_{50}$ value of less than 5 □M, generally less than 1 □M.

The substances of the present invention are B-Raf-kinase inhibitors. As can be demonstrated by DNA staining followed by FACS or Cellomics Array Scan analysis, the inhibition of proliferation achieved by means of the compounds according to the invention is brought about above all by preventing entry into the DNA synthesis phase. The treated cells arrest in the G1 phase of the cell cycle.

Accordingly, the compounds according to the invention are also tested on other tumour cells. For example these compounds are effective on the colon carcinoma line, e.g. Colo205, and may be used in this and other indications. This demonstrates the usefulness of the compounds according to the invention for the treatment of different types of tumours.

On the basis of their biological properties the compounds of general formula (1) according to the invention, their tautomers, racemates, enantiomers, diastereomers, mixtures thereof and the salts of all the above-mentioned forms are suitable for treating diseases characterised by excessive or abnormal cell proliferation.

Such diseases include for example: viral infections (e.g. HIV and Kaposi's sarcoma); inflammatory and autoimmune diseases (e.g. colitis, arthritis, Alzheimer's disease, glomerulonephritis and wound healing); bacterial, fungal and/or parasitic infections; leukaemias, lymphomas and solid tumours (e.g. carcinomas and sarcomas), skin diseases (e.g. psoriasis); diseases based on hyperplasia which are characterised by an increase in the number of cells (e.g. fibroblasts, hepatocytes, bones and bone marrow cells, cartilage or smooth muscle cells or epithelial cells (e.g. endometrial hyperplasia)); bone diseases and cardiovascular diseases (e.g. restenosis and hypertrophy). They are also suitable for protecting proliferating cells (e.g. hair, intestinal, blood and progenitor cells) from DNA damage caused by radiation, UV treatment and/or cytostatic treatment.

For example, the following cancers may be treated with compounds according to the invention, without being restricted thereto: brain tumours such as for example acoustic neurinoma, astrocytomas such as pilocytic astrocytomas, fibrillary astrocytoma, protoplasmic astrocytoma, gemistocytary astrocytoma, anaplastic astrocytoma and glioblastoma, brain lymphomas, brain metastases, hypophyseal tumour such as prolactinoma, HGH (human growth hormone) producing tumour and ACTH producing tumour (adrenocorticotropic hormone), craniopharyngiomas, medulloblastomas, meningeomas and oligodendrogliomas; nerve tumours (neoplasms) such as for example tumours of the vegetative nervous system such as neuroblastoma sympathicum, ganglioneuroma, paraganglioma (pheochromocytoma, chromaffinoma) and glomus-caroticum tumour, tumours on the peripheral nervous system such as amputation neuroma, neurofibroma, neurinoma (neurilemmoma, Schwannoma) and malignant Schwannoma, as well as tumours of the central nervous system such as brain and bone marrow tumours; intestinal cancer such as for example carcinoma of the rectum, colon, anus, small intestine and duodenum; eyelid tumours such as basalioma or basal cell carcinoma; pancreatic cancer or carcinoma of the pancreas; bladder cancer or carcinoma of the bladder; lung cancer (bronchial carcinoma) such as for example small-cell bronchial carcinomas (oat cell carcinomas) and non-small cell bronchial carcinomas such as plate epithelial carcinomas, adenocarcinomas and large-cell bronchial carcinomas; breast cancer such as for example mammary carcinoma such as infiltrating ductal carcinoma, colloid carcinoma, lobular invasive carcinoma, tubular carcinoma, adenocystic carcinoma and papillary carcinoma; non-Hodgkin's lymphomas (NHL) such as for example Burkitt's lymphoma, low-malignancy non-Hodgkin's lymphomas (NHL) and mucosis fungoides; uterine cancer or endometrial carcinoma or corpus carcinoma; CUP syndrome (Cancer of Unknown Primary); ovarian cancer or ovarian carcinoma such as mucinous, endometrial or serous cancer; gall bladder cancer; bile duct cancer such as for example Klatskin tumour; testicular cancer such as for example seminomas and non-seminomas; lymphoma (lymphosarcoma) such as for example malignant lymphoma, Hodgkin's disease, non-Hodgkin's lymphomas (NHL) such as chronic lymphatic leukaemia, leukaemic reticuloendotheliosis, immunocytoma, plasmocytoma (multiple myeloma), immunoblastoma, Burkitt's lymphoma, T-zone mycosis fungoides, large-cell anaplastic lymphoblastoma and lymphoblastoma; laryngeal cancer such as for example tumours of the vocal cords, supraglottal, glottal and subglottal laryngeal tumours; bone cancer such as for example osteochondroma, chondroma, chondroblastoma, chondromyxoid fibroma, osteoma, osteoid osteoma, osteoblastoma, eosinophilic granuloma, giant cell tumour, chondrosarcoma, osteosarcoma, Ewing's sarcoma, reticulo-sarcoma, plasmocytoma, fibrous dysplasia, juvenile bone cysts and aneurysmatic bone cysts; head and neck tumours such as for example tumours of the lips, tongue, floor of the mouth, oral cavity, gums, palate, salivary glands, throat, nasal cavity, paranasal sinuses, larynx and middle ear; liver cancer such as for example liver cell carcinoma or hepatocellular carcinoma (HCC); leukaemias, such as for example acute leukaemias such as acute lymphatic/lymphoblastic leukaemia (ALL), acute myeloid leukaemia (AML); chronic leukaemias such as chronic lymphatic leukaemia (CLL), chronic myeloid leukaemia (CML); stomach cancer or gastric carcinoma such as for example papillary, tubular and mucinous adenocarcinoma, signet ring cell carcinoma, adenosquamous carcinoma, small-cell carcinoma and undifferentiated carcinoma; melanomas such as for example superficially spreading, nodular, lentigo-maligna and acral-lentiginous melanoma; renal cancer such as for example kidney cell carcinoma or hypernephroma or Grawitz's tumour; oesophageal cancer or carcinoma of the oesophagus; penile cancer; prostate cancer; throat cancer or carcinomas of the pharynx such as for example nasopharynx carcinomas, oropharynx carcinomas and hypopharynx carcinomas; retinoblastoma such as for example vaginal cancer or vaginal carcinoma; plate epithelial carcinomas, adenocarcinomas, in situ carcinomas, malignant melanomas and sarcomas; thyroid carcinomas such as for example papillary, follicular and medullary thyroid carcinoma, as well as anaplastic carcinomas; spinalioma, epidormoid carcinoma and plate epithelial carcinoma of the skin; thymomas, cancer of the urethra and cancer of the vulva.

The new compounds may be used for the prevention, short-term or long-term treatment of the above-mentioned diseases, optionally also in combination with radiotherapy or other "state-of-the-art" compounds, such as e.g. cytostatic or cytotoxic substances, cell proliferation inhibitors, anti-angiogenic substances, steroids or antibodies.

The compounds of general formula (1) may be used on their own or in combination with other active substances according to the invention, optionally also in combination with other pharmacologically active substances.

Chemotherapeutic agents which may be administered in combination with the compounds according to the invention, include, without being restricted thereto, hormones, hormone analogues and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxyprogesterone, octreotide), aromatase inhibitors (e.g. anastrozole, letrozole, liarozole, vorozole, exemestane, atamestane), LHRH agonists and antagonists (e.g. goserelin acetate, luprolide), inhibitors of growth factors (growth factors such as for example "platelet derived growth factor" and "hepatocyte growth factor", inhibitors are for example "growth factor" antibodies, "growth factor receptor" antibodies and tyrosinekinase inhibitors, such as for example cetuximab, gefitinib, imatinib, lapatinib and trastuzumab); antimetabolites (e.g. antifolates such as methotrexate, raltitrexed, pyrimidine analogues such as 5-fluorouracil, capecitabin and gemcitabin, purine and adenosine analogues such as mercaptopurine, thioguanine, cladribine and pentostatin, cytarabine, fludarabine); antitumour antibiotics (e.g. anthracyclins such as doxorubicin, daunorubicin, epirubicin and idarubicin, mitomycin-C, bleomycin, dactinomycin, plicamycin, streptozocin); platinum derivatives (e.g. cisplatin, oxaliplatin, carboplatin); alkylation agents (e.g. estramustin, meclorethamine, melphalan, chlorambucil, busulphan, dacarbazin, cyclophosphamide, ifosfamide, temozolomide, nitrosoureas such as for example carmustin and lomustin, thiotepa); antimitotic agents (e.g. Vinca alkaloids such as for example vinblastine, vindesin, vinorelbin and vincristine; and taxanes such as paclitaxel, docetaxel); topoisomerase inhibitors (e.g. epipodophyllotoxins such as for example etoposide and etopophos, teniposide, amsacrin, topotecan, irinotecan, mitoxantron) and various chemotherapeutic agents such as amifostin, anagrelid, clodronat, filgrastin, interferon alpha, leucovorin, rituximab, procarbazine, levamisole, mesna, mitotane, pamidronate and porfimer.

Suitable preparations include for example tablets, capsules, suppositories, solutions—particularly solutions for injection (s.c., i.v., i.m.) and infusion—elixirs, emulsions or dispersible powders. The content of the pharmaceutically active compound(s) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose) emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, most preferably by oral route. For oral administration the tablets may, of course contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

The dosage for intravenous use is from 1-1000 mg per hour, preferably between 5 and 500 mg per hour. However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

The formulation examples which follow illustrate the present invention without restricting its scope:

Examples of Pharmaceutical Formulations

| A) | Tablets | per tablet |
|---|---|---|
| | active substance according to formula (1) | 100 mg |
| | lactose | 140 mg |
| | corn starch | 240 mg |
| | polyvinylpyrrolidone | 15 mg |
| | magnesium stearate | 5 mg |
| | | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) | Tablets | per tablet |
|---|---|---|
| | active substance according to formula (1) | 80 mg |
| | lactose | 55 mg |
| | corn starch | 190 mg |
| | microcrystalline cellulose | 35 mg |
| | polyvinylpyrrolidone | 15 mg |
| | sodium-carboxymethyl starch | 23 mg |
| | magnesium stearate | 2 mg |
| | | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sod iumcarboxymethyl starch and the magnesium stearate are added and mixed in and the mixture is compressed to form tablets of a suitable size.

| C) | Ampoule solution | |
|---|---|---|
| | active substance according to formula (1) | 50 mg |
| | sodium chloride | 50 mg |
| | water for inj. | 5 mL |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

The invention claimed is:
1. A compound of general formula (1)

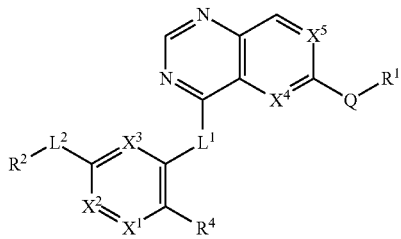

wherein
R¹ is a group optionally substituted by one or more, identical or different $R^b$ and/or $R^c$, selected from among $C_{1-6}$alkyl, $C_{1-6}$haloalkyl, $C_{3-10}$cycloalkyl, $C_{6-10}$aryl, 5-12 membered heteroaryl and 3-14 membered heterocycloalkyl, or
a suitable substituent, selected from among —OR$^c$, —SR$^c$, —NR$^c$R$^c$, —NR$^g$NR$^c$R$^c$ and —S(O)R$^c$;
R² is a group optionally substituted by one or more, identical or different $R^b$ and/or $R^c$, selected from among $C_{1-6}$alkyl, $C_{1-6}$haloalkyl, $C_{3-10}$cycloalkyl, $C_{6-10}$aryl, 5-12 membered heteroaryl and 3-14 membered heterocycloalkyl;
R⁴ is $C_{1-4}$alkyl;
X¹, X² and X³ are each —CR⁴*═, and R⁴* is hydrogen;
X⁴ is —N═;
X⁵ is —CH═,
L¹ is selected from among —CH₂—, —NH—, —NMe—, —O— and —S—;
L² is selected from among —C(O)NH—, —C(O)N(C$_{1-4}$alkyl)-, —NHC(O)—, —N(C$_{1-4}$alkyl)C(O)— and —C(O)—,
while in the notation used above L² on the left binds to R²;
Q denotes a bond or a methylene group;
each $R^b$ is a suitable substituent and is selected independently of one another from among —OR$^c$, —SR$^c$, —NR$^c$R$^c$, —ONR$^c$R$^c$, —N(OR$^c$)R$^c$, —NR$^g$NR$^c$R$^c$, halogen, —CN, —NO₂, —N₃, —C(O)R$^c$, —C(O)OR$^c$, —C(O)NR$^c$R$^c$, —C(O)NR$^g$NR$^c$R$^c$, —C(O)NR$^g$OR$^c$, —C(NR$^g$)R$^c$, —N═CR$^c$R$^c$, —C(NR$^g$)OR$^c$, —C(NR$^g$)NR$^c$R$^c$, —C(NR$^g$)NR$^g$NR$^c$R$^c$, —C(NOR$^g$)R$^c$, —C(NOR$^g$)NR$^c$R$^c$, —C(NNR$^g$R$^g$)R$^c$, —OS(O)R$^c$, —OS(O)OR$^c$, —OS(O)NR$^c$R$^c$, —OS(O)₂R$^c$, —OS(O)₂OR$^c$, —OS(O)₂NR$^c$R$^c$, —OC(O)R$^c$, —OC(O)OR$^c$, —OC(O)NR$^c$R$^c$, —OC(NR$^g$)R$^c$, —OC(NR$^g$)NR$^c$R$^c$, —ONR$^g$C(O)R$^c$, —S(O)R$^B$, —S(O)OR$^c$, —S(O)NR$^c$R$^c$, —S(O)₂R$^c$, —S(O)₂OR$^c$, —S(O)₂NR$^c$R$^c$, —NR$^g$C(O)R$^c$, —NR$^g$C(O)OR$^c$, —NR$^g$C(O)NR$^c$R$^c$, —NR$^g$C(O)NR$^g$NR$^c$R$^c$, —NR$^g$C(NR$^g$)R$^c$, —N═CR$^c$NR$^c$R$^c$, —NR$^g$C(NR$^g$)OR$^c$, —NR$^g$C(NR$^g$)NR$^c$R$^c$, —NR$^g$C(NOR$^g$)R$^c$, —NR$^g$S(O)R$^c$, —NR$^g$S(O)OR$^c$, —NR$^g$S(O)₂R$^c$, —NR$^g$S(O)₂OR$^c$, —NR$^g$S(O)₂NR$^c$R$^c$, —NR$^g$NR$^g$C(O)R$^c$, —NR$^g$NR$^g$C(O)NR$^c$R$^c$, —NR$^g$NR$^g$C(NR$^g$)R$^c$ and —N(OR$^g$)C(O)R$^c$ and the bivalent substituents ═O, ═S, ═NR$^g$, ═NOR$^g$, ═NNR$^g$R$^g$ and ═NNR$^g$C(O)NR$^g$R$^g$, while these bivalent substituents may only be substituents in non-aromatic ring systems;
each R$^c$ independently denotes hydrogen or a group optionally substituted by one or more, identical or different $R^d$ and/or $R^e$, selected from among $C_{1-6}$alkyl, 2-6 membered heteroalkyl, $C_{1-6}$haloalkyl, $C_{3-10}$cycloalkyl, $C_{6-10}$aryl, 5-12 membered heteroaryl and 3-14 membered heterocycloalkyl;
each $R^d$ is a suitable substituent and is independently selected from among —OR$^e$, —SR$^e$, —NR$^e$R$^e$, —ONR$^e$R$^e$, —N(OR$^e$)R$^e$, —N(R$^g$)NR$^e$R$^e$, halogen, —CN, —NO, —NO₂, —N₃, —C(O)R$^e$, —C(O)OR$^e$, —C(O)NR$^e$R$^e$, —C(O)NR$^g$NR$^e$R$^e$, —C(O)NR$^g$OR$^e$, —C(NR$^g$)R$^e$, —N═CR$^e$R$^e$, —C(NR$^g$)OR$^e$, —C(NR$^g$)NR$^e$R$^e$, —C(NR$^g$)NR$^g$NR$^e$R$^e$, —C(NOR$^g$)R$^e$, —C(NOR$^g$)NR$^e$R$^e$, —C(NNR$^g$R$^g$)R$^e$, —OS(O)R$^e$, —OS(O)OR$^e$, —OS(O)NR$^e$R$^e$, —OS(O)₂R$^e$, —OS(O)₂OR$^e$, —OS(O)₂NR$^e$R$^e$, —OC(O)R$^e$, —OC(O)OR$^e$, —OC(O)NR$^e$R$^e$, —OC(NR$^g$)R$^e$, —OC(NR$^g$)NR$^e$R$^e$, —ONR$^g$C(O)R$^e$, —S(O)R$^e$, —S(O)OR$^e$, —S(O)NR$^e$R$^e$, —S(O)₂R$^e$, —S(O)₂OR$^e$, —S(O)₂NR$^e$R$^e$, —NR$^g$C(O)R$^e$, —NR$^g$C(O)OR$^e$, —NR$^g$C(O)NR$^e$R$^e$, —NR$^g$C(O)NR$^g$NR$^e$R$^e$, —NR$^g$C(NR$^g$)R$^e$, —N═CR$^e$NR$^e$R$^e$, —NR$^g$C(NR$^g$)OR$^e$, —NR$^g$C(NR$^g$)NR$^e$R$^e$, —NR$^g$C(NR$^g$)SR$^e$, —NR$^g$C(NOR$^g$)R$^e$, —NR$^g$S(O)R$^e$, —NR$^g$S(O)OR$^e$, —NR$^g$S(O)₂R$^e$, —NR$^g$S(O)₂OR$^e$, —NR$^g$S(O)₂NR$^e$R$^e$, —NR$^g$NR$^g$C(O)R$^e$, —NR$^g$NR$^g$C(O)NR$^e$R$^e$, —NR$^g$NR$^g$C(NR$^g$)R$^e$ and —N(OR$^g$)C(O)R$^e$ and the bivalent substituents ═O, ═S, ═NR$^g$, ═NOR$^g$, ═NNR$^g$R$^g$ and ═NNR$^g$C(O)NR$^g$R$^g$, while these bivalent substituents may only be substituents in non-aromatic ring systems;
each R$^e$ independently denotes hydrogen or a group optionally substituted by one or more, identical or different $R^f$ and/or $R^g$, selected from among $C_{1-6}$alkyl, 2-6 membered heteroalkyl, $C_{1-6}$haloalkyl, $C_{3-10}$cycloalkyl, $C_{6-10}$aryl, 5-12 membered heteroaryl and 3-14 membered heterocycloalkyl;
each $R^f$ is a suitable substituent and is independently selected from among —OR$^g$, —SR$^g$, —NR$^g$R$^g$, —ONR$^g$R$^g$, —N(OR$^g$)R$^g$, —N(R$^h$)NR$^g$R$^g$, halogen, —CN, —NO₂, —N₃, —C(O)R$^g$, —C(O)OR$^g$, —C(O)NR$^g$R$^g$, —C(O)NR$^h$NR$^g$R$^g$, —C(O)NR$^h$OR$^g$, —C(NR$^h$)R$^g$, —N═CR$^g$R$^g$, —C(NR$^h$)OR$^g$, —C(NR$^h$)NR$^g$R$^g$, —C(NR$^h$)NR$^h$NR$^g$R$^g$, —C(NOR$^h$)R$^g$, —C(NOR$^h$)NR$^g$R$^g$, —C(NNR$^h$R$^h$)R$^g$, —OS(O)R$^g$, —OS(O)OR$^g$, —OS(O)NR$^g$R$^g$, —OS(O)₂R$^g$, —OS(O)₂OR$^g$, —OS(O)₂NR$^g$R$^g$, —OC(O)R$^g$, —OC(O)OR$^g$, —OC(O)NR$^g$R$^g$, —OC(NR$^h$)R$^g$, —OC(NR$^h$)NR$^g$R$^g$, —ONR$^h$C(O)R$^g$, —S(O)R$^g$, —S(O)OR$^g$, —S(O)NR$^g$R$^g$, —S(O)₂R$^g$, —S(O)₂OR$^g$, —S(O)₂NR$^g$R$^g$, —NR$^h$C(O)R$^g$, —NR$^h$C(O)OR$^g$, —NR$^h$C(O)NR$^g$R$^g$, —NR$^h$C(O)NR$^h$NR$^g$R$^g$, —NR$^h$C(NR$^h$)R$^g$, —N═CR$^g$NR$^g$R$^g$, —NR$^h$C(NR$^h$)OR$^g$, —NR$^h$C(NR$^h$)NR$^g$R$^g$, —NR$^h$C(NOR$^h$)R$^g$, —NR$^h$S(O)R$^g$, —NR$^h$S(O)OR$^g$, —NR$^h$S(O)₂R$^g$, —NR$^h$S(O)₂OR$^g$, —NR$^h$S(O)₂NR$^g$R$^g$, —NR$^h$NR$^h$C(O)R$^g$, —NR$^h$NR$^h$C(O)NR$^g$R$^g$, —NR$^h$NR$^h$C(NR$^h$)R$^g$ and —N(OR$^h$)C(O)R$^g$ and the bivalent substituents ═O, ═S, ═NR$^h$, ═NOR$^h$, ═NNR$^h$R$^h$ and ═NNR$^h$C(O)NR$^h$R$^h$, while these bivalent substituents may only be substituents in non-aromatic ring systems;
each R$^g$ independently denotes hydrogen or a group optionally substituted by one or more, identical or different $R^h$, selected from among $C_{1-6}$alkyl, 2-6 membered heteroalkyl, $C_{1-6}$haloalkyl, $C_{3-10}$cycloalkyl, $C_{6-10}$aryl, 5-12 membered heteroaryl and 3-14 membered heterocycloalkyl;
each R$^h$ is independently selected from among hydrogen, $C_{1-6}$alkyl, 2-6 membered heteroalkyl, $C_{1-6}$haloalkyl, $C_{3-10}$cycloalkyl, $C_{6-10}$aryl, 5-12 membered heteroaryl and 3-14 membered heterocycloalkyl;

or the compounds of formula (1) may optionally also be in the form of a tautomer, racemate, enantiomer, diastereomer or a mixture thereof, or as respective pharmacologically acceptable salts of all the above-mentioned forms.

2. The compound according to claim 1, wherein
$R^1$ is a group optionally substituted by one or more, identical or different $R^b$ and/or $R^c$, selected from among 5-12 membered heteroaryl and 3-14 membered heterocycloalkyl, and $R^b$ and $R^c$ are defined as in claim 1.

3. The compound according to claim 2, wherein
$R^1$ is a 3-7 membered, monocyclic and nitrogen-containing heterocycloalkyl or 6-10 membered, bicyclic and nitrogen-containing heterocycloalkyl optionally substituted by one or more, identical or different $R^b$ and/or $R^c$,
$R^1$ binds to Q via a nitrogen atom.

4. The compound according to claim 2, wherein
$R^1$ is a 3-7 membered, monocyclic and nitrogen-containing heterocycloalkyl or 6-10 membered, bicyclic and nitrogen-containing heterocycloalkyl optionally substituted by one or more, identical or different $R^b$ and/or $R^c$,
$R^1$ binds to Q via a carbon atom.

5. The compound according to claim 3, wherein
$R^1$ is a group optionally substituted by one or more, identical or different $R^b$ and/or $R^c$, selected from among piperidyl, perhydro-1,4-diazepinyl, piperazinyl, octahydro-pyrrolo[1,2-a]pyrazinyl, 2,5-diazabicyclo[2,2,1]heptyl, octahydro-pyrido[1,2-a]pyrazinyl, perhydro-1,4-oxazepinyl, morpholinyl, pyrrolidinyl, perhydroazepinyl, thiomorpholinyl, thiazolidinyl, imidazolidinyl and azetidinyl.

6. The compound according to claim 2, wherein
the heteroaryl or heterocycloalkyl that binds directly to Q is substituted by one or more substituents, each independently selected from among $R^{b1}$ and $R^{c1}$;
each $R^{b1}$ is independently selected from among $-NR^{c1}R^{c1}$, halogen, $-C(O)R^{c1}$ and $=O$, while the latter substituent may only be a substituent in non-aromatic ring systems,
each $R^d$ independently denotes hydrogen or is a group optionally substituted by one or more, identical or different $R^{d1}$ and/or $R^{e1}$, selected from among $C_{1-6}$alkyl, $C_{3-10}$cycloalkyl, 5-12 membered heteroaryl and 3-14 membered heterocycloalkyl,
each $R^{d1}$ corresponds to a group $-OR^{e1}$,
each $R^{e1}$ independently denotes hydrogen or is a group optionally substituted by one or more, identical or different $C_{1-6}$alkyl, selected from among $C_{1-6}$alkyl, $C_{3-10}$cycloalkyl and 3-14 membered heterocycloalkyl.

7. The compound according to claim 1, wherein
$R^1$ denotes $-NR^{c2}R^{c3}$ and
$R^{c2}$ and $R^{c3}$ are each independently defined in the same way as $R^c$ in claim 1.

8. The compound according to claim 1, wherein
$L^1$ denotes $-NH-$ or $-NMe-$.

9. The compound according to claim 1, wherein
$R^2$ is a group optionally substituted by one or more, identical or different $R^b$ and/or $R^c$, selected from among $C_{6-10}$aryl and 5-12 membered heteroaryl and
$R^b$ and $R^c$ are defined as in claim 1.

10. The compound according to claim 9, wherein
$R^2$ is a group optionally substituted by one or more, identical or different $R^b$ and/or $R^c$, selected from among phenyl and 5-6 membered heteroaryl and
$R^b$ and $R^c$ are defined as in claim 1.

11. The compound according to claim 4, wherein
$R^1$ is a group optionally substituted by one or more, identical or different $R^b$ and/or $R^c$, selected from among piperidyl, perhydro-1,4-diazepinyl, piperazinyl, octahydro-pyrrolo[1,2-a]pyrazinyl, 2,5-diazabicyclo[2,2,1]heptyl, octahydro-pyrido[1,2-a]pyrazinyl, perhydro-1,4-oxazepinyl, morpholinyl, pyrrolidinyl, perhydroazepinyl, thiomorpholinyl, thiazolidinyl, imidazolidinyl and azetidinyl.

12. A pharmaceutical preparation, containing as active substance one or more compounds of general formula (1) according to claim 1 or the pharmacologically acceptable salt or salts thereof, optionally in combination with conventional excipients and/or carriers.

* * * * *

UNITED STATES PATENT AND TRADEMARK OFFICE
CERTIFICATE OF CORRECTION

PATENT NO.         : 8,569,316 B2                                            Page 1 of 1
APPLICATION NO.    : 13/148964
DATED              : October 29, 2013
INVENTOR(S)        : Ettmayer et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 89 days.

Signed and Sealed this
Twenty-fourth Day of February, 2015

Michelle K. Lee
*Deputy Director of the United States Patent and Trademark Office*